US012582557B2

(12) United States Patent
Schneider et al.

(10) Patent No.: US 12,582,557 B2
(45) **Date of Patent: *Mar. 24, 2026**

(54) METHOD AND APPARATUS FOR BONDING ELASTIC PARTS UNDER TENSION TO AN ADVANCING CARRIER

(71) Applicant: The Procter & Gamble Company, Cincinnati, OH (US)

(72) Inventors: Uwe Schneider, Cincinnati, OH (US); Michael Brian Quade, Blue Ash, OH (US); Jason Edward Naylor, Loveland, OH (US); Jeromy Thomas Raycheck, South Lebanon, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/829,418

(22) Filed: Sep. 10, 2024

(65) Prior Publication Data

US 2024/0423848 A1     Dec. 26, 2024

Related U.S. Application Data

(63) Continuation of application No. 16/864,267, filed on May 1, 2020, now Pat. No. 12,115,042.

(Continued)

(51) Int. Cl.
*A61F 13/49*         (2006.01)
*A61F 13/15*         (2006.01)
(Continued)

(52) U.S. Cl.
CPC .. *A61F 13/15593* (2013.01); *A61F 13/15723* (2013.01); *A61F 13/15764* (2013.01);
(Continued)

(58) Field of Classification Search
CPC .......... A61F 13/49011; A61F 13/15723; A61F 13/15764; B32B 38/0004; Y10T 156/1057; Y10T 156/1062
See application file for complete search history.

(56)              References Cited

U.S. PATENT DOCUMENTS 3,091,550 A    5/1963  Doying
3,113,225 A   12/1963  Claus
             (Continued)

FOREIGN PATENT DOCUMENTS

CN        1144472 A     3/1997
CN        1224606 A     8/1999
             (Continued)

OTHER PUBLICATIONS

"Surround." Merriam-Webster.com Dictionary, Merriam-Webster, https ://www .merriam-webster.com/dictionary/surround. Accessed Jun. 15, 2021, 8 Pages.

(Continued)

*Primary Examiner* — Michael A Tolin
*Assistant Examiner* — Christopher C Caillouet
(74) *Attorney, Agent, or Firm* — Gregory P. Habiak; Charles R. Matson

(57)              ABSTRACT

The present disclosure relates to methods and apparatuses for stretching, transferring, and bonding elastic parts under tension to an advancing carrier substrate during the assembly of absorbent articles. A continuous carrier substrate may be advanced in a machine direction at a first speed, and a discrete elastic part may be cut from a continuous elastic substrate having a direction of stretch in a cross direction. The speed of the discrete elastic part is changed from a second speed to the first speed, and the central region of the discrete elastic part is stretched in the cross direction. The discrete elastic part is bonded with the continuous carrier (Continued)

substrate such that the stretched central region extends in the cross direction between the first and second longitudinal edges of the continuous carrier substrate. The discrete elastic part may also be bonded with the carrier substrate with adhesive and/or mechanical bonds.

20 Claims, 23 Drawing Sheets

Related U.S. Application Data

(60) Provisional application No. 62/930,808, filed on Nov. 5, 2019, provisional application No. 62/930,181, filed on Nov. 4, 2019, provisional application No. 62/930,198, filed on Nov. 4, 2019, provisional application No. 62/855,001, filed on May 31, 2019.

(51) Int. Cl.

| | |
|---|---|
| *A61F 13/511* | (2006.01) |
| *A61F 13/515* | (2006.01) |
| *A61F 13/58* | (2006.01) |
| *B32B 38/00* | (2006.01) |
| *A61F 13/47* | (2006.01) |

(52) U.S. Cl.
CPC .... *A61F 13/49011* (2013.01); *A61F 13/4906* (2013.01); *A61F 13/51113* (2013.01); *A61F 13/51121* (2013.01); *A61F 13/515* (2013.01); *A61F 13/58* (2013.01); *A61F 2013/15861* (2013.01); *A61F 2013/1591* (2013.01); *A61F 2013/4708* (2013.01); *A61F 2013/49092* (2013.01)

(56) References Cited

U.S. PATENT DOCUMENTS

| | | | |
|---|---|---|---|
| 3,562,041 A | 2/1971 | Robertson |
| 3,733,238 A | 5/1973 | Long |
| 3,848,594 A | 11/1974 | Buell |
| 3,860,003 A | 1/1975 | Buell |
| 3,881,488 A | 5/1975 | Delanty et al. |
| 4,116,892 A | 9/1978 | Schwarz |
| 4,324,246 A | 4/1982 | Mullane et al. |
| 4,342,314 A | 8/1982 | Radel et al. |
| 4,463,045 A | 7/1984 | Ahr et al. |
| 4,515,595 A | 5/1985 | Kievit |
| 4,556,146 A | 12/1985 | Swanson et al. |
| 4,568,344 A | 2/1986 | Suzuki et al. |
| 4,589,876 A | 5/1986 | Van Tilburg |
| 4,610,678 A | 9/1986 | Weisman |
| 4,662,875 A | 5/1987 | Hirotsu |
| 4,673,402 A | 6/1987 | Weisman |
| 4,687,478 A | 8/1987 | Van Tillburg |
| 4,695,278 A | 9/1987 | Lawson |
| 4,704,115 A | 11/1987 | Buell |
| 4,795,454 A | 1/1989 | Dragoo |
| 4,795,510 A | 1/1989 | Wittrock et al. |
| 4,824,498 A | 4/1989 | Goodwin et al. |
| 4,834,735 A | 5/1989 | Alemany |
| 4,834,741 A | 5/1989 | Sabee |
| 4,846,815 A | 7/1989 | Scripps |
| 4,854,984 A | 8/1989 | Ball |
| 4,888,231 A | 12/1989 | Angstadt |
| 4,894,060 A | 1/1990 | Nestegard |
| 4,909,803 A | 3/1990 | Aziz |
| 4,940,464 A | 7/1990 | Van Gompel et al. |
| 4,946,527 A | 8/1990 | Battrell |
| 4,950,264 A | 8/1990 | Osborn, III |
| 5,009,653 A | 4/1991 | Osborn, III |
| 5,026,364 A | 6/1991 | Robertson |
| 5,092,861 A | 3/1992 | Nomura |
| 5,110,403 A | 5/1992 | Ehlert |

| | | | |
|---|---|---|---|
| 5,143,679 A | 9/1992 | Weber |
| 5,151,092 A | 9/1992 | Buell |
| 5,156,793 A | 10/1992 | Buell |
| 5,167,897 A | 12/1992 | Weber et al. |
| 5,192,606 A | 3/1993 | Proxmire |
| 5,221,274 A | 6/1993 | Buell |
| 5,242,436 A | 9/1993 | Weil |
| 5,246,433 A | 9/1993 | Hasse |
| 5,267,992 A | 12/1993 | Van Tilburg |
| 5,308,345 A | 5/1994 | Herrin |
| 5,360,420 A | 11/1994 | Cook et al. |
| 5,407,507 A | 4/1995 | Ball |
| 5,422,172 A | 6/1995 | Wu |
| 5,518,801 A | 5/1996 | Chappell et al. |
| 5,540,796 A | 7/1996 | Fries |
| 5,562,646 A | 10/1996 | Goldman et al. |
| 5,569,234 A | 10/1996 | Buell |
| 5,571,096 A | 11/1996 | Dobrin |
| 5,575,783 A | 11/1996 | Clear |
| 5,599,335 A | 2/1997 | Goldman et al. |
| 5,628,097 A | 5/1997 | Benson |
| 5,643,588 A | 7/1997 | Roe |
| 5,669,894 A | 9/1997 | Goldman et al. |
| 5,674,216 A | 10/1997 | Buell et al. |
| 5,693,037 A | 12/1997 | Lee et al. |
| 5,700,255 A | 12/1997 | Curro |
| 5,702,551 A | 12/1997 | Huber et al. |
| 5,735,840 A | 4/1998 | Kline |
| 5,827,259 A | 10/1998 | Laux |
| 5,897,545 A | 4/1999 | Kline |
| 5,904,675 A | 5/1999 | Laux |
| 5,916,661 A | 6/1999 | Benson |
| 5,928,212 A | 7/1999 | Kline |
| 5,957,908 A | 9/1999 | Kline |
| 5,961,997 A | 10/1999 | Swinehart |
| 5,968,025 A | 10/1999 | Roe |
| 5,993,433 A | 11/1999 | St. Louis |
| 6,004,893 A | 12/1999 | Van Tilburg |
| 6,010,491 A | 1/2000 | Roe et al. |
| 6,036,796 A | 3/2000 | Halbert |
| 6,051,094 A | 4/2000 | Melbye et al. |
| 6,107,537 A | 8/2000 | Elder |
| 6,107,539 A | 8/2000 | Palumbo |
| 6,118,041 A | 9/2000 | Roe et al. |
| 6,120,487 A | 9/2000 | Ashton |
| 6,120,489 A | 9/2000 | Johnson |
| 6,149,934 A | 11/2000 | Krzysik et al. |
| 6,153,209 A | 11/2000 | Vega et al. |
| 6,156,023 A | 12/2000 | Yoshioka |
| 6,238,683 B1 | 5/2001 | Burnett et al. |
| 6,248,097 B1 | 6/2001 | Beitz et al. |
| 6,248,195 B1 | 6/2001 | Schmitz |
| 6,251,097 B1 | 6/2001 | Kline |
| 6,316,524 B1 | 11/2001 | Corzani et al. |
| 6,369,290 B1 | 4/2002 | Glaug |
| 6,409,883 B1 | 6/2002 | Makolin |
| 6,410,129 B2 | 6/2002 | Zhang |
| 6,426,444 B2 | 7/2002 | Roe et al. |
| 6,432,098 B1 | 8/2002 | Kline |
| 6,454,095 B1 | 9/2002 | Brisebois |
| 6,506,185 B1 | 1/2003 | Sauer et al. |
| 6,508,641 B1 | 1/2003 | Kubik |
| 6,524,293 B1 | 2/2003 | Elsberg et al. |
| 6,545,197 B1 | 4/2003 | Muller et al. |
| 6,568,530 B2 | 5/2003 | Takahashi |
| 6,572,595 B1 | 6/2003 | Klemp |
| 6,586,652 B1 | 7/2003 | Roe et al. |
| 6,601,705 B2 | 8/2003 | Molina |
| 6,617,016 B2 | 9/2003 | Zhang et al. |
| 6,627,787 B1 | 9/2003 | Roe et al. |
| 6,645,330 B2 | 11/2003 | Pargass |
| 6,648,864 B2 | 11/2003 | Ronn |
| 6,669,618 B2 | 12/2003 | Reising |
| 6,699,228 B1 | 3/2004 | Chmielewski et al. |
| 6,790,798 B1 | 9/2004 | Suzuki et al. |
| 6,825,393 B2 | 11/2004 | Roe et al. |
| 6,830,800 B2 | 12/2004 | Curro |
| 6,861,571 B1 | 3/2005 | Roe et al. |
| 7,087,287 B2 | 8/2006 | Curro |

(56)                    References Cited

U.S. PATENT DOCUMENTS

| | | | |
|---|---|---|---|
| 7,371,302 | B2 | 5/2008 | Miyamoto et al. |
| 7,569,039 | B2 | 8/2009 | Matsuda |
| 7,785,309 | B2 | 8/2010 | Van Gompel et al. |
| 7,803,244 | B2 | 9/2010 | Siqueira |
| 7,824,594 | B2 | 11/2010 | Qureshi |
| 7,896,641 | B2 | 3/2011 | Qureshi |
| 8,062,572 | B2 | 11/2011 | Qureshi |
| 8,071,990 | B2 | 12/2011 | Bogner et al. |
| 8,118,801 | B2 | 2/2012 | Macura |
| 8,186,296 | B2 | 5/2012 | Brown et al. |
| 8,257,333 | B2 | 9/2012 | Hancock-cooke et al. |
| 8,395,012 | B2 | 3/2013 | Bacon et al. |
| 8,496,638 | B2 | 7/2013 | Lord et al. |
| 8,608,720 | B2 | 12/2013 | Erickson et al. |
| 8,662,706 | B2 | 3/2014 | Komatsu |
| 8,715,464 | B2 | 5/2014 | Young et al. |
| 8,778,127 | B2 | 7/2014 | Schneider et al. |
| 8,936,697 | B2 | 1/2015 | Scharpf et al. |
| 8,950,912 | B2 | 2/2015 | Corporation |
| 8,956,493 | B2 | 2/2015 | Tenorio et al. |
| 9,005,392 | B2 | 4/2015 | Schneider |
| 9,248,054 | B2 | 2/2016 | Brown et al. |
| 9,265,672 | B2 | 2/2016 | Brown et al. |
| 9,283,124 | B2 | 3/2016 | Hashimoto et al. |
| 9,295,590 | B2 | 3/2016 | Brown et al. |
| 9,429,304 | B2 | 8/2016 | Masuda et al. |
| 9,464,777 | B2 | 10/2016 | Boyce et al. |
| 9,468,569 | B2 | 10/2016 | Hancock-cooke et al. |
| 9,687,580 | B2 | 6/2017 | Schonbeck |
| 9,737,442 | B2 | 8/2017 | Findley |
| 9,738,002 | B2 | 8/2017 | Schneider et al. |
| 9,913,871 | B2 | 3/2018 | Ellington et al. |
| 9,962,297 | B2 | 5/2018 | Eckstein |
| 10,052,237 | B2 | 8/2018 | Galie |
| 10,159,610 | B2 | 12/2018 | Barnes |
| 10,470,943 | B2 | 11/2019 | Jang |
| 11,096,836 | B2 | 8/2021 | Bishop et al. |
| 11,369,526 | B2 | 6/2022 | Matsui et al. |
| 11,554,055 | B2 | 1/2023 | Bishop et al. |
| 12,115,042 | B2 * | 10/2024 | Schneider ......... A61F 13/15723 |
| 2002/0064639 | A1 | 5/2002 | Rearick et al. |
| 2002/0129740 | A1 | 9/2002 | Kato et al. |
| 2002/0165170 | A1 | 11/2002 | Wilson et al. |
| 2002/0173768 | A1 | 11/2002 | Elsberg |
| 2003/0121380 | A1 | 7/2003 | Cowell |
| 2003/0154904 | A1 | 8/2003 | Klofta et al. |
| 2003/0187414 | A1 | 10/2003 | Reiss et al. |
| 2003/0233082 | A1 | 12/2003 | Kline |
| 2004/0097895 | A1 | 5/2004 | Busam et al. |
| 2004/0122413 | A1 | 6/2004 | Roessler |
| 2004/0158212 | A1 | 8/2004 | Ponomarenko et al. |
| 2004/0196734 | A1 | 10/2004 | Mehta et al. |
| 2005/0096616 | A1 | 5/2005 | Arora et al. |
| 2005/0107764 | A1 | 5/2005 | Matsuda et al. |
| 2005/0171498 | A1 | 8/2005 | Reiss et al. |
| 2005/0217812 | A1 | 10/2005 | Stoyanov et al. |
| 2006/0094320 | A1 | 5/2006 | Chen et al. |
| 2006/0129115 | A1 | 6/2006 | Visscher |
| 2006/0167434 | A1 | 7/2006 | Ashton et al. |
| 2006/0196796 | A1 | 9/2006 | Motsch et al. |
| 2006/0264862 | A1 | 11/2006 | Yoshida et al. |
| 2006/0264863 | A1 | 11/2006 | Blyth |
| 2006/0287637 | A1 | 12/2006 | Lam |
| 2007/0032772 | A1 | 2/2007 | Ehrnsperger |
| 2007/0078427 | A1 | 4/2007 | Raycheck |
| 2007/0093769 | A1 | 4/2007 | Kline |
| 2007/0149937 | A1 | 6/2007 | Reiss et al. |
| 2007/0219521 | A1 | 9/2007 | Hird |
| 2007/0287980 | A1 | 12/2007 | Kline et al. |
| 2008/0099360 | A1 | 5/2008 | Smith |
| 2008/0250681 | A1 | 10/2008 | Jackson |
| 2008/0269704 | A1 | 10/2008 | Hansson et al. |
| 2009/0054864 | A1 | 2/2009 | Lira et al. |
| 2009/0149827 | A1 | 6/2009 | Mlinar et al. |
| 2009/0155325 | A1 | 6/2009 | Magin et al. |
| 2009/0157034 | A1 | 6/2009 | Mattingly et al. |
| 2009/0204090 | A1 | 8/2009 | Dennis et al. |
| 2009/0294044 | A1 | 12/2009 | Gill |
| 2009/0312730 | A1 | 12/2009 | LaVon et al. |
| 2010/0181223 | A1 | 7/2010 | Warren |
| 2010/0221496 | A1 | 9/2010 | De Jong |
| 2010/0230857 | A1 | 9/2010 | Muhs et al. |
| 2010/0305532 | A1 | 12/2010 | Ashton et al. |
| 2011/0040273 | A1 | 2/2011 | Sablone |
| 2011/0046594 | A1 | 2/2011 | Sablone |
| 2011/0073513 | A1 | 3/2011 | Weisman et al. |
| 2011/0139657 | A1 | 6/2011 | Hird |
| 2011/0139658 | A1 | 6/2011 | Hird |
| 2011/0139659 | A1 | 6/2011 | Hird |
| 2011/0139662 | A1 | 6/2011 | Hird |
| 2011/0152812 | A1 | 6/2011 | Hird |
| 2011/0215017 | A1 | 9/2011 | Coulter et al. |
| 2011/0315585 | A1 | 12/2011 | Meyer et al. |
| 2011/0319849 | A1 | 12/2011 | Collias et al. |
| 2012/0061015 | A1 | 3/2012 | Lavon et al. |
| 2012/0061016 | A1 | 3/2012 | Lavon et al. |
| 2012/0143165 | A1 | 6/2012 | Macura |
| 2012/0206265 | A1 | 8/2012 | Solazzo et al. |
| 2012/0276341 | A1 | 11/2012 | Lake |
| 2012/0277703 | A1 | 11/2012 | Rhein |
| 2012/0277713 | A1 | 11/2012 | Raycheck |
| 2013/0018339 | A1 | 1/2013 | Kaiser et al. |
| 2013/0072887 | A1 | 3/2013 | Lavon |
| 2013/0126071 | A1 | 5/2013 | Shin et al. |
| 2013/0211356 | A1 | 8/2013 | Nishikawa et al. |
| 2013/0255861 | A1 | 10/2013 | Schneider |
| 2013/0255862 | A1 | 10/2013 | Schneider et al. |
| 2013/0255863 | A1 | 10/2013 | Lavon et al. |
| 2013/0255864 | A1 | 10/2013 | Schneider et al. |
| 2013/0255865 | A1 | 10/2013 | Brown et al. |
| 2013/0274697 | A1 | 10/2013 | Godlewski |
| 2013/0306226 | A1 | 11/2013 | Zink |
| 2013/0313149 | A1 | 11/2013 | Hird et al. |
| 2014/0005621 | A1 | 1/2014 | Roe |
| 2014/0039422 | A1 | 2/2014 | Scott |
| 2014/0079919 | A1 | 3/2014 | Bunnelle |
| 2014/0093697 | A1 | 4/2014 | Perry et al. |
| 2014/0148773 | A1 | 5/2014 | Brown |
| 2014/0272370 | A1 | 9/2014 | Broyles |
| 2014/0276512 | A1 | 9/2014 | Cheng et al. |
| 2014/0350504 | A1 | 11/2014 | Coenen |
| 2014/0352090 | A1 | 12/2014 | Schuchter |
| 2014/0371700 | A1 | 12/2014 | Patel et al. |
| 2015/0283003 | A1 | 10/2015 | Rosati |
| 2015/0366724 | A1 | 12/2015 | Fukuzawa et al. |
| 2015/0374561 | A1 | 12/2015 | Hubbard, Jr. et al. |
| 2016/0101003 | A1 | 4/2016 | Jennewein et al. |
| 2016/0206774 | A1 | 7/2016 | Hird |
| 2016/0270973 | A1 | 9/2016 | Surushe et al. |
| 2016/0270979 | A1 | 9/2016 | Raycheck et al. |
| 2016/0270980 | A1 | 9/2016 | Raycheck et al. |
| 2016/0350828 | A1 | 12/2016 | Schmidt et al. |
| 2017/0000658 | A1 | 1/2017 | Chatterjee |
| 2017/0056253 | A1 | 3/2017 | Chester et al. |
| 2017/0246052 | A1 | 8/2017 | Ludwig |
| 2017/0252229 | A1 | 9/2017 | Bonelli |
| 2017/0290712 | A1 | 10/2017 | Findley |
| 2017/0296399 | A1 | 10/2017 | Kline et al. |
| 2017/0313034 | A1 | 11/2017 | Takeda et al. |
| 2017/0319399 | A1 | 11/2017 | Desai et al. |
| 2017/0333261 | A1 | 11/2017 | Chatterjee |
| 2017/0333262 | A1 | 11/2017 | Chatterjee et al. |
| 2018/0042777 | A1 | 2/2018 | Dalal |
| 2018/0042778 | A1 | 2/2018 | Lenser |
| 2018/0042779 | A1 | 2/2018 | Lenser |
| 2018/0042780 | A1 | 2/2018 | Lenser |
| 2018/0042785 | A1 | 2/2018 | Dalal |
| 2018/0042786 | A1 | 2/2018 | Mueller et al. |
| 2018/0042787 | A1 | 2/2018 | Lenser |
| 2018/0055698 | A1 | 3/2018 | Bishop et al. |
| 2018/0071155 | A1 | 3/2018 | Bishop |
| 2018/0140469 | A1 | 5/2018 | Kane et al. |
| 2018/0169964 | A1 | 6/2018 | Schneider |
| 2018/0199743 | A1 | 7/2018 | Kajak |

(56)                    References Cited

U.S. PATENT DOCUMENTS

| | | |
|---|---|---|
| 2018/0250171 A1 | 9/2018 | Bäck et al. |
| 2018/0256419 A1 | 9/2018 | Mcgilloway et al. |
| 2018/0271716 A1 | 9/2018 | Dalal |
| 2018/0360739 A1 | 12/2018 | Lorenz et al. |
| 2018/0369091 A1 | 12/2018 | Avshalomov |
| 2019/0010258 A1 | 1/2019 | Mitchell et al. |
| 2019/0070042 A1 | 3/2019 | Beck |
| 2019/0083325 A1 | 3/2019 | Mccormick |
| 2019/0083331 A1 | 3/2019 | Barnes |
| 2019/0175417 A1 | 6/2019 | Graham |
| 2020/0038256 A1 | 2/2020 | Jang et al. |
| 2020/0054496 A1 | 2/2020 | Mccormick et al. |
| 2020/0054497 A1 | 2/2020 | Mccormick et al. |
| 2020/0078230 A1 | 3/2020 | Mccormick et al. |
| 2020/0093652 A1 | 3/2020 | Mccormick et al. |
| 2020/0093653 A1 | 3/2020 | Mccormick et al. |
| 2020/0121519 A1 | 4/2020 | Mccormick et al. |
| 2020/0155372 A1 | 5/2020 | Kleuskens et al. |
| 2020/0163812 A1 | 5/2020 | Zuleger et al. |
| 2020/0197560 A1 | 6/2020 | Buchalter |
| 2020/0375807 A1 | 12/2020 | Schneider et al. |
| 2020/0375815 A1 | 12/2020 | Raycheck et al. |
| 2020/0375816 A1 | 12/2020 | Mccormick et al. |
| 2021/0128366 A1 | 5/2021 | Schneider et al. |
| 2021/0128369 A1 | 5/2021 | Raycheck et al. |
| 2021/0282981 A1 | 9/2021 | Matsui et al. |
| 2021/0346211 A1 | 11/2021 | Kilbacak et al. |
| 2021/0346213 A1 | 11/2021 | Kilbacak et al. |
| 2023/0310229 A1 | 10/2023 | Williams et al. |

FOREIGN PATENT DOCUMENTS

| | | |
|---|---|---|
| CN | 1328438 A | 12/2001 |
| CN | 101327156 A | 12/2008 |
| CN | 101389237 A | 3/2009 |
| CN | 106038076 A | 10/2016 |
| CN | 106456410 A | 2/2017 |
| CN | 107405227 A | 11/2017 |
| CN | 107809989 A | 3/2018 |
| CN | 108472171 A | 8/2018 |
| CN | 109069313 A | 12/2018 |
| CN | 109069315 A | 12/2018 |
| CN | 114025727 A | 2/2022 |
| EP | 2260813 B1 | 7/2015 |
| EP | 3538046 A1 | 9/2019 |
| JP | S63211303 A | 9/1988 |
| JP | 2001095838 A | 4/2001 |
| JP | 2002232009 A | 8/2002 |
| JP | 2002541918 A | 12/2002 |
| JP | 2008074327 A | 4/2008 |
| JP | 2008113684 A | 5/2008 |
| JP | 2008113685 A | 5/2008 |
| JP | 2010269029 A | 12/2010 |
| JP | 2011010822 A | 1/2011 |
| JP | 2011062226 A | 3/2011 |
| JP | 2012243462 A | 12/2012 |
| JP | 2013164937 A | 8/2013 |
| JP | 2013168434 A | 8/2013 |
| JP | 2013180171 A | 9/2013 |
| JP | 2016112341 A | 6/2016 |
| JP | 2016182169 A | 10/2016 |
| JP | 2017060635 A | 3/2017 |
| JP | 2020000531 A | 1/2020 |
| RU | 24771 U1 | 8/2002 |
| WO | 9511650 A1 | 5/1995 |
| WO | 9524173 A2 | 9/1995 |
| WO | 9632913 A1 | 10/1996 |
| WO | 9720532 A1 | 6/1997 |
| WO | 9920215 A1 | 4/1999 |
| WO | 0007534 A1 | 2/2000 |
| WO | 2007106929 A1 | 9/2007 |
| WO | 2009012284 A1 | 1/2009 |
| WO | 2012149238 A2 | 11/2012 |
| WO | 2013002691 A1 | 1/2013 |
| WO | 2013173291 A1 | 11/2013 |
| WO | 2014103464 A1 | 7/2014 |
| WO | 2014150303 A1 | 9/2014 |
| WO | 2016023016 A1 | 2/2016 |
| WO | 2017118612 A1 | 7/2017 |
| WO | 2017124092 A1 | 7/2017 |
| WO | 2018089088 A1 | 5/2018 |
| WO | 2020003160 A2 | 1/2020 |
| WO | 2020004476 A1 | 1/2020 |
| WO | 2020004499 A1 | 1/2020 |
| WO | 2020115916 A1 | 6/2020 |
| WO | 2020116554 A1 | 6/2020 |
| WO | 2020116592 A1 | 6/2020 |
| WO | 2020116593 A1 | 6/2020 |
| WO | 2020116595 A1 | 6/2020 |

OTHER PUBLICATIONS

PCT Search Report and Written Opinion for PCT/US2020/030893 dated Jul. 27, 2020, 12 pages.
PCT Search Report and Written Opinion for PCT/US2020/070568 dated Dec. 8, 2020, 13 pages.
EP Search Report and Opinion for 23199743.8 dated Dec. 20, 2023, 09 pages.
All Office Actions, U.S. Appl. No. 16/864,267, filed May 1, 2020.
All Office Actions, U.S. Appl. No. 16/864,292, filed May 1, 2020.
All Office Actions, U.S. Appl. No. 16/885,622, filed May 28, 2020.
All Office Actions, U.S. Appl. No. 17/029,211, filed Sep. 23, 2020.
All Office Actions, U.S. Appl. No. 17/029,486, filed Sep. 23, 2020.
All Office Actions; U.S. Appl. No. 17/242,376, filed Apr. 28, 2021.
All Office Actions; U.S. Appl. No. 18/126,534, filed Mar. 27, 2023.
All Office Actions; U.S. Appl. No. 18/493,083, filed Oct. 24, 2023.
All Office Actions; U.S. Appl. No. 18/815,950, filed Aug. 27, 2024.
Epsilon, Water Soluble Dyes/Solvent Green 7 and Corresponding Material Safety Data Sheet , Jul. 15, 2013, 5 pages.
Unpublished U.S. Appl. No. 18/815,950, filed Aug. 27, 2024, Uwe Schneider et al.
All Office Actions; U.S. Appl. No. 19/252,063, filed Jun. 27, 2025.
Unpublished U.S. Appl. No. 19/252,063, filed Jun. 27, 2025, to Sally Lin Kilbacak et al.

* cited by examiner

METHOD AND APPARATUS FOR BONDING ELASTIC PARTS UNDER TENSION TO AN ADVANCING CARRIER

CROSS REFERENCE TO RELATED APPLICATIONS

This application is a continuation of U.S. patent application Ser. No. 16/864,267, filed on May 1, 2020, now granted U.S. Pat. No. 12,115,042, issued Oct. 15, 2024, which claims the benefit of U.S. Provisional Patent Application Ser. No. 62/930,181, filed on Nov. 4, 2019; U.S. Provisional Patent Application No. 62/855,001, filed on May 31, 2019; U.S. Provisional Patent Application No. 62/930,198, filed on Nov. 4, 2019; and U.S. Provisional Patent Application No. 62/930,808, filed on Nov. 5, 2019, which are all hereby incorporated by reference herein.

FIELD OF THE INVENTION

The present disclosure relates to methods and apparatuses for manufacturing absorbent articles, and more particularly, to apparatuses and methods for stretching, transferring, and bonding elastic parts to an advancing carrier during the assembly of absorbent articles.

BACKGROUND OF THE INVENTION

Along an assembly line, various types of articles, such as for example, diapers and other absorbent articles, may be assembled by adding components to and/or otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. In some cases, individual components created from an advancing web or webs are combined with other individual components created from other advancing webs. Webs of material and component parts used to manufacture diapers may include: backsheets, topsheets, leg cuffs, waist bands, absorbent core components, front and/or back ears, fastening components, and various types of elastic webs and parts such as leg elastics, barrier leg cuff elastics, stretch side panels, and waist elastics. Once the desired component parts are assembled, the advancing web(s) and component parts are subjected to a final knife cut to separate the web(s) into discrete diapers or other absorbent articles.

Some absorbent articles have components that include elastic parts, such as for example, waistbands. In some configurations, waistbands may be provided as a single layer of elastic material, such as an elastic film. In some configurations, the waistbands may be provided as an elastic laminate that may include elastic material bonded to one or more substrates such as nonwovens, wherein the elastic material may include an elastic film and/or elastic strands. In some assembly operations, the waistbands are joined to an advancing carrier web, such as a continuous topsheet or backsheet web, while the waistbands are in a stretched condition. As such, when the waistbands relax, the carrier web gathers to form corrugations. The resulting laminate is stretchable to the extent that the corrugations allow the waistband to elongate.

When manufacturing absorbent articles, the waistband may be provided as a continuous length of waistband material that may be stretched; cut into discrete waistbands; and bonded with the advancing carrier web while the waistband is in a stretched state. In addition, the carrier web may be advanced in a machine direction and the waistband may be applied to the carrier web such that direction of stretch of the waistband is oriented in a cross direction. For example, some manufacturers may stretch a continuous waistband material in a machine direction and cut the continuous waistband material into stretched discrete waistbands. The stretched discrete waistbands may be turned 90 degrees before placement on and bonding to the advancing carrier web such that direction of stretch is oriented in the cross direction with respect to the carrier web. However, such assembly operations involving the handling and bonding of discrete waistbands in a stretched state can present various challenges.

For example, with reference to a waistband and topsheet bonding operation as an example illustration, adhesive may be applied to either or both the discrete waistband and the topsheet. When applying adhesive to the discrete waistband prior to combining with the topsheet, applied adhesive may migrate from the waistband and contaminate material handling equipment, such as knives, drums, and conveyance devices utilized to place the waistband on the topsheet. Such contaminating adhesive may also migrate to other substrates and components of the assembled article. Instead of applying adhesive to the waistband, adhesive may be applied to the topsheet before combining with the waistband. As such, the adhesive may be applied to the topsheet in discrete patches that are sized to correlate or match with the size of the waistband. Such an operation requires very precise placement of the waistband on the discrete patches of adhesive. Misplacement of the waistbands on the adhesive may lead to portions of the waistbands being unbonded and may also lead to areas of exposed adhesive. In turn, exposed adhesive that remains tacky can act to unintentionally bond other components together. For example, in subsequent assembly operations, the combined waistband and topsheet may be combined with other advancing substrates and/or components to create discrete absorbent articles that are folded and packaged. As such, the absorbent article may become bonded to itself in the folded configuration.

In an attempt to avoid the above described negative affects resulting from exposed tacky adhesive in an assembled product, adhesives may be applied in areas that are smaller than the discrete part to be bonded. For example, adhesive may be applied to only central portions of discrete waistband before combining with a topsheet. In another scenario, adhesive may be applied to the topsheet in discrete patches that are relatively smaller than the size of the waistband. In turn, only the central region of a waistband may be bonded with the topsheet. As such, perimeter edges of the waistband may remain unbonded and loose. Such unbonded edges may be aesthetically unpleasing and may lead to undesired tearing and/or separation of the waistband during product use.

In addition, difficulties associated with precisely placing the discrete waistband in a desired location may be exacerbated in assembly processes that require turning the discrete waistbands 90 degrees before combining with an advancing topsheet. Manufacturers may also encounter various difficulties associated with close coupled handovers of stretched waistbands between conveyance devices while maintaining the stretched condition of the waistbands. Further, components of the apparatuses associated with waistband application processes may be relatively inflexible with respect to making absorbent articles of different sizes. For example, existing assembly operations may be configured to place waistbands at fixed pitch distances that cannot be altered without changing several apparatus components when needed to make articles of different sizes that require changes in pitch distances.

Consequently, it would be beneficial to provide methods and apparatuses for bonding waistbands to carrier webs while helping to increase the size of bonded areas and reducing the chances of having exposed adhesives during subsequent assembly operations; providing flexibility to accommodate desired speed and/or pitch changes; eliminating the need for 90 degree turn operations of stretched waistbands; and/or improving abilities to transfer stretched waistbands between close coupled conveyance devices while helping to maintain the stretched condition of the waistbands.

SUMMARY OF THE INVENTION

In one form, a method of assembling absorbent articles comprises steps of: advancing a carrier substrate at a first speed in a machine direction, the carrier substrate comprising a first longitudinal edge and a second longitudinal edge separated from the first longitudinal edge in a cross direction; advancing a continuous elastic substrate at a second speed in the machine direction, the continuous elastic substrate comprising a first longitudinal edge and a second longitudinal edge separated from the first longitudinal edge in the cross direction, wherein the continuous elastic substrate is stretchable in the cross direction; cutting an elastic part from the continuous elastic substrate, the elastic part comprising a first end region and a second end region separated from the first end region in the cross direction by a central region; changing a speed of the elastic part from the second speed to the first speed; stretching the central region of the discrete elastic part in the cross direction; positioning the elastic part on the carrier substrate such that the stretched central region extends in the cross direction between the first and second longitudinal edges of the carrier substrate; adhesively bonding the stretched central region of the elastic part with the carrier substrate; and mechanically bonding the first end region and the second end region of the elastic part with the carrier substrate.

In another form, a method of assembling absorbent articles comprises steps of: providing an elastic part comprising a first surface and an opposing second surface, the elastic part further comprising a first end region and a second end region separated from the first end region in a cross direction by a central region; providing a zone of adhesive positioned on the second surface of the elastic part; advancing the elastic part in a machine direction on a first roll, wherein the second surface is facing radially outward; transferring the first end region and the second end region of the elastic part from the first roll to a rotatable transfer device, wherein the second surface of the elastic part is facing radially inward; stretching the central region of the elastic part in the cross direction while rotating the transfer device; transferring the stretched elastic part to a second roll, wherein the second surface of the elastic part is facing radially outward; advancing a carrier substrate adjacent the second roll, the carrier substrate comprising a first longitudinal edge and a second longitudinal edge separated from the first longitudinal side in the cross direction; advancing the elastic part from the second roll to the carrier substrate such that the stretched central region extends in the cross direction between the first and second longitudinal edges of the carrier substrate; adhesively bonding the stretched central region of the elastic part with the carrier substrate; and mechanically bonding the first end region and the second end region of the elastic part with the carrier substrate.

In yet another form, a method of assembling absorbent articles comprises steps of: advancing a continuous elastic substrate in a machine direction between a rotating knife roll and anvil roll; cutting an elastic part from the continuous elastic substrate, the elastic part comprising a first end region and a second end region separated from the first end region in the cross direction by a central region; advancing the elastic part in a machine direction on the knife roll or the anvil roll; transferring the first end region of the elastic part onto a first canted disk and transferring the second end region of the elastic part onto a second canted disk; stretching the central region of the elastic part in the cross direction by rotating the first canted disk and the second canted disk; transferring the stretched elastic part from the first and second canted disks to a rotating pattern roll; and advancing a carrier substrate adjacent the pattern roll; and bonding the stretched elastic part with the carrier substrate while the stretched elastic part is positioned between the carrier substrate and the pattern roll.

In still another form, a method of assembling absorbent articles comprises steps of: advancing a continuous elastic substrate in a machine direction, the continuous elastic substrate comprising a first surface and an opposing second surface, the continuous elastic substrate comprising a first longitudinal edge and a second longitudinal edge separated from the first longitudinal edge in a cross direction to define a first width, wherein the continuous elastic substrate is stretchable in the cross direction and comprises corrugations oriented to define corrugation lines extending in the machine direction; applying adhesive to corrugations on the first surface of the continuous elastic substrate, wherein the adhesive extends in the cross direction for a second width, wherein the second width is less than the first width; cutting an elastic part from the continuous elastic substrate, the elastic part comprising a first end region and a second end region separated from the first end region in the cross direction by a central region, wherein a zone of adhesive is positioned on the central region and not the first and second end regions; separating the zone of adhesive into individual stripes of adhesive by stretching the central region of the elastic part in the cross direction; adhesively bonding the stretched central region of the elastic part to a carrier substrate with the stripes of adhesive; and mechanically bonding the first end region and the second end region of the elastic part with the carrier substrate.

In still another form, a method of assembling absorbent articles comprises steps of: advancing the elastic part in a machine direction on a first roll; providing a first disk and a second disk, wherein the first disk and the second disk are canted relative to each other, and wherein the first disk and the second disk each comprise an outer rim comprising a pick-up surface and a drop-off surface, wherein the pick-up surface is angularly offset from the drop-off surface; transferring the first end region of the elastic part from the first roll onto pick-up surface of the first disk and transferring the second end region of the elastic part from the second roll onto the pick-up surface of the second disk; stretching the central region of the elastic part in the cross direction by rotating the first disk and the second disk; transferring the first end region of the elastic part from the drop-off surface of the first disk to a second roll and transferring the second end region of the elastic part from the drop-off surface of the second disk to the second roll; and advancing a carrier substrate adjacent the second roll; and bonding the stretched elastic part with the carrier substrate while the stretched elastic part is positioned between the carrier substrate and the second roll.

BRIEF DESCRIPTION OF THE DRAWINGS

FIG. 4A1 is a view of the continuous elastic substrate taken along section 4A1-4A1 in FIG. 4A.

FIG. 6A1 is a view of the discrete elastic part taken along section 6A1-6A1 in FIG. 6A.

FIG. 10A1 is a view of the stretched discrete elastic part taken along section 10A1-10A1 in FIG. 10A.

DETAILED DESCRIPTION OF THE INVENTION

Figure 1A:
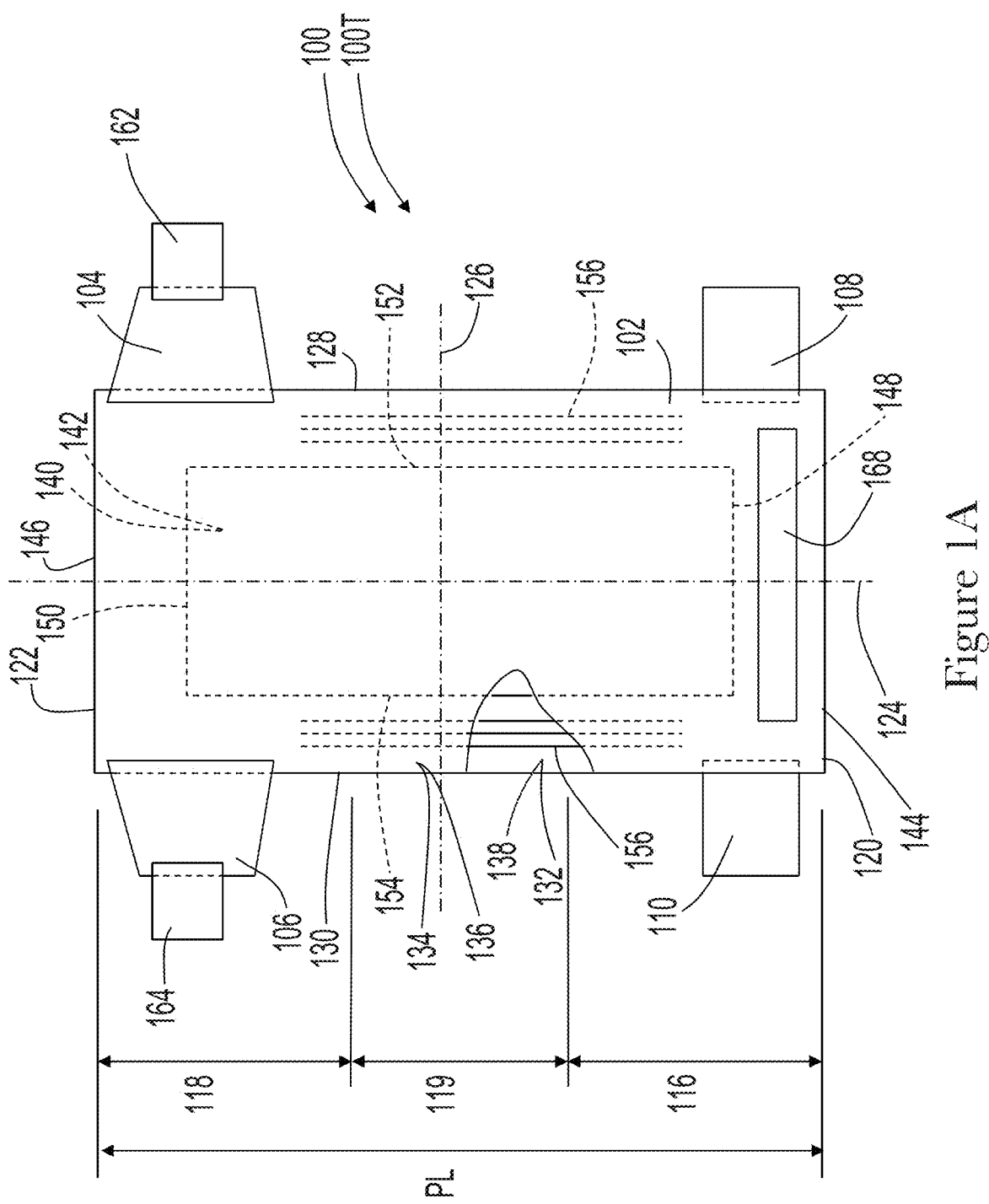
FIG. 1A is a partially cut away plan view of an absorbent article in the form of a taped diaper that may include one or more substrates bonded in accordance with the present disclosure with the portion of the diaper that faces away from a wearer oriented towards the viewer.

The following term explanations may be useful in understanding the present disclosure: "Absorbent article" is used herein to refer to consumer products whose primary function is to absorb and retain soils and wastes. Absorbent articles can comprise sanitary napkins, tampons, panty liners, interlabial devices, wound dressings, wipes, disposable diapers including taped diapers and diaper pants, inserts for diapers with a reusable outer cover, adult incontinent diapers, adult incontinent pads, and adult incontinent pants. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

The term "feminine hygiene articles" refers to disposable absorbent articles used by women for catamenial protection. Such feminine hygiene articles may include sanitary napkins, tampons, interlabial products, incontinence devices, and pantiliners. Non-limiting examples of panty liners and sanitary napkins include those disclosed in U.S. Pat. Nos. 4,324,246; 4,463,045; 4,342,314; 4,556,146; 4,589,876; 4,687,478; 4,950,264; 5,009,653; 5,267,992; and 6,004,893, which are all incorporated by reference herein.

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force.

"Consolidation," "consolidating," and "consolidated" refers to a material undergoing a reduction in elongation from a first stretched length to a second stretched length that is less than the first stretched length and greater than zero.

"Relaxed state" defines a length of material when not stretched by an applied force.

In the context of the present description, an elongation of 0% refers to a material in relaxed state having a relaxed length of L, and elongation of 150% represents 2.5× the relaxed length, L, of the material. For example, an elastic film having a relaxed length of 100 millimeters would have a length of 250 millimeters at 150% elongation. And an elastic film having a relaxed length of 100 millimeters would have a length of 180 millimeters at 80% elongation.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. In some configurations, a nonwoven may comprise a polyolefin based nonwoven, including but not limited to nonwovens having polypropylene fibers and/or polyethylene fibers and/or bicomponent fibers comprising a polyolefin. Nonlimiting examples of suitable fibers include spunbond, spunlaid, meltblown, spunmelt, solvent-spun, electrospun, carded, film fibrillated, melt-film fibrillated, air-laid, dry-laid, wet-laid staple fibers, and other nonwoven web materials formed in part or in whole of polymer fibers as known in the art, and workable combinations thereof. Nonwovens do not have a woven or knitted filament pattern. It is to be appreciated that nonwovens having various basis weights can be used in accordance with the methods herein. For example, some nonwovens may have a basis weight of at least about 8 gsm, 12 gsm, 16 gsm, 20 gsm, 25 gsm, 30 gsm, 40 gsm, or 65 gsm. Some nonwovens may have basis weight of about 8 gsm to about 65 gsm, specifically reciting all 1 gsm increments within the above-recited ranges and all ranges formed therein or thereby.

It is to be appreciated that films having various basis weights can be used in accordance with the methods herein. For example, some films may have a basis weight of at least about 8 gsm, 12 gsm, 16 gsm, 20 gsm, 25 gsm, 30 gsm, 40 gsm, or 60 gsm. Some films may have basis weight of about 5 gsm to about 150 gsm, specifically reciting all 1 gsm increments within the above-recited ranges and all ranges formed therein or thereby.

It is to be appreciated that elastic films discussed herein may comprise various materials and/or components. Some elastomeric compositions may comprise thermoplastic elastomers selected from the group consisting of Styrenic block copolymers, poly-esters, polyurethanes, polyether amides, and combinations thereof. Suitable styrenic block copolymers may be diblock, triblock, tetrablock, or other multiblock copolymers having at least one styrenic block. Exemplary styrenic block copolymers include styrene-butadiene-styrene, styrene-isoprene-styrene, styrene-ethylene/butylenes-styrene, styrene-ethylene/propylene-styrene, and the like. Commercially available styrenic block copolymers include KRATON (styrenic block copolymer; available from the Kraton Chemical Company, Houston, TX), SEPTON (styrenic block copolymer; available from Kuraray America, Inc., New York, NY), VECTOR (styrenic block copolymer; available from TSRC Dexco Chemical Company, Houston, TX) can be used. Additional commercially available elastomers include ESTANE (polyurethane; available from Lubrizol, Inc, Ohio), PEBAX (polyether block amide; available from Arkema Chemicals, Philadelphia, PA), and HYTREL (polyester; available from DuPont, Wilmington, DE).

Semi-crystalline, or metallocene polyolefins may be used in disposable absorbent products. The polyolefin elastomer materials herein may include, but are not limited to, any polymers or copolymers of polyolefins such as polyethylene and polypropylene. Examples of elastomeric polypropylenes include an elastic random poly(propylene/olefin) copolymer, an isotactic polypropylene containing stereo-irregularity, an isotactic/atactic polypropylene block copolymer, an isotactic polypropylene/random poly(propylene/olefin) copolymer block copolymer, a stereoblock elastomeric polypropylene, a syndiotactic polypropylene block poly(ethylene-co-propylene) block syndiotactic polypropylene triblock copolymer, an isotactic polypropylene block regioirregular polypropylene block isotactic polypropylene triblock copolymer, a polyethylene random (ethylene/olefin) copolymer block copolymer, a reactor blend polypropylene, a very low density polypropylene (or, equivalently, ultra low density polypropylene), a metallocene polypropylene, and blends or combinations thereof. Some homopolyolefins and random copolymers, as well as blends of such random copolymers, known by tradenames Vistamaxx™ available from ExxonMobil and VERSIFY™ from Dow, tend to show elastic performance. In some embodiments, two or more elastomers may be blended to achieve the desired elastic performance. For example, Styrenic block copolymer can be blended with polyolefin based elastomers, or polypropylene based elastomer can be blended with other polyolefin based elastomers.

Components of the disposable absorbent articles (i.e., diaper, disposable pant, adult incontinence article, sanitary napkin, pantiliner, etc.) described in this specification can at least partially be comprised of bio-sourced content as described in US 2007/0219521A1 Hird et al published on Sep. 20, 2007, US 2011/0139658A1 Hird et al published on Jun. 16, 2011, US 2011/0139657A1 Hird et al published on Jun. 16, 2011, US 2011/0152812A1 Hird et al published on Jun. 23, 2011, US 2011/0139662A1 Hird et al published on Jun. 16, 2011, and US 2011/0139659A1 Hird et al published on Jun. 16, 2011. These components include, but are not limited to, topsheet nonwovens, backsheet films, backsheet nonwovens, side panel nonwovens, barrier leg cuff nonwovens, super absorbent, nonwoven acquisition layers, core wrap nonwovens, adhesives, fastener hooks, and fastener landing zone nonwovens and film bases. In at least one embodiment, a disposable absorbent article component comprises a bio-based content value from about 10% to about 100% using ASTM D6866-10, method B, in another embodiment, from about 25% to about 75%, and in yet another embodiment, from about 50% to about 60% using ASTM D6866-10, method B. In order to apply the methodology of ASTM D6866-10 to determine the bio-based content of any disposable absorbent article component, a representative sample of the disposable absorbent article component must be obtained for testing. In at least one embodiment, the disposable absorbent article component can be ground into particulates less than about 20 mesh using known grinding methods (e.g., Wiley® mill), and a representative sample of suitable mass taken from the randomly mixed particles.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

Aspects of the present disclosure relate to methods and apparatuses for bonding substrates used in absorbent articles, and in particular, methods and apparatuses for stretching, transferring, and bonding elastic parts under tension to an advancing carrier substrate during the assembly of absorbent articles. With regard to the assembly processes described herein, a continuous carrier substrate may be advanced in a machine direction at a first speed, the carrier substrate comprising a first longitudinal edge and a second longitudinal edge separated from the first longitudinal side in a cross direction. A continuous elastic substrate may also be advanced in the machine direction at a second speed with at least one direction of stretch extending in the cross direction, wherein the second speed is slower than the first speed. A discrete elastic part is separated from the continuous elastic substrate, wherein the discrete elastic part comprises a first end region and a second end region separated from the first end region in the cross direction by a central region. The speed of the discrete elastic part is changed from the second speed to the first speed, and the central region of the discrete elastic part is stretched in the cross direction. The discrete elastic part is bonded with the continuous carrier substrate such that the stretched central region extends in the cross direction between the first and second longitudinal edges of the continuous carrier substrate.

As discussed in more detail below, the discrete elastic parts are cut from a continuous elastic substrate having a direction of stretch in the cross direction, which eliminates the necessity of a 90 degree turn operations of stretched elastic parts before bonding with the carrier substrate. The methods and apparatuses herein also provide the ability to bond the discrete elastic part with the carrier substrate with adhesive and/or mechanical bonds. In some configurations, adhesive may be applied so as to help maximize bonded areas between the elastic part and the carrier substrate while mechanical bonds may also be used to help reduce perimeter edges of the elastic part that may otherwise remain unbonded and loose. Consequently arranged conveying components of the apparatus may also be configured with intermeshing nubs and bonding elements and/or contoured outer rims that help improve abilities to transfer of discrete elastic parts while maintaining the elastic parts in a stretched condition. In addition, conveying components may also be configured with variable rotational velocities that help provide operational flexibility by reducing the necessity to change components to accommodate desired changes in speeds and/or pitching in manufacturing operations.

It is to be appreciated that the systems and methods disclosed herein are applicable to work with various types of converting processes and/or machines, such as for example, absorbent article manufacturing and assembly processes. The methods and apparatuses are discussed below in the context of manufacturing diapers that may be configured as taped diapers or pant diapers.

The term "taped diaper" (also referred to as "open diaper") refers to disposable absorbent articles having an initial front waist region and an initial back waist region that are not fastened, pre-fastened, or connected to each other as packaged, prior to being applied to the wearer. A taped diaper may be folded about the lateral centerline with the interior of one waist region in surface to surface contact with the interior of the opposing waist region without fastening or joining the waist regions together. Example taped diapers are disclosed in various suitable configurations U.S. Pat. Nos. 5,167,897, 5,360,420, 5,599,335, 5,643,588, 5,674, 216, 5,702,551, 5,968,025, 6,107,537, 6,118,041, 6,153,209, 6,410,129, 6,426,444, 6,586,652, 6,627,787, 6,617,016, 6,825,393, and 6,861,571; and U.S. Patent Publication Nos. 2013/0072887 A1; 2013/0211356 A1; and 2013/0306226 A1, which are all incorporated by reference herein.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed or pre-fastened by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed). Example diaper pants in various configurations are disclosed in U.S. Pat. Nos. 4,940,464; 5,092,861; 5,246,433; 5,569,234; 5,897, 545; 5,957,908; 6,120,487; 6,120,489; 7,569,039 and U.S. Patent Publication Nos. 2003/0233082 A1; 2005/0107764 A1, 2012/0061016 A1, 2012/0061015 A1; 2013/0255861 A1; 2013/0255862 A1; 2013/0255863 A1; 2013/0255864 A1; and 2013/0255865 A1, all of which are incorporated by reference herein.

Figure 1B:
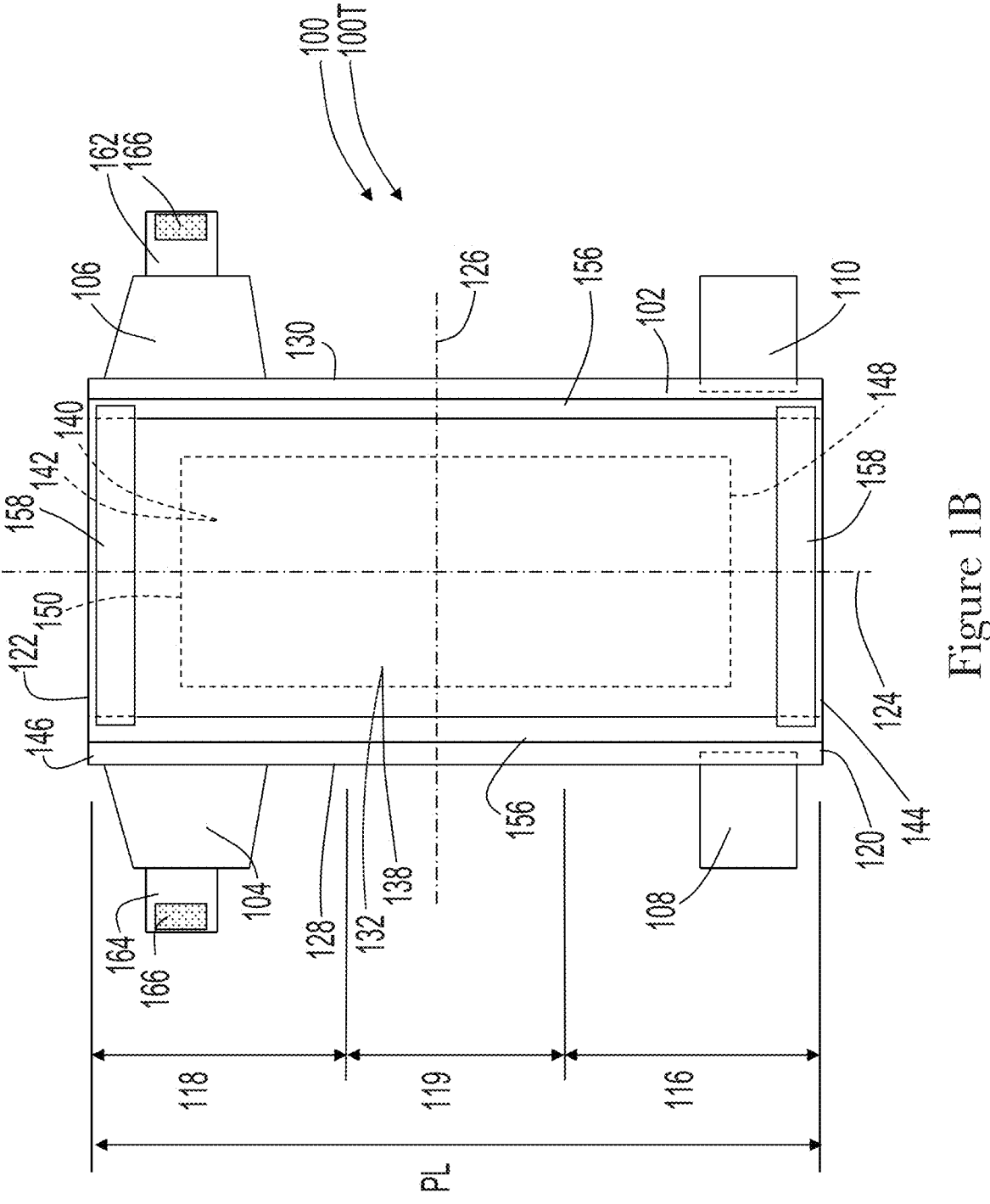
FIG. 1B is a plan view of the absorbent article of FIG. 1A that may include one or more substrates bonded in accordance with the present disclosure with the portion of the diaper that faces toward a wearer oriented towards the viewer.

For the purposes of a specific illustration, FIGS. 1A and 1B show an example of an absorbent article 100 that may be assembled in accordance with the methods and apparatuses disclosed herein. In particular, FIG. 1A shows one example of a plan view of an absorbent article 100 configured as a taped diaper 100T, with the portion of the diaper that faces away from a wearer oriented towards the viewer. And FIG. 1B shows a plan view of the diaper 100 with the portion of the diaper that faces toward a wearer oriented towards the viewer. The taped diaper 100T shown in FIGS. 1A and 1B includes an absorbent chassis 102, first and second rear side panels 104 and 106; and first and second front side panels 108 and 110.

As shown in FIGS. 1A and 1B, the diaper 100 and the chassis 102 each include a first waist region 116, a second waist region 118, and a crotch region 119 disposed intermediate the first and second waist regions. The first waist region 116 may be configured as a front waist region, and the second waist region 118 may be configured as a back waist region. In some embodiments, the length of each of the front waist region, back waist region, and crotch region may be ⅓ of the length of the absorbent article 100. The absorbent article may also include a laterally extending front waist edge 120 in the front waist region 116 and a longitudinally opposing and laterally extending back waist edge 122 in the back waist region 118. To provide a frame of reference for the present discussion, the diaper 100T in FIGS. 1A and 1B is shown with a longitudinal axis 124 and a lateral axis 126. The longitudinal axis 124 may extend through a midpoint of the front waist edge 120 and through a midpoint of the back waist edge 122. And the lateral axis 126 may extend through a midpoint of a first longitudinal or right side edge 128 and through a midpoint of a second longitudinal or left side edge 130.

As shown in FIGS. 1A and 1B, the diaper 100 includes an inner, wearer facing surface 132, and an outer, garment facing surface 134. As such, it is also to be appreciated that the various components of the diaper described below may each include inner, wearer facing surfaces 132, and an outer, garment facing surfaces 134. The chassis 102 may include a backsheet 136 and a topsheet 138. The chassis 102 may also include an absorbent assembly 140, including an absorbent core 142, disposed between a portion of the topsheet 138 and the backsheet 136. As discussed in more detail below, the diaper 100 may also include other features, such as leg elastics and/or leg cuffs, an elastic waist region, and/or flaps, e.g., side panels and/or ears, to enhance the fits around the legs and waist of the wearer, to enhance the fit around the legs of the wearer.

As shown in FIGS. 1A and 1B, the periphery of the chassis 102 may be defined by the first longitudinal side edge 128, a second longitudinal side edge 130, a first laterally extending end edge 144 disposed in the first waist region 116, and a second laterally extending end edge 146 disposed in the second waist region 118. Both side edges 128 and 130 extend longitudinally between the first end edge 144 and the second end edge 146. As shown in FIG. 1A, the laterally extending end edges 144 and 146 may form a portion of the laterally extending front waist edge 120 in the front waist region 116 and a portion of the longitudinally opposing and laterally extending back waist edge 122 in the back waist region 118. The distance between the first lateral end edge 144 and the second lateral end edge 146 may define a pitch length, PL, of the chassis 102. When the diaper 100 is worn on the lower torso of a wearer, the front waist edge 120 and the back waist edge 122 may encircle a portion of the waist of the wearer. At the same time, the side edges 128 and 130 may encircle at least a portion of the legs of the wearer. And the crotch region 119 may be generally positioned between the legs of the wearer with the absorbent core 142 extending from the front waist region 116 through the crotch region 119 to the back waist region 118.

It is to also be appreciated that a portion or the whole of the diaper 100 may also be made laterally extensible. The additional extensibility may help allow the diaper 100 to conform to the body of a wearer during movement by the wearer. The additional extensibility may also help, for example, the user of the diaper 100, including a chassis 102 having a particular size before extension, to extend the front waist region 116, the back waist region 118, or both waist regions of the diaper 100 and/or chassis 102 to provide additional body coverage for wearers of differing size, i.e., to tailor the diaper to an individual wearer. Such extension of the waist region or regions may give the absorbent article a generally hourglass shape, so long as the crotch region is extended to a relatively lesser degree than the waist region or regions, and may impart a tailored appearance to the article when it is worn.

As previously mentioned, the diaper 100 may include a backsheet 136. The backsheet 136 may also define the outer surface 134 of the chassis 102. The backsheet 136 may be impervious to fluids (e.g., menses, urine, and/or runny feces) and may be manufactured in part from a thin plastic film, although other flexible liquid impervious materials may also be used. The backsheet 136 may prevent the exudates absorbed and contained in the absorbent core from wetting articles which contact the diaper 100, such as bedsheets, pajamas and undergarments. The backsheet 136 may also comprise a woven or nonwoven material, polymeric films such as thermoplastic films of polyethylene or polypropylene, and/or a multi-layer or composite materials comprising a film and a nonwoven material (e.g., having an inner film layer and an outer nonwoven layer). The backsheet may also comprise an elastomeric film. An example backsheet 136 may be a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 136 may also be embossed and/or matte-finished to provide a more clothlike appearance. Further, the backsheet 136 may permit vapors to escape from the absorbent core (i.e., the backsheet is breathable) while still preventing exudates from passing through the backsheet 136. The size of the backsheet 136 may be dictated by the size of the absorbent core 142 and/or particular configuration or size of the diaper 100.

Also described above, the diaper 100 may include a topsheet 138. The topsheet 138 may also define all or part of the inner surface 132 of the chassis 102. The topsheet 138 may be compliant, soft feeling, and non-irritating to the wearer's skin. It may be elastically stretchable in one or two directions. Further, the topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wetlaid, meltblown, hydroentangled, or otherwise processed as is known in the art.

Topsheets 138 may be selected from high loft nonwoven topsheets, apertured film topsheets and apertured nonwoven topsheets. Apertured film topsheets may be pervious to bodily exudates, yet substantially non-absorbent, and have a reduced tendency to allow fluids to pass back through and rewet the wearer's skin. Exemplary apertured films may include those described in U.S. Pat. Nos. 5,628,097; 5,916, 661; 6,545,197; and 6,107,539, which are all incorporated by reference herein.

As mentioned above, the diaper 100 may also include an absorbent assembly 140 that is joined to the chassis 102. As shown in FIGS. 1A and 1B, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834, 735, which are all incorporated by reference herein.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprise primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 A1 and 2004/ 0097895 A1.

As previously mentioned, the diaper 100 may also include elasticized leg cuffs 156 and an elasticized waistband 158. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695,278; 4,795,454; 4,704,115; and U.S. Patent Publication No. 2009/0312730 A1, which are all incorporated by reference herein.

As shown in FIG. 1B, the chassis 102 may include longitudinally extending and laterally opposing leg cuffs 156 that are disposed on the interior surface 132 of the chassis 102 that faces inwardly toward the wearer and contacts the wearer. Each leg cuff may have a proximal edge. The leg cuffs may also overlap the absorbent assembly 140, wherein the proximal edges extend laterally inward of the respective side edges of the absorbent assembly 152 and 154. In some configurations, the leg cuffs may not overlap the absorbent assembly. It is to be appreciated that the leg cuffs may be formed in various ways, such as for example, by folding portions of the chassis 102 laterally inward, i.e., toward the longitudinal axis 124, to form both the respective leg cuffs and the side edges 128 and 130 of the chassis 102. In another example, the leg cuffs may be formed by attaching an additional layer or layers to the chassis at or adjacent to each of the respective side edges and of the chassis. Each of the leg cuffs may be joined to the interior surface 132 of the chassis and/or the absorbent assembly in leg cuff attachment zones in the front waist region 116 and in leg cuff attachment zones in the back waist region 118. The leg cuffs may extend to the same longitudinal extent as the absorbent article or alternatively the leg cuffs may have a longitudinal extent that is less than the absorbent article.

The elasticized waistband 158 may provide improved fit and containment and may be a portion or zone of the diaper 100 that may elastically expand and contract to dynamically fit a wearer's waist. It is to be appreciated that the elasticized waistband 158 may be located in various positions relative to various diaper components. For example, the elasticized waistband 158 may be positioned longitudinally inwardly from the waist edges 120, 122 of the diaper and/or toward the lateral edges 148, 150 of the absorbent core 142. In some configurations, the elasticized waistband 158 may be positioned with a lateral edge that is coterminous with the waist edges 120, 122. In some configurations, the elasticized waistband 158 may be positioned such that laterally opposing end regions of the waistband 158 are located laterally inward from the leg cuffs 156. In some configurations, the elasticized waistband 158 may be positioned such that laterally opposing end regions of the waistband 158 overlap the leg cuffs 156. In some configurations, the elasticized waistband 158 may be positioned on the wearer facing surface 132 of the topsheet 138. In some configurations, the waistband 158 may be positioned on the wearer facing surfaces 132 of the topsheet 138 and the leg cuffs 156. In some configurations, the waistband 158 may be positioned on the wearer facing surfaces 132 of the topsheet 138 and laterally opposing end regions of the waistband 158 may be positioned between the leg cuffs 156 and the topsheet 138. In some configurations, the elasticized waistband 158 may be positioned between the garment facing surface 132 of the topsheet 138 and the wearer facing surface 132 of the backsheet 136. And in some configurations, the elasticized waistband 158 may be positioned on the garment facing surface 134 of the backsheet 136. The diaper 100 may also include more than one elasticized waistband 158, for example, having one waistband 158 positioned in the back waist region 118 and one waistband 158 positioned in the front wait region 116, although other embodiments may be constructed with a single elasticized waistband 158. The elasticized waistband 158 may be constructed in a number of different configurations including those described in U.S. Pat. Nos. 4,515,595 and 5,151,092.

Taped diapers may be manufactured and provided to consumers in a configuration wherein the front waist region and the back waist region are not fastened, pre-fastened, or connected to each other as packaged, prior to being applied to the wearer. For example, the taped diaper 100 may be folded about a lateral centerline with the interior surface 132 of the first waist region 116 in surface to surface contact with the interior surface 132 of the second waist region 118 without fastening or joining the waist regions together. The rear side panels 104 and 106 and/or the front side panels 108 and 110 may also be folded laterally inward toward the inner surfaces 132 of the waist regions 116 and 118.

The diaper 100 may also include various configurations of fastening elements to enable fastening of the front waist region 116 and the back waist region 118 together to form a closed waist circumference and leg openings once the diaper is positioned on a wearer. For example, as shown in FIGS. 1A and 1B, the diaper 100 may include first and second fastening members 162, 164, also referred to as tabs, connected with the first and second rear side panels 104, 106, respectively. The diaper may also include first and second front side panels 108, 110, that may or may not include fastening members.

With continued reference to FIGS. 1A and 1B, each side panel 104, 106 and/or fastening member 162 and 164 may form a portion of or may be permanently bonded, adhered or otherwise joined directly or indirectly to the chassis 102 laterally inward from the side edge 128 and 130, in one of the front waist region 116 or the back waist region 118. Alternatively, the fastening members 162, 164 may form a portion of or may be permanently bonded, adhered or otherwise joined directly or indirectly to the first and second rear panels 104, 106 at or adjacent the distal edge of the panel and/or the first and second front side panels 108 and 110 at or adjacent the distal edge of the side panel. It is to be appreciated that the fastening members and/or side panels may be assembled in various ways, such as disclosed for example, in U.S. Pat. No. 7,371,302. The fastening members 162, 164 and/or side panels 104, 106, 108, 110 may also be permanently bonded or joined at or adjacent the side edges 128 and 130 of the chassis 102 in various ways, such as for example, by adhesive bonds, sonic bonds, pressure bonds, thermal bonds or combinations thereof, such as disclosed for example, U.S. Pat. No. 5,702,551, which is incorporated by reference herein.

Referring now to FIG. 1B, the first fastening member 162 and/or the second fastening member 164 may include various types of releasably engageable fasteners. The first and second fastening members 162 and/or 164 may also include various types of refastenable fastening structures. For example, the first and second fastening members 162 and 164 may include mechanical fasteners, 166, in the form of hook and loop fasteners, hook and hook fasteners, macro-fasteners, buttons, snaps, tab and slot fasteners, tape fasteners, adhesive fasteners, cohesive fasteners, magnetic fasteners, hermaphroditic fasteners, and the like. Some examples of fastening systems and/or fastening members 162, 164 are discussed in U.S. Pat. Nos. 3,848,594; 4,662,875; 4,846, 815; 4,894,060; 4,946,527; 5,151,092; 5,221,274; 6,251, 097; 6,669,618; 6,432,098; and U.S. Patent Publication Nos. 2007/0078427 A1 and 2007/0093769 A1, which are all incorporated by reference herein.

As previously mentioned, the fastening members 162 and 164 may be constructed from various materials and may be constructed as a laminate structure. The fastening members 162 and 164 may also be adapted to releasably and/or refastenably engage or connect with another portion of the diaper 100. For example, as shown in FIG. 1A, the diaper 100 may include a connection zone 168, sometimes referred to as a landing zone, in the first waist region 116. As such, when the taped diaper 100 is placed on a wearer, the fastening members 162 and 164 may be pulled around the waist of the wearer and connected with the connection zone 168 in the first waist region 116 to form a closed waist circumference and a pair of laterally opposing leg openings. It is to be appreciated that the connection zone may be constructed from a separate substrate that is connected with the chassis 102 of the taped diaper. In some embodiments, the connection zone may be integrally formed as part of the backsheet 136 of the diaper 100 or may be formed as part of the first and second front panels 108, 110, such as described in U.S. Pat. Nos. 5,735,840 and 5,928,212, which are both incorporated by reference herein.

As previously mentioned, absorbent articles may be assembled with various components that may constructed with the substrates described herein. Thus, in the context of the previous discussion, the apparatuses and methods herein may be used to bond discrete elastic parts under tension to an advancing carrier substrate during the assembly of an absorbent article 100. For example, the apparatuses and methods herein may be utilized to bond elastic parts that may be configured as waistbands 158 to carrier substrates that may be configured as topsheets 138 or backsheets 136 during the manufacture of absorbent articles 100. It is to be appreciated that the systems and methods disclosed herein are applicable to work with various types of converting processes and/or machines. For example, FIG. 2 shows a schematic representation of a converting process including an apparatus or system 300 that bonds discrete elastic parts 200 with an advancing carrier substrate 202 to form a laminate 204.

Figure 2:
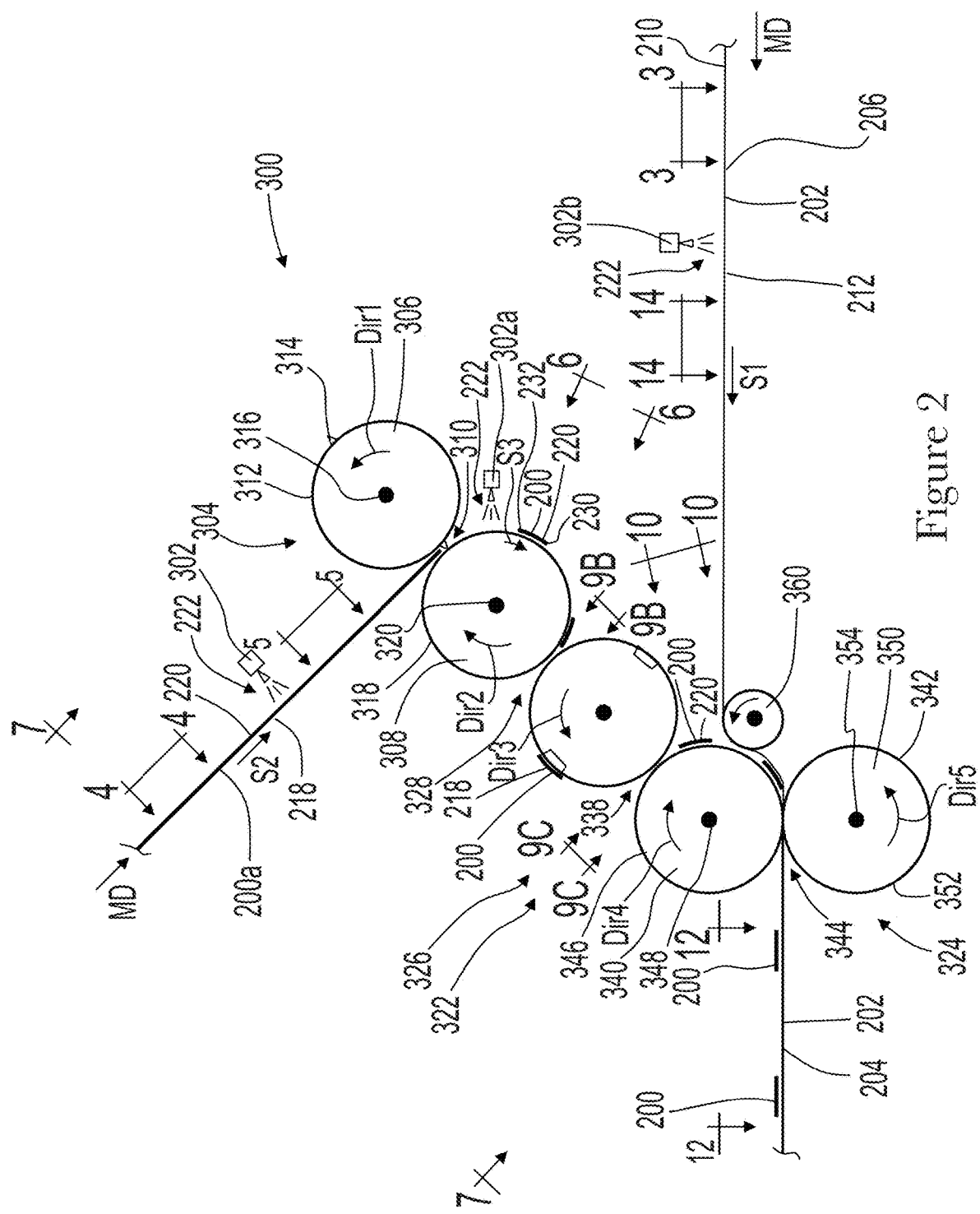
FIG. 2 is a schematic side view of an apparatus for bonding elastic parts to an advancing carrier web.
Figures 2A, 3:
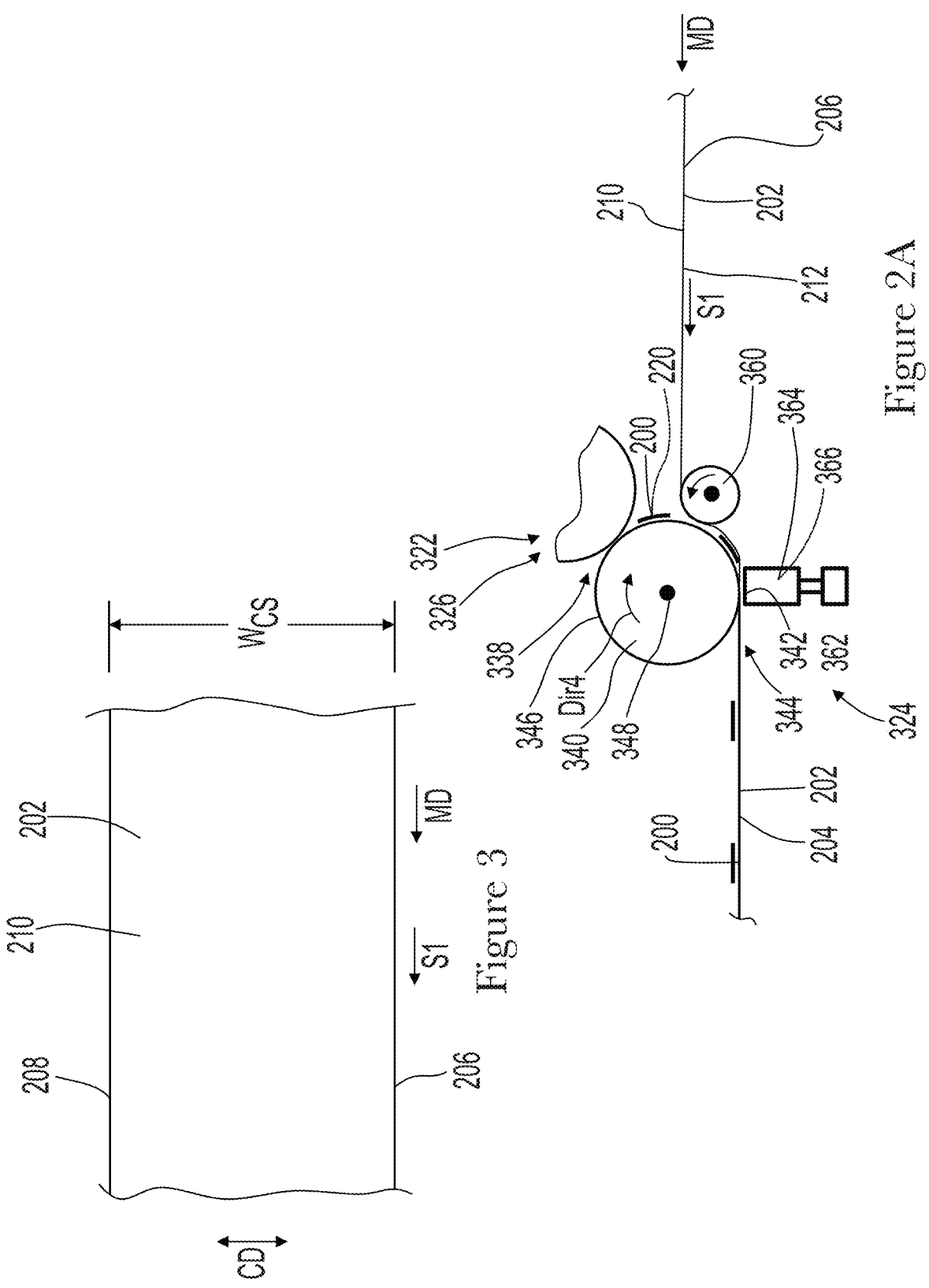
FIG. 2A is a detailed schematic view of a bonding apparatus with a pressing surface comprising an ultrasonic bonding device.
FIG. 3 is a view of a carrier substrate taken along section 3-3 in FIG. 2.

As shown in FIGS. 2 and 3, the carrier substrate 202 may advance in a machine direction MD at a first speed S1. The carrier substrate comprises a first longitudinal edge 206 and a second longitudinal edge 208 separated from the first longitudinal edge 206 in a cross direction CD to define a width $W_{CS}$. The carrier substrate 202 also includes a first surface 210 and an opposing second surface 212. As discussed in more detail below, discrete elastic parts 200 are bonded with the first surface 210 of the carrier substrate 202.

In the context of components of absorbent articles 100 discussed above and assembly processes thereof, the elastic parts 200 may be configured as waistbands 158 and the carrier substrate 202 may be configured as a continuous topsheet 138, backsheet 136, or continuous laminate of a combined topsheet 138 and backsheet 136. As such, the first surface 210 of the carrier substrate 202 may correspond with the wearer facing surface 132 or the garment facing surface 134 of the topsheet 138 or backsheet 136. In some configurations, the elastic part 200 may be bonded between a topsheet 138 and a backsheet 136. For example, the elastic part 200 may be bonded with the wearer facing surface 132 of the backsheet 136, which is subsequently bonded with a topsheet 138. In another example, the elastic part 200 may be bonded with the garment facing surface 134 of the topsheet 138, which is subsequently bonded with a backsheet 136. In yet another example, the elastic part 200 may be bonded with the garment facing surface 134 of the backsheet 136, wherein the wearer facing surface 132 of the backsheet 136 may have been previously bonded with a topsheet 138 or may be subsequently bonded with a topsheet 138. In another example, the elastic part 200 may be bonded with the wear facing surface 132 of the topsheet 136, wherein the garment facing surface 134 of the topsheet 138 may have been previously bonded with a backsheet 136 or may be subsequently bonded with a backsheet 136.

Figures 3A, 4, 5:
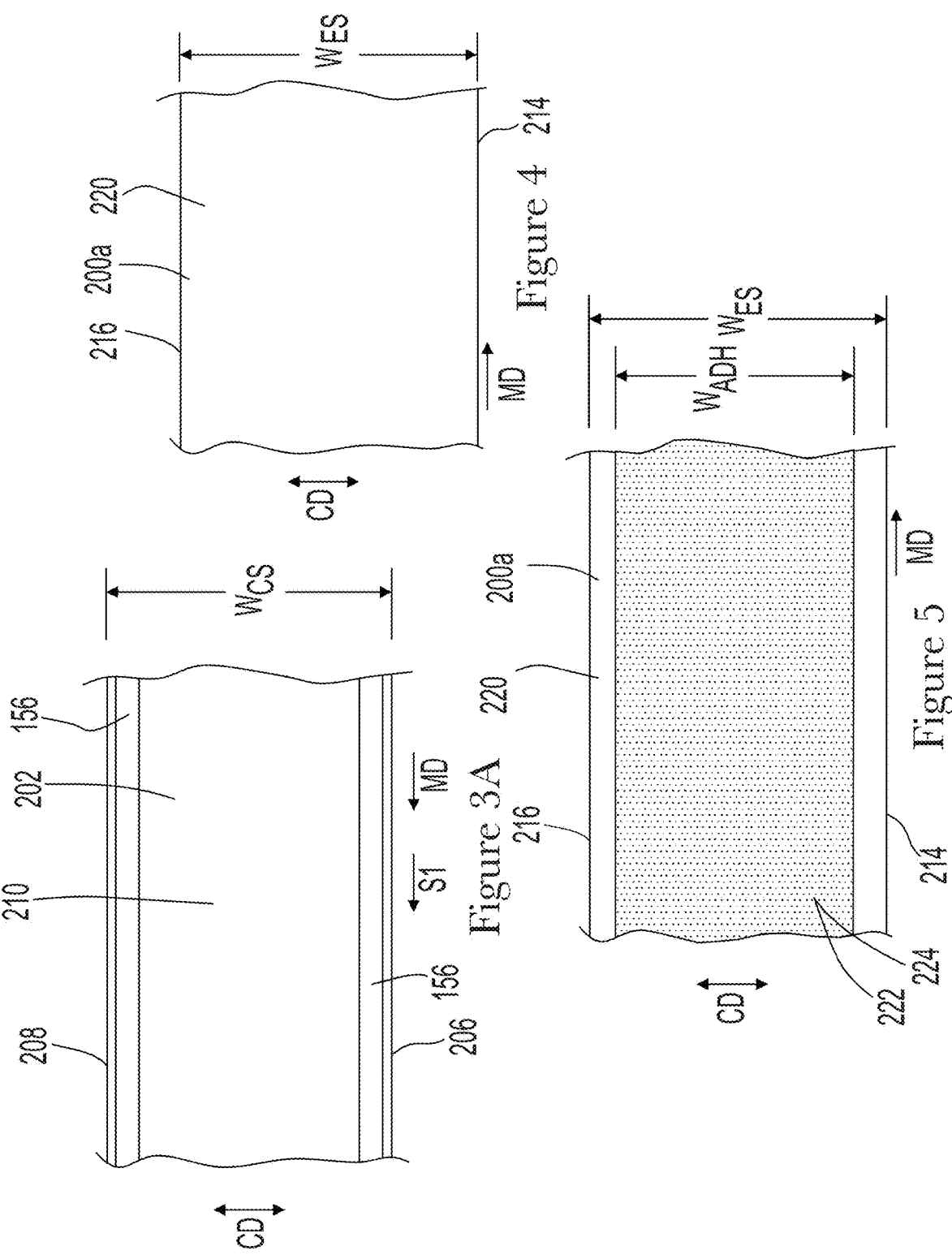
FIG. 3A is a view of a carrier substrate with leg cuffs taken along section 3-3 in FIG. 2.
FIG. 4 is a view of a continuous elastic substrate taken along section 4-4 in FIG. 2.
FIG. 5 is a view of a continuous elastic substrate with a continuous region of adhesive taken along section 5-5 in FIG. 2.

As shown in FIG. 3A, the carrier substrate 202 may also include leg cuffs 156 positioned on the first surface 210 adjacent the first longitudinal edge 206 and the second longitudinal edge 208. As such, portions of the discrete elastic parts 200 may also be bonded with the leg cuffs 156. In some configurations, the discrete elastic parts 200 may be bonded with the carrier substrate 202 and leg cuffs 156 may subsequently be bonded with the carrier substrate 202. The leg cuffs 156 may be positioned relative the elastic part 200 such that the leg cuffs 156 may or may not partially cover or overlap opposing end portions of the elastic part 200. In some configurations, the leg cuffs 156 may be sandwiched between the elastic parts 200 and the carrier substrate 202. And in some configurations, the elastic parts 200 may be sandwiched between the leg cuffs 156 and the carrier substrate 202.

Referring now to FIGS. 2 and 4, a continuous elastic substrate 200a advanced at a second speed S2 in a machine direction MD, wherein the second speed S2 is less than the first speed S1. The continuous elastic substrate 200a comprises a first longitudinal edge 214 and a second longitudinal edge 216 separated from the first longitudinal edge 214 in the cross direction CD to define a width $W_{ES}$. The continuous elastic substrate 200a also includes a first surface 218 and an opposing second surface 220. The continuous elastic substrate 200a is stretchable in at least one direction and is oriented such that the continuous elastic substrate 200a is stretchable in the cross direction CD. As such, the width $W_{ES}$ of the continuous elastic substrate may be an unstretched width. In some configurations, the width $W_{ES}$ of the continuous elastic substrate 200a may be a partially stretched width.

With continued reference to FIGS. 2, 4, and 5, the system 300 may include an adhesive applicator device 302 that deposits adhesive 222 onto the second surface 220 of the continuous elastic substrate 200a. It is to be appreciated that the adhesive applicator device 302 may be configured in various way, such as for example, as a spray nozzle and/or a slot coating device. In some configurations, the adhesive applicator device 302 may be configured in accordance with the apparatuses and/or methods disclosed in U.S. Pat. Nos. 8,186,296; 9,265,672; 9,248,054; and 9,295,590 and U.S. Patent Publication No. 2014/0148773 A1, which are all incorporated by reference herein.

It is to be appreciated that the adhesive 222 may be applied to the continuous elastic substrate 200a to define regions of adhesive 222 on the second surface 220 having various shapes and sizes relative to the continuous elastic substrate 200a. For example, as shown in FIG. 5, the adhesive 222 may be applied to the second surface 220 of the continuous elastic substrate 200a to define a region 224 of adhesive 222 extending continuously in the machine direction MD and the cross direction CD. The adhesive 222 may extend in the cross direction CD define a width $W_{ADH}$. In some configurations, the width $W_{ADH}$ of adhesive 222 may be less than the width $W_{ES}$ of the continuous elastic substrate 200a, and in some configurations, the width $W_{ADH}$ may be equal to the width $W_{ES}$ of the continuous elastic substrate 200a.

Figures 6, 10:
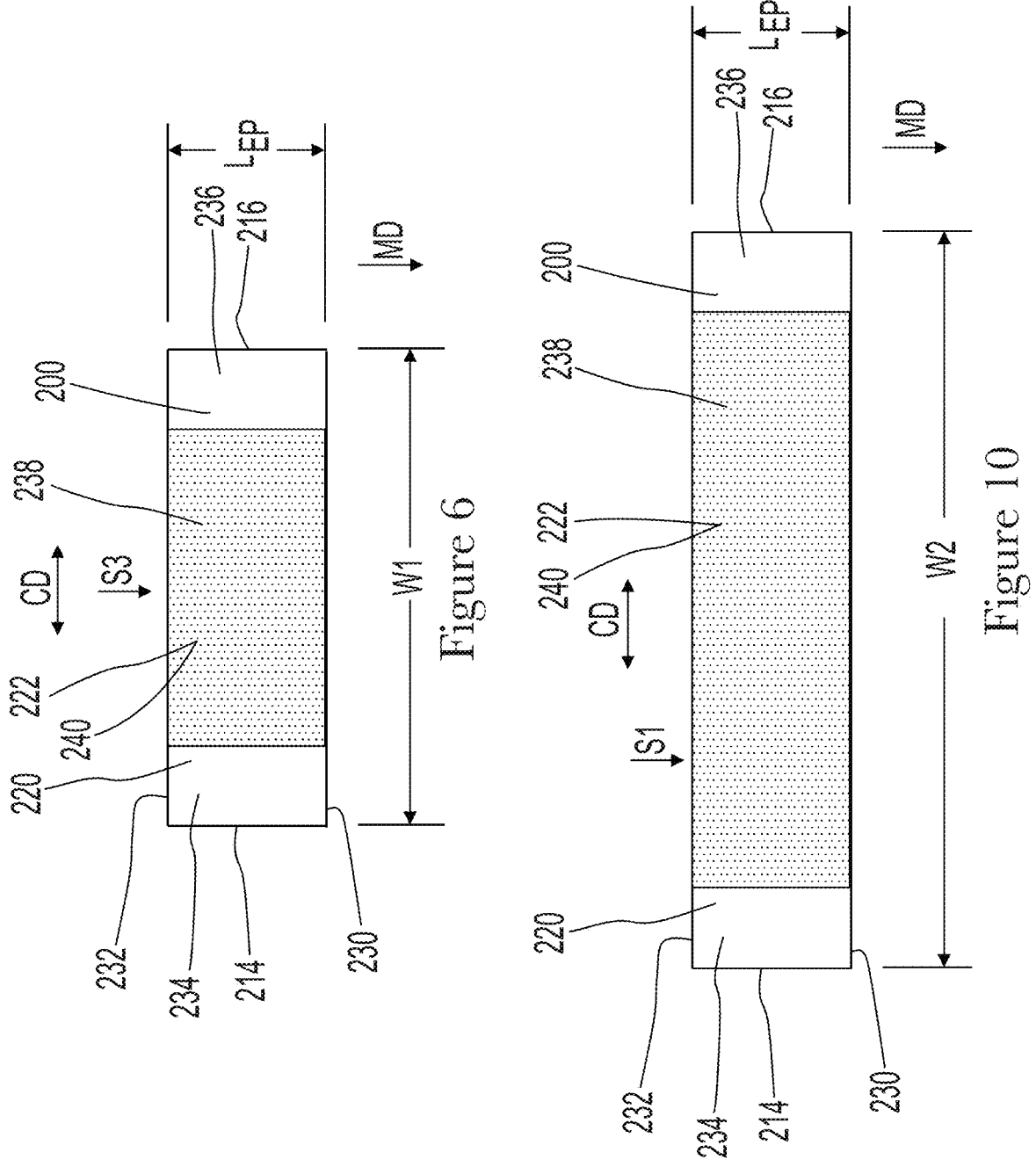
FIG. 6 is a view of a discrete elastic part laid out flat with a zone of adhesive thereon taken along section 6-6 in FIG. 2.
FIG. 10 is a view of a stretched discrete elastic part laid out flat with a zone of adhesive thereon taken along section 10-10 in FIG. 2.

As shown in FIGS. 2, 5, and 6, the continuous elastic substrate 200a may advance in the machine direction MD from the adhesive applicator device 302 to a cutting device 304 that cuts and separates discrete elastic parts 200 from the continuous elastic substrate 200a. As such, the discrete elastic parts 200 each include a leading edge 230 and a trailing edge 232 and defines a length $L_{EP}$ in the machine direction MD extending from the leading edge 230 to the trailing edge 232. The elastic part 200 also includes first and second longitudinal edges 214, 216 that correspond with the longitudinal edges 214, 216 of the continuous elastic substrate 200a extending between the leading and trailing edges 230, 232. In addition, the elastic part 200 includes first and second surfaces 218, 220 that correspond with the first and second surfaces 218, 220 of the continuous elastic substrate 200a.

As shown in FIG. 6, the discrete elastic part 200 also includes a first end region 234 adjacent the first longitudinal edge 214 and a second end region 236 adjacent the second longitudinal edge 216, wherein the second end region 236 is separated from the first end region 234 in the cross direction CD by a central region 238. As discussed above, adhesive 222 may be applied to the second surface 220 of the continuous elastic substrate 200a. As such, the discrete elastic part 200 may include a zone 240 of adhesive 222 on the second surface 220. It is to be appreciated that the zone 240 of adhesive 222 may define various sizes and shapes relative to the elastic part 200. For example, as shown in FIG. 6, the zone 240 of adhesive may extend in the cross direction CD for less than the entire width W1 of the discrete elastic part 200. In some configurations, the zone 240 of adhesive 222 may be positioned only on the central region 238 of the discrete elastic part 200 such that the first end region 234 and the second end region 236 of the second surface 220 of the discrete elastic part 200 may not include any adhesive 222.

Figures 7, 8:
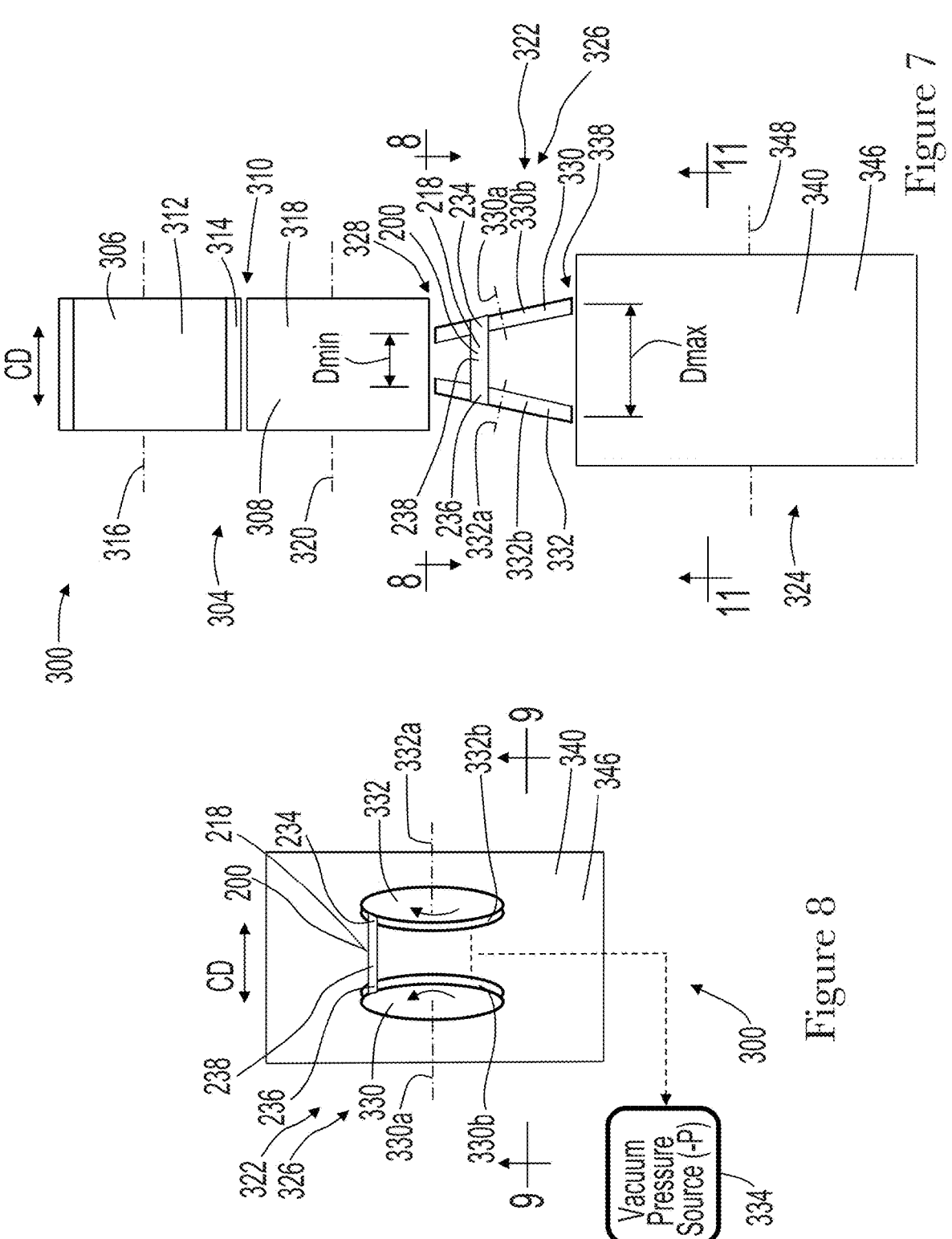
FIG. 7 is a view of a cutting device, transfer device, and bonding device taken along section 7-7 in FIG. 2.
FIG. 8 is a view of the transfer device and bonding device taken along section 8-8 in FIG. 7.

As shown in FIGS. 2 and 7, the cutting device 304 may include a knife roll 306 positioned adjacent an anvil roll 308 to define a nip 310 therebetween. The knife roll 306 may include an outer circumferential surface 312 and one or more blades 314 adapted to rotate about an axis 316 in a first direction Dir1. The anvil roll 308 may include an outer circumferential surface 318 adapted to rotate about an axis 320 in a second direction Dir2 opposite the first direction Dir1 such that the outer circumferential surface 318 advances at a third speed S3, wherein the third speed S3 is greater than the second speed S2. With continued reference to FIG. 2, as the continuous elastic substrate 200a advances through the nip 310 between the knife roll 306 and the anvil roll 310, the blade 314 operates to cut the discrete elastic part 200 from the continuous elastic substrate 200a. Because the outer circumferential surface 318 of the anvil roll 308 advances at the third speed S3, the cut discrete elastic part 200 may then accelerate from the second speed S2 to the third speed S3 on the outer circumferential surface 318 of the anvil roll 308.

Figure 12:
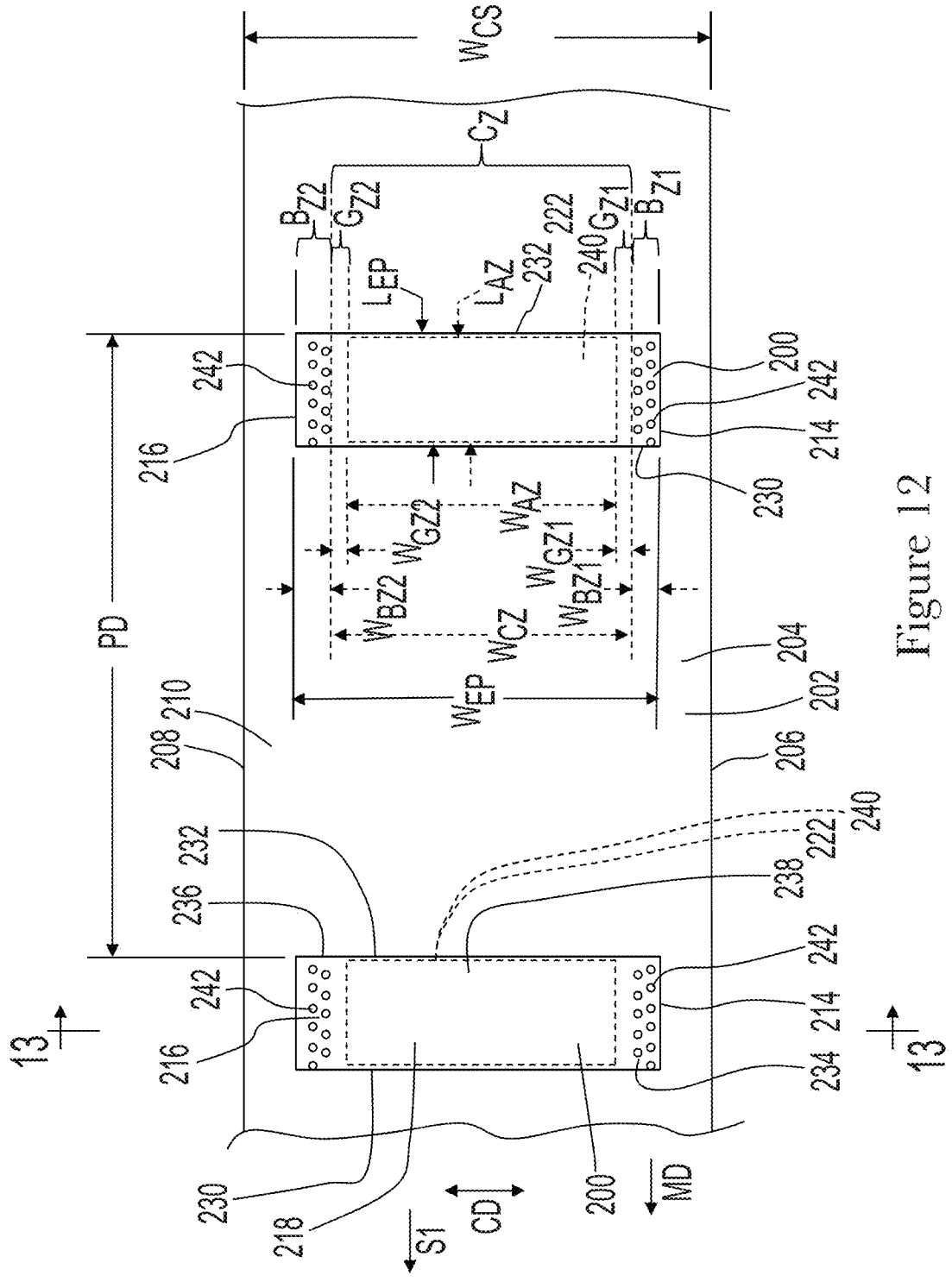
FIG. 12 is a view of a laminate including the elastic part and the carrier substrate taken along section 12-12 in FIG. 2.

In some configurations, the third speed S3 may be equal to the first speed S1 of the advancing carrier substrate 202. In some configurations, the third speed S3 may be less than or greater than the first speed S1 of the advancing carrier substrate 202, and as such, the discrete elastic part may be accelerated or decelerated downstream of the anvil roll 308 from the third speed S3 to the first speed S1 before being combined with the carrier substrate 202. Because the first speed S1 of the carrier substrate is greater than the second speed S2, the discrete elastic parts 200 are accelerated from the second speed S2 to the first speed S1 before bonding with the carrier substrate 202. By accelerating discrete elastic parts 200 from the second speed S2 to the first speed S1, trailing edges 232 (or leading edges 230) of consecutively cut discrete elastic parts 200 may be separated from each other in the machine direction MD by a pitch distance PD, such as shown in FIG. 12, which may correspond with the pitch length PL described above with reference to FIGS. 1A and 1B. The anvil roll 308 may also be configured to apply vacuum pressure to the discrete elastic parts 200 to help hold the discrete elastic parts 200 on the outer circumferential surface 318 as the anvil roll 308 rotates.

It is to be appreciated that the cutting device 304 may be configured in various ways. For example, in some configurations, the blade 314 may be configured such that resulting cut lines and corresponding leading edges 230 and trailing edges 232 of the discrete elastic parts 200 may be straight and/or curved. The cutting device 304 may also be adapted to cut the discrete elastic parts 200 such that material along the cut line adjacent leading edges 230 and trailing edges 232 is fused and/or pressure bonded together. It is also to be appreciated that the positions of the knife roll 306 and anvil roll 308 may be opposite to that which is illustrated in FIG. 2, and as such, the discrete elastic parts 200 may remain on the outer circumferential surface 312 of the knife roll 306 as opposed to the anvil roll 308. It is also to be appreciated that the cutting device 304 may be configured to convey and/or cut the discrete elastic parts 200 in different ways. For example, the cutting device 304 may be adapted to advance the continuous elastic substrate 200a and/or the discrete elastic parts 200 on a conveyor belt. In another example, the cutting device 304 may include a laser adapted to cut the discrete elastic parts 200 from the continuous elastic substrate 200a. It is also to be appreciated that one or more components of the cutting device 304 may be configured to operate at constant and/or variable speeds. For example, the knife roll 306 and/or the anvil roll 308 may be connected with various types of motors, such as servo motors for example, that may rotate the knife roll 306 and/or the anvil roll 308 at constant and/or variable angular velocities.

With reference to FIG. 2, the apparatus 300 may include a rotatable transfer device 322 that transfers the discrete elastic parts 200 from the cutting device 304 to a bonding device 324, which in turn, combines the elastic parts 200 with the carrier substrate 202. The transfer device 322 may also be configured to stretch the discrete elastic parts 200 in the cross direction CD. As such, the transfer device 322 may be configured as a spreader mechanism 326, such as shown in FIGS. 7 and 8. With continued reference to FIGS. 2, 7, and 8, the transfer device 322 may be positioned adjacent the anvil roll 308 to define a nip 328 therebetween. In some configurations, the anvil roll 308 may be configured to apply positive air pressure, sometimes referred to as blow-off air, to the discrete elastic parts 200 adjacent the nip 328 to help remove the discrete elastic parts 200 from the anvil roll 308 during transfer to the transfer device 322. As discussed in more detail below, the discrete elastic parts 200 are received from the anvil roll 308 and the spreader mechanism 326 operates to stretch discrete elastic parts 200 in the cross direction CD. The stretched discrete elastic parts 200 are then advanced from the spreader mechanism 326 onto a rotating component of the bonding device 324, which in turn, bonds the stretched discrete elastic parts 200 onto the carrier substrate 202.

Figures 9, 9A:
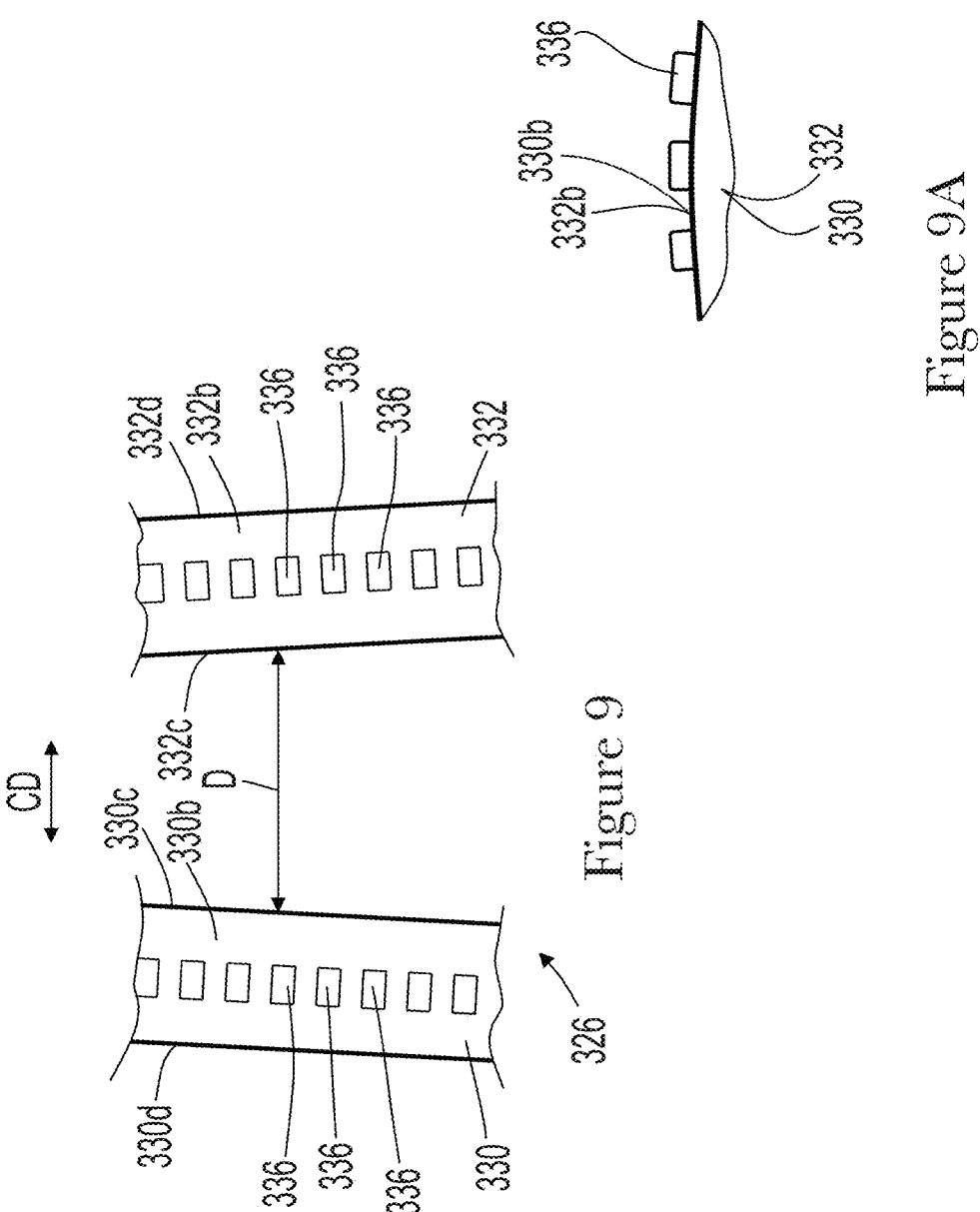
FIG. 9 is a detailed view of the spreader mechanism taken along section 9-9 in FIG. 8.
FIG. 9A is a detailed view of radially protruding nubs on an outer rim of a disk.

As shown in FIGS. 7 and 8, the spreader mechanism 326 may include a first disk 330 and a second disk 332, wherein the first disk 330 is displaced from the second disk 332 in the cross direction CD. The first disk 330 is adapted to rotate about an axis of rotation 330a and the second disk 332 is adapted to rotate about an axis of rotation 332a, wherein the first and second disks 330, 332 may rotate in a third direction Dir3 that is opposite the second direction Dir2. As shown in FIG. 9, the first disk 330 includes an outer rim 330b extending axially between an inner edge 330c and an outer edge 330d, and the second disk 332 includes an outer rim 332b extending axially between an inner edge 332c and an outer edge 332d.

As shown in FIGS. 7-9, the first disk 330 and the second disk 332 are canted relative to each other such that the outer rims 330b, 332b are separated from each other by a distance D that increases from a minimum distance Dmin at a first location to a maximum distance Dmax at a second location. As discussed below, the discrete elastic parts 200 are transferred from the cutting device 304 onto the outer rims 330b, 332b during operation. Because the first and second disks 330, 332 are canted, rotation of the disks 330, 332 causes the rims 330b, 332b to pull on first end region 234 and the second end region 236 of discrete elastic parts 200 and stretch the central regions 238 of the discrete elastic parts 200 in the cross direction CD before the discrete elastic parts 200 are transferred to the bonding device 324. As shown in FIGS. 2, 6, and 10, the spreader mechanism 326 may operate to stretch the discrete elastic parts 200 in the cross direction from a first width W1 to a second width W2 that is greater than the first width W1.

With reference to FIGS. 2, 7, and 8, the disks 330, 332 may also be configured to help grip the opposing first and second end regions 234, 236 of the discrete elastic parts 200 during operation. For example, the first disk 330 and the second disk 332 may each be fluidly connected with a vacuum pressure source 334. As such, vacuum air pressure may be used to help hold the discrete elastic parts 200 onto the rims 330b, 332b during operation. As shown in FIGS. 9 and 9A, the disks 330, 332 may also include nubs 336 that protrude radially outward from the rims 330b, 332b. As such, the nubs 336 may also help prevent the first and second end regions 234, 236 of the discrete elastic parts 200 from sliding along the rims 330b, 332b while stretching the central region 238 of the discrete elastic parts 200. It is also noted that because the first and second end regions 234, 236 of the discrete elastic part 200 are held on the rims 330b, 332b during the stretching operation, the central region 238 of the discrete elastic part 200 is stretched while the first and second end regions 234, 236 may not be stretch or may be stretched to a much lesser degree than the central region 238.

As previously discussed with reference to FIG. 6, the elastic part 200 may include a zone 240 of adhesive 222 that is positioned only on the central region 238 of the discrete elastic part 200 and wherein the first end region 234 and the second end region 236 of the second surface 220 of the discrete elastic part 200 may not include any adhesive 222. As shown in FIGS. 2, 7, and 8, once transferred to the transfer device 322, the elastic parts 200 may be oriented such that the first surface 218 may be facing radially outward, and the second surface 220 and the zone 240 of adhesive 222 may be facing radially inward. As such, the arrangement of disks 330, 322 of the spreader mechanism 326 provide the ability to rotatably convey the elastic parts 200 from the cutting device 304 to the bonding device 324 with a zone 240 of adhesive 222 that faces radially inward without having to contact the adhesive 222 with the disks 330, 332.

It is to be appreciated that the transfer device 322 may be configured in various ways to help ensure a relatively smooth and consistent transfer of the discrete elastic parts 200 from the cutting device 304 to the transfer device 322 as well as a relatively smooth and consistent transfer of the discrete elastic parts 200 from the transfer device 322 to the bonding device 324. For example, as discussed above, the transfer device 322 may include a first disk 330 and a second disk 332 that are canted relative to each other. Thus, as discussed below with reference to FIGS. 9B and 9C, the first and second disks 330, 332 may be configured to compensate for the canted orientations so as to define a relatively constant gap between the rims 330b, 332b and the outer circumferential surface 318 of the anvil roll 308 at or near the nip 328 as well as a relatively constant gap between the rims 330b, 332b and the outer circumferential surface 346 of the pattern roll 340 at or near the nip 338.

Figure 9B:
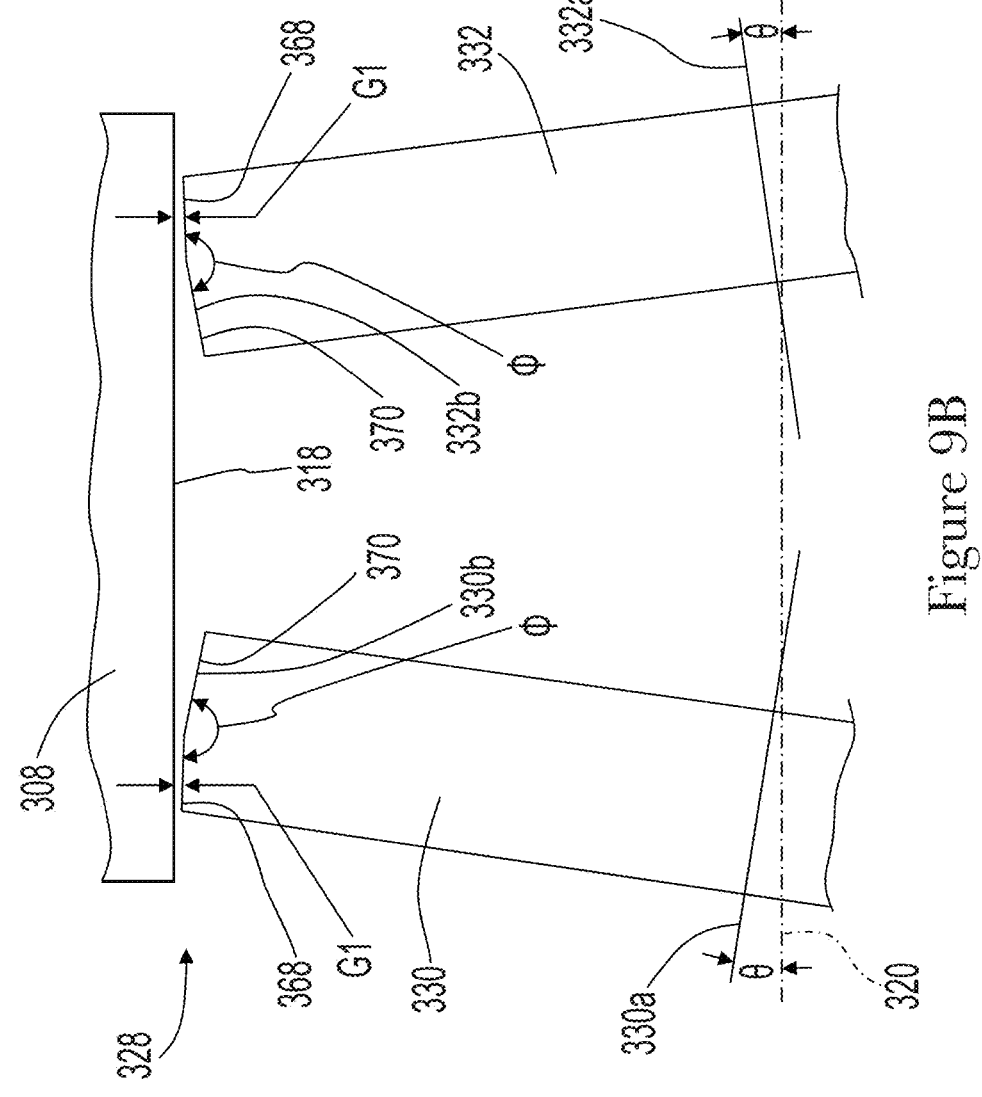
FIG. 9B is a detailed view of the spreader mechanism taken along section 9B-9B in FIG. 2.
Figure 9C:
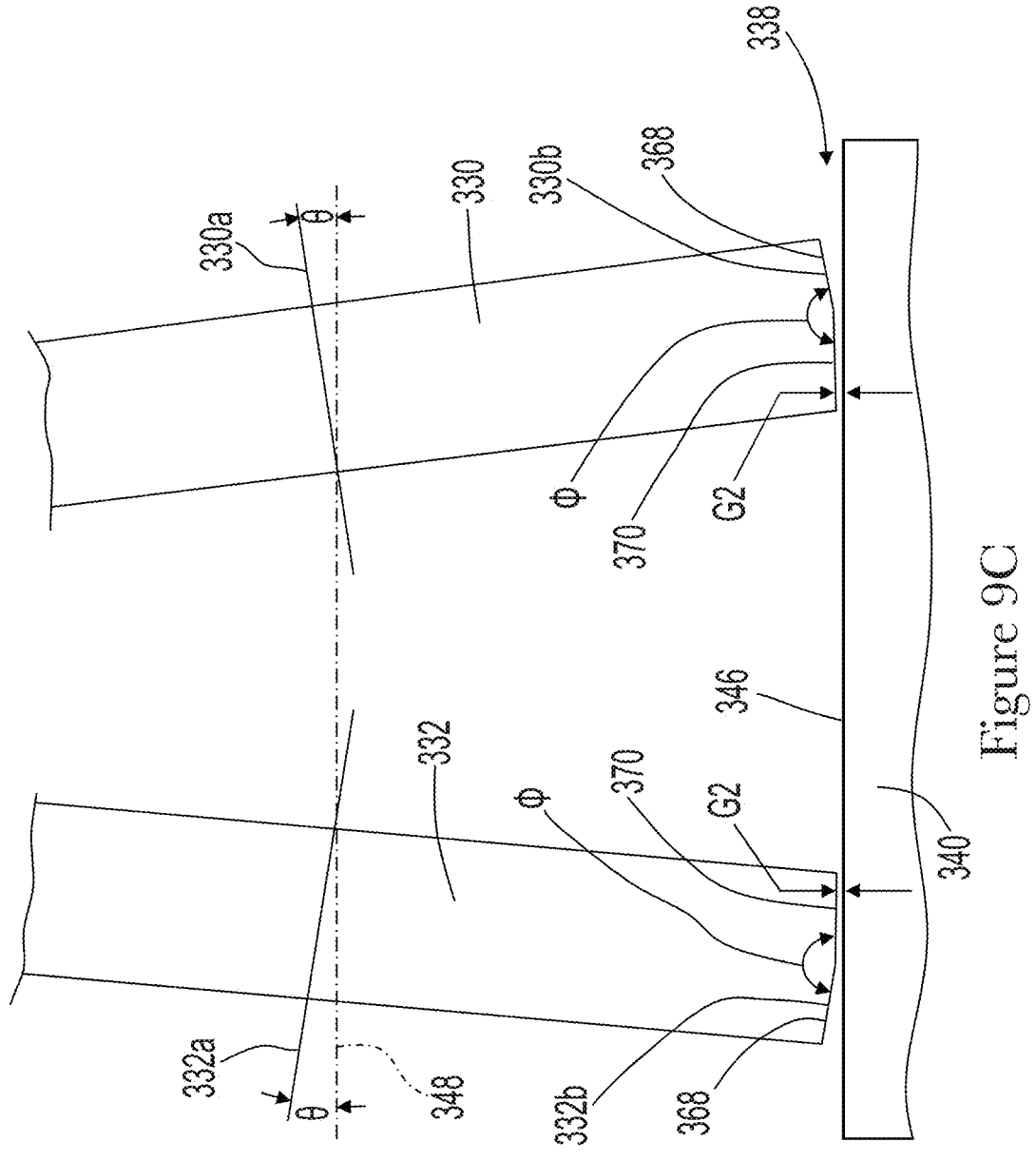
FIG. 9C is a detailed view of the spreader mechanism taken along section 9C-9C in FIG. 2.

As shown in FIGS. 9B and 9C, the first disk 330 may be oriented such that the rotation axis 330a is angularly offset from the rotation axis 320 of anvil roll 308 and the rotation axis 348 of the pattern roll 340 to define a canting angle θ therebetween. In addition, the second disk 332 may be oriented such that the rotation axis 332a is angularly offset from the rotation axis 320 of anvil roll 308 and the rotation axis 348 of the pattern roll 340 to define a canting angle θ therebetween. It is to be appreciated that the rotation axis 320 of anvil roll 308 is shown in FIG. 9B relative to the rotation axes 330a, 332a of the first and second disks 330, 332 only to illustrate the canting angle θ therebetween and does not represent the actual physical position of the rotation axis 320. Similarly, it is to be appreciated that the rotation axis 348 of pattern roll 340 is shown in FIG. 9C relative to the rotation axes 330*a*, 332*a* of the first and second disks 330, 332 only to illustrate the canting angle θ therebetween and does not represent the actual physical position of the rotation axis 348.

With continued reference to FIGS. 9B and 9C, the respective rims 330*b*, 332*b* of the first and second disks 330, 332 may each be contoured to define a pick-up surface 368 and a drop-off surface 370. In turn, the pick-up surfaces 368 may be oriented to define a relatively constant gap G1 extending for a distance along the cross direction CD between the pick-up surface 368 and the outer circumferential surface 318 of the anvil roll 308 at or near the nip 328. In some configurations, the pick-up surfaces 368 may be parallel or substantially parallel with the outer circumferential surface 318 of the anvil roll 308 at or near the nip 328. In addition, the drop-off surfaces 370 may be oriented to define a relatively constant gap G2 extending for a distance along the cross direction CD between the drop-off surfaces 370 and the outer circumferential surface 346 of the pattern roll 340 at or near the nip 338. In some configurations, the drop-off surfaces 370 may be parallel or substantially parallel with the outer circumferential surface 346 of the pattern roll 340 at or near the nip 338. It is to be appreciated that the rims 330*b*, 332*b* of the disks 330, 332 may be configured such that the pick-up surfaces 368 may be positioned axially inboard or outboard in the cross direction of the drop-off surfaces 370. In addition, the pick-up surface 368 may be angularly offset from the drop-off surface 370 by an offset angle Φ. In some configurations, the offset angle may be defined such that:

$$\Phi=[180°-2\times(\text{canting angle }\theta)].$$

In operation, the discrete elastic part 200 may be transferred from the anvil roll 308 at the nip 328 to position the first end region 234 of the discrete elastic part 200 on the pick-up surface 368 of the first disk 330 and to position the second end region 236 of the discrete elastic part 200 on the pick-up surface 368 of the second disk 332. As the disks 330, 332 rotate, the first end region 234 of the discrete elastic part 200 will become positioned on the drop-off surface 370 of the first disk 330 and the second end region 236 of the discrete elastic part 200 will become positioned on the drop-off surface 370 of the second disk 332 due to the canted orientations of the disks 330, 332. Thus, the discrete elastic part 200 is transferred from the drop-off surfaces 370 of the disks 330, 332 to the outer circumferential surface 346 of the pattern roll 340 at the nip 338.

It is to be appreciated that the contoured features of the rims 330*b*, 332*b* of the disks 330, 332 described above may be incorporated as integrated features of the disks 330, 332 or may be incorporated into discrete parts, such as shoes, that may be connected with disks 330, 332. In addition, it is to be appreciated that the rims 330*b*, 332*b* and/or shoes may be constructed from compliant materials, such as polyurethane or silicone. In some configurations, the rims 330*b*, 332*b* and/or shoes may, and may also include holding pins and/or may be constructed from materials with a relatively high coefficient of friction relative the discrete elastic parts 200.

It is also to be appreciated that aspects of the spreader mechanism 326 may be configured to be independently controlled. For example, the cross direction CD position of the spreader mechanism 326 relative to cutting device 304 and/or the bonding device 324. In addition, the cross direction CD positions of the disks 330, 332 of the spreader mechanism 326 may be adjustable relative to each other. In addition, canting angles of the disks 330, 332 of the spreader mechanism 326 may be adjustable. In some configurations, radial clearances between components of the cutting device 304 and/or the bonding device 324 and the outer rims of the first and second disks 330*b*, 332*b* of the spreader mechanism 326 may be adjustable, wherein the positions of the disks 330, 332 may be configured to be independently or collectively adjustable.

It is to be appreciated that various drives may be used to control the rotation of the disks 330, 332 of the spreader mechanism 326. For example, the disks 330, 332 of the spreader mechanism 326 may be driven by one or more motors, such as a servo motor. In some configurations, motors may be directly connected with the disks 330, 332, and in some configurations, motors may be indirectly connected with the disks 330, 332, such as through belts, pulleys, and/or gears. The disks 330, 332 may be driven as a pair through the use of a common driveshaft with a coupling between the disks. In some configurations, a common jackshaft may be used to drive both disks 330, 332 together with a single motor. In some configurations, drives of components of the cutting device 304 and/or the bonding device 324 and spreader mechanism 326 may be operatively connected, and may be configured with a single motor.

As discussed above, the cut discrete elastic parts 200 accelerate from the second speed S2 to the third speed S3 on the outer circumferential surface 318 of the anvil roll 308, and in some configurations, the third speed S3 may be less than or greater than the first speed S1 of the advancing carrier substrate 202. Thus, the transfer device 322 may be configured to rotate at a variable angular velocity to accelerate or decelerate the discrete elastic parts 200 to the first speed S1. For example, if the third speed S3 is less than the first speed S1, the transfer device 322 may be configured to receive the discrete elastic part 200 from the anvil roll 308 while the rims 330*b*, 332*b* of the first and second disks 330, 332 are moving through the nip 328 at the third speed S3. The angular velocity of the disks 330, 332 may then be changed to accelerate the discrete elastic part 200 to the first speed S1 before transferring the discrete elastic part 200 to the bonding device 324. In another example, if the third speed S3 is greater than the first speed S1, the angular velocity of the disks 330, 332 may be changed to decelerate the discrete elastic part 200 to the first speed S1 before transferring the discrete elastic part 200 to the bonding device 324. In situations where the third speed S3 is equal to the first speed S1, the disks 330, 332 may rotate at a constant angular velocity. It is to be appreciated that the spreader mechanism 326 may be configured in various ways to accommodate a need to rotate at variable angular velocities, such as, for example, disclosed in European Patent Publication No. EP 2260813 B1, which is incorporated by reference herein. The ability to rotate at the transfer device 326 at variable angular velocities may help reduce the need to replace components of the apparatus 300 when assembling absorbent articles 100 of smaller or larger sizes, which in turn, may require a reduction or increase in the pitch distances between consecutively cut discrete elastic parts 200.

As previously mentioned, the rotatable transfer device 322 may be configured to transfer the discrete elastic parts 200 from the cutting device 304 to a bonding device 324. As shown in FIGS. 2, 7, and 8, the bonding device 324 may be positioned adjacent the first and second disks 330, 332 of the spreader device 326 to define a nip 338 therebetween. In some configurations, the first and second disks 330, 332 may be configured to apply positive air pressure, sometimes referred to as blow-off air, to the discrete elastic part 200 adjacent the nip 338 to help remove the discrete elastic parts 200 from the disks 330, 332 during transfer to the bonding device 324. As discussed in more detail below, the discrete elastic parts 200 are received from the spreader mechanism 326 with the central regions 238 stretched in the cross direction CD, and the bonding device 324 transfers and bonds the discrete elastic parts 200 in the stretched state to the advancing carrier substrate 202.

It is to be appreciated that the bonding device 324 may be configured in various ways. For example, as shown in FIGS. 2, 7, and 8, the bonding device 324 may be configured with a pattern roll 340 and a pressing surface 342 adjacent the pattern roll 340 to define a nip 344 therebetween. The pattern roll 340 includes an outer circumferential surface 346 and rotates about an axis of rotation 348, wherein the pattern roll 340 may rotate in a fourth direction Dir4 that is opposite the third direction Dir3. In addition, pattern roll 340 may rotate such that the outer circumferential surface 346 advances at or about the first speed S1. During operation, discrete elastic parts 200 in a stretched state are transferred from the first and second disks 330, 332 to the outer circumferential surface 346 of the pattern roll 340. The pattern roll 340 rotates to advance the stretched elastic parts 200 between the outer circumferential surface 346 of the pattern roll and the advancing carrier substrate 202. In particular, the first surface 218 of the discrete elastic part 200 may be positioned in a facing relationship with and in direct contact with the outer circumferential surface 346 of the pattern roll 340. As such, the zone 240 of adhesive 222 and the second surface of the discrete elastic part 200 may be facing radially outward from the rotation axis 348. The carrier substrate 202 advances to the pattern roll 340 such that the first surface 210 of the carrier substrate 200 is in direct contact with and in a facing relationship with the outer circumferential surface 346 of the pattern roll 340. As the pattern roll 340 rotates, the second surface 220 of the discrete elastic part 200 is positioned in direct contact with and in a facing relationship with the first surface 210 of the carrier substrate 200. The combined discrete elastic part 200 and the carrier substrate 202 advance through the nip 344 between the pattern roll 340 and the pressing surface 342 to mechanically bond the discrete elastic part 200 and the carrier substrate 202 together.

Figures 11, 11A, 13, 14:
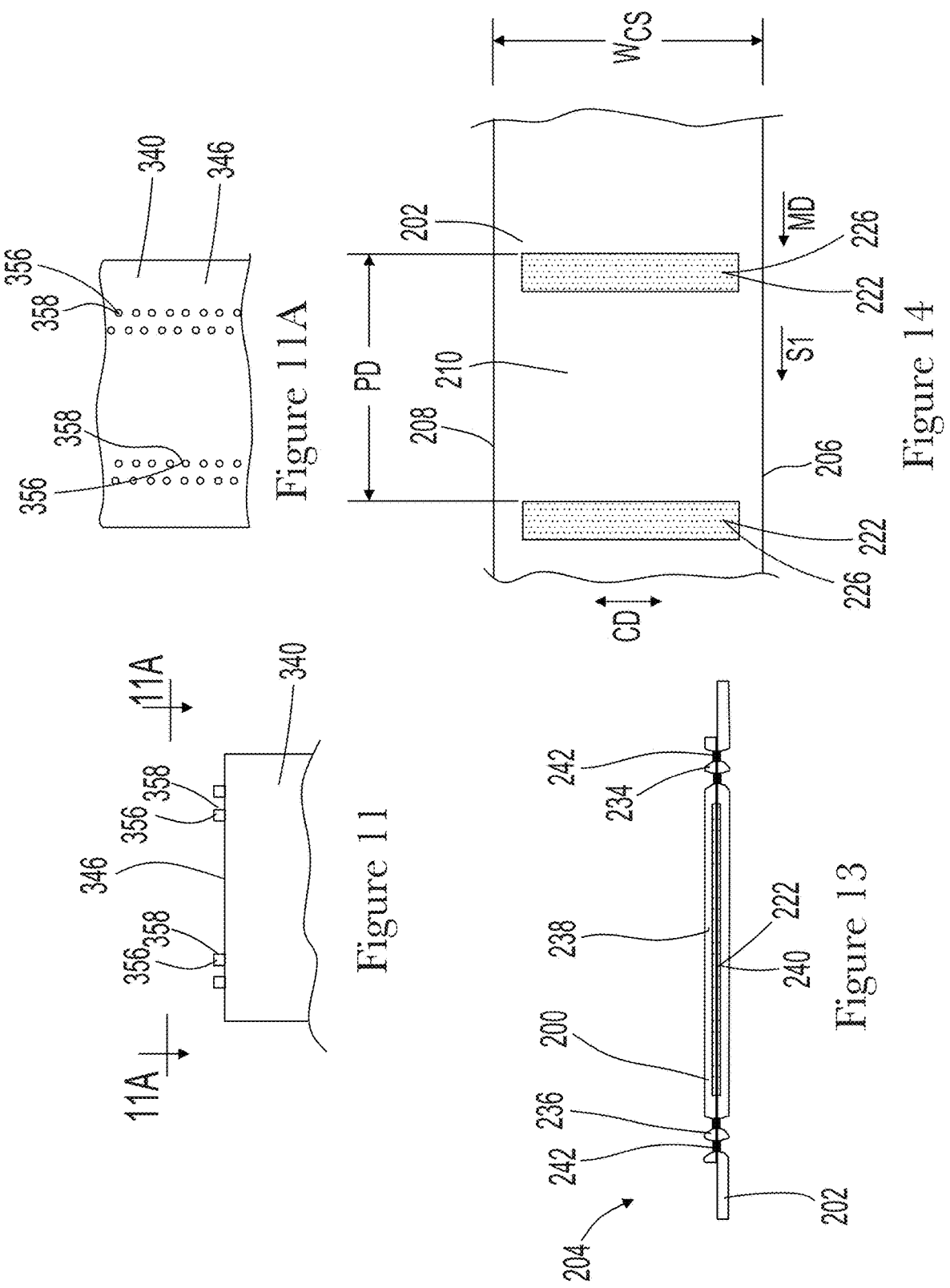
FIG. 11 is a detailed cross sectional view of a pattern roll from FIG. 7 showing bonding elements extending radially outward from an outer circumferential surface taken along line 10-10.
FIG. 11A is a detailed view of a portion of the outer circumferential surface of the pattern roll showing bonding elements from FIG. 11 taken along line 11A-11A.
FIG. 13 is a view of the laminate including the elastic part and the carrier substrate taken along section 13-13 in FIG. 12.
FIG. 14 is a view of the carrier substrate and adhesive taken along section 14-14 in FIG. 2.

For example, as shown in FIG. 2, the bonding device 324 may be configured as a mechanical bonding device that includes an anvil roll 350. The anvil roll 350 may include an outer circumferential surface 352 and rotates about an axis of rotation 354, wherein the anvil roll 350 may rotate in a fifth direction Dir5 that is opposite the fourth direction Dir4. The outer circumferential surface 352 of the anvil roll 350 may define the pressing surface 342 operating in conjunction with the pattern roll 340. As shown in FIGS. 11 and 11A, the outer circumferential surface 346 of the pattern roll 340 may also comprise one or more bonding surfaces 356 defined by bonding elements 358 extending radially outward. As the pattern roll 340 rotates, the discrete elastic parts 200 and the carrier substrate 200 are advanced between the bonding surfaces 356 and the pressing surface 342 to mechanically bond or weld the elastic part 200 and the carrier substrate 202 together to create bonds 242 between the elastic part 200 and the carrier substrate 202. Heat and/or pressure between the pressing surface 342 and the pattern roll 340 may melt and bond the carrier substrate 202 and the elastic part 200 together in areas supported by the bonding surfaces 356 on the pattern roll 340. As shown in FIG. 12, the mechanical bonds and/or bond regions 242 may have shapes that correspond with and may mirror shapes of the bonding surfaces 356.

Thus, as the laminate 204 advances through the nip 344, the carrier substrate 202 and the discrete elastic part 200 are mechanically bonded or welded together. It is to be appreciated that the bonding device 324 herein may be configured in various ways with various features described herein to bond the discrete elastic parts 200 with the carrier substrate 202. As such, the pattern roll 340 and/or anvil roll 350 may be configured to apply heat and pressure in various ways to perform mechanical bonding, such as for example, the mechanical bonding devices and methods disclosed in in U.S. Pat. Nos. 4,854,984; 6,248,195; 8,778,127; 9,005,392; 9,962,297; and 10,052,237. It is also to be appreciated that the positions of the pattern roll 340 and anvil roll 350 may be opposite to that which is illustrated in FIG. 2, and as such, the discrete elastic parts 200 may be transferred from the transfer device 322 to the outer circumferential surface 352 of the anvil roll 350 as opposed to the pattern roll 340. It is also to be appreciated that one or more components of the bonding device 324 may be configured to operate at constant and/or variable speeds. For example, the pattern roll 340 and/or the anvil roll 350 may be connected with various types of motors, such as servo motors for example, that may rotate the pattern roll 340 and/or the anvil roll 350 at constant and/or variable angular velocities.

In some configurations, the carrier substrate 202 may be partially wrapped around the outer circumferential surface 346 of the pattern roll 340. As such, the bonding device 324 may include one or more rolls that help guide the carrier substrate 202 to and/or from the pattern roll 340. For example, as shown in FIG. 2, the bonding device may include a guide roll 360 that helps to guide the carrier substrate 202 onto the outer circumferential surface 346 of the pattern roll 340 downstream of the nip 338 where the elastic parts 202 are received from the transfer device 322 and upstream of the nip 344 between the pattern roll 340 and the pressing surface 342. The guide roll 360 may also be configured to apply pressure against the carrier substrate 202 and the elastic part 200 to help enhance the bonding of the adhesive 222 of the adhesive zone 240 and the carrier substrate 202.

It is to be appreciated that the bonding device 324 may be configured in various ways, such as with heated or unheated pattern rolls, anvil rolls and/or ultrasonic bonding devices. For example, the bonding device 324 schematically shown in FIG. 2A may include the pattern roll 340 and the pressing surface 342 that comprises an energy transfer surface 362 of an ultrasonic bonding device 364. As such, the bonding device 364 may include a horn 366 and may be configured to impart ultrasonic energy to the combined elastic part 200 and the carrier substrate 202 on the pattern roll 340.

It is to be appreciated that aspects of the ultrasonic bonding device 364 may be configured in various ways, such as for example linear or rotary type configurations, and such as disclosed for example in U.S. Pat. Nos. 3,113,225; 3,562,041; 3,733,238; 5,110,403; 6,036,796; 6,508,641; and 6,645,330. In some configurations, the ultrasonic bonding device 364 may be configured as a linear oscillating type sonotrode, such as for example, available from Herrmann Ultrasonic, Inc. In some configurations, the sonotrode may include a plurality of sonotrodes nested together in the cross direction CD. It is also to be appreciated that rotary horns may also be configured to rotate at constant and/or variable angular velocities.

As discussed above, the pattern roll 340 includes bonding elements 358 that extend radially outward to define bonding surfaces 356. In turn, the bonds and/or bond regions 242 between the discrete elastic part 200 and the carrier substrate 202 may have shapes that correspond with and may mirror shape of the bonding surfaces 356. It is to be appreciated that the pattern roll 340 may have various quantities and/or shapes of bonding surfaces 356 and that such bonding surfaces 356 may be positioned in various locations on the pattern roll 340. For example, as shown in FIGS. 11, 11A, 12, and 13, the bonding elements 358 and bonding surfaces 356 may be positioned to correspond with the first end region 234 and the second end region 236 of the discrete elastic part 200. Thus, the bonding device 340 may operate to mechanically bond the first and second end regions 234, 236 of the elastic part 200 without mechanically bonding the stretched central region 238. In some configurations, the bonding elements 358 and bonding surfaces 356 may be positioned such that mechanical bonds 242 are also applied to bond the central region 238 of the discrete elastic part 200 and the carrier substrate 202 together.

The pattern roll 340 may also be configured to apply vacuum pressure to the discrete elastic parts 200 to help hold the discrete elastic parts 200 on the outer circumferential surface 346 as the pattern roll 340 rotates. The vacuum pressure may also help hold the discrete elastic parts 200 in the stretched state while positioned on the pattern roll 340. In addition, the bonding elements 358 and bonding surfaces 356 may also help grip the elastic parts 200 and help hold the elastic parts 200 in the stretched state. In addition, the pattern roll 340 may be configured such to also apply vacuum pressure through the bonding surfaces 356 of the bonding elements 358. Further, the pattern roll 340 may be configured to interface with the first and second disks 330, 332 of the spreader mechanism 326 to help maintain the stretched state of the discrete elastic part 200 during the transfer to the pattern roll 340 at the nip 338. For example, as discussed above, the disks 330, 332 of the spreader mechanism 326 may include various quantities of nubs 336 that protrude radially outward from the rims 330b, 332b, wherein the nubs 336 may help prevent the first and second end regions 234, 236 of the elastic parts 200 from sliding toward each other along the rims 330b, 332b while stretching the discrete elastic parts 200. It is to be appreciated that the nubs 336 may be configured in various shapes and sizes, spacing, and may be constructed from various types of materials. In some configurations, the bonding elements 358 on the pattern roll 340 may be configured to intermesh with the nubs 336 protruding from the rims 330b, 332b of the first and second disks 330, 332. The intermeshing between the nubs 336 and the bonding elements 358 may help the apparatus 300 maintain the stretched state of the discrete elastic part 200 when transferring from the transfer device 322 to the bonding device 324.

As shown in FIG. 2, after the discrete elastic part 200 is bonded with the carrier substrate 202 to create the laminate 204, the laminate 204 may continue to advance in the machine direction MD from the bonding device 324 and may be subjected to additional converting operations, such as cutting, folding, and/or packaging operations. In some configurations, the laminate 204 may define a continuous length of absorbent articles or may be combined with additional substrates and/or components to define a continuous length of absorbent articles. In turn, the continuous length of absorbent articles may be subjected to a final knife cut that separates discrete absorbent articles from the continuous length of absorbent articles. As previously mentioned, the discrete elastic parts 200 may correspond with waistbands 158 on the absorbent articles 100 and the carrier substrate 202 may correspond with a topsheet substrate 138 or backsheet substrate 136. In some configurations, the apparatuses and methods herein may be configured to apply discrete elastic parts 200 as discrete front and/or back waistbands 158. In some configurations, the discrete elastic parts 200 may be applied to the carrier substrate 202, and the discrete elastic parts 200 are subsequently cut during the final knife cut operation into a front waistband 158 positioned in the front waist region 116 and a back waistband 158 positioned in the back waist region 118. It is to be appreciated that such final knife cut operation may be configured to apply straight and/or curved cut lines through the carrier substrate 202 and discrete elastic parts 200. It is also to be appreciated that the carrier substrate 202 may include parts, such as laterally extending side panels for example, attached thereto upstream of the bonding device 324. As such, the system 300 may also include devices, such as rails and/or conveyors, to help guide and control the carrier substrate 202, and specifically such laterally extending features, into the bonding device 324 to help prevent unintentional bonding of such features.

Figures 4A, 5A:
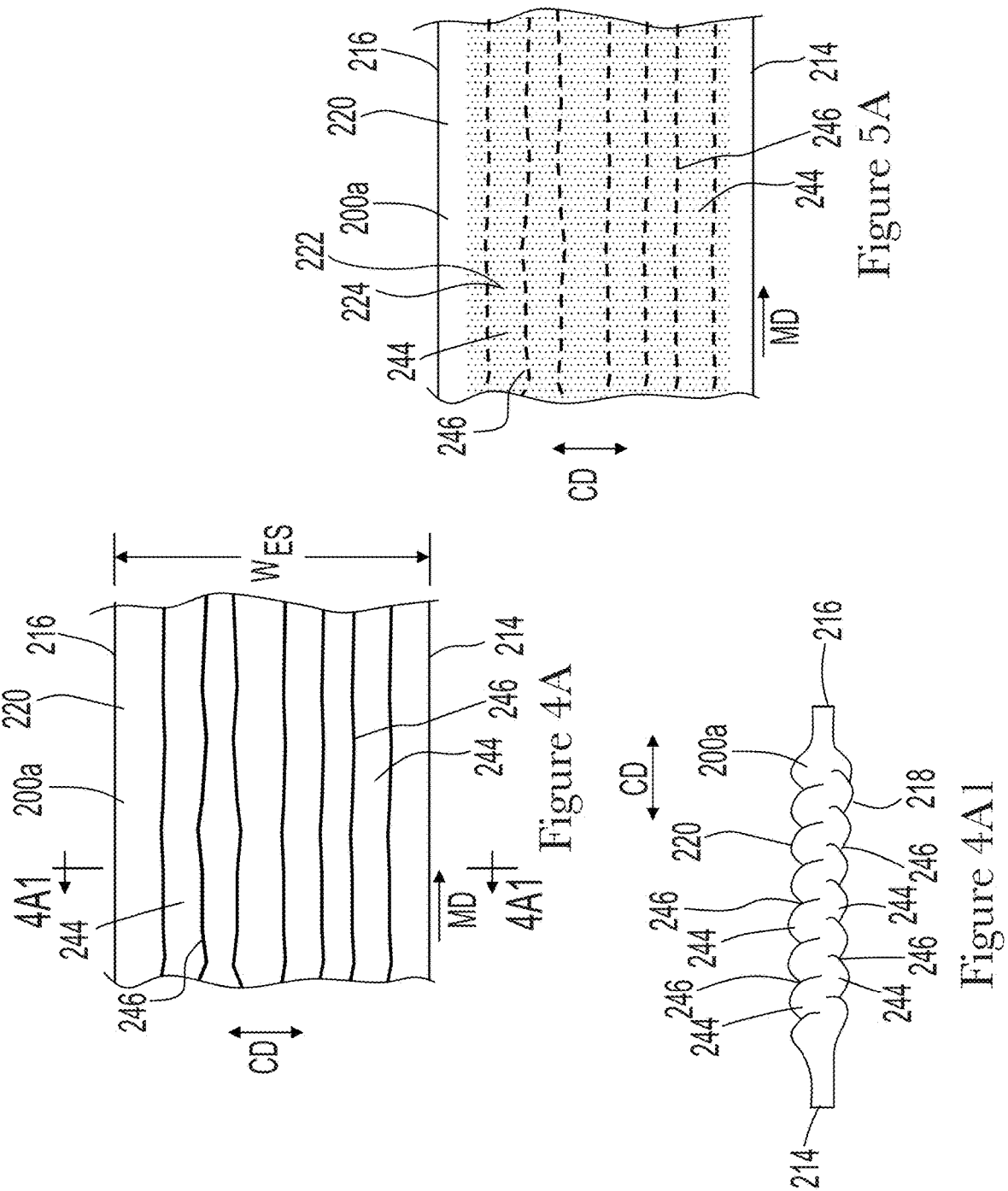
FIG. 4A is a view of a continuous elastic substrate with corrugations and corrugation lines taken along section 4-4 in FIG. 2.
FIG. 5A is a view of a continuous elastic substrate with a continuous region of adhesive covering corrugations taken along section 5-5 in FIG. 2.
Figure 6A:
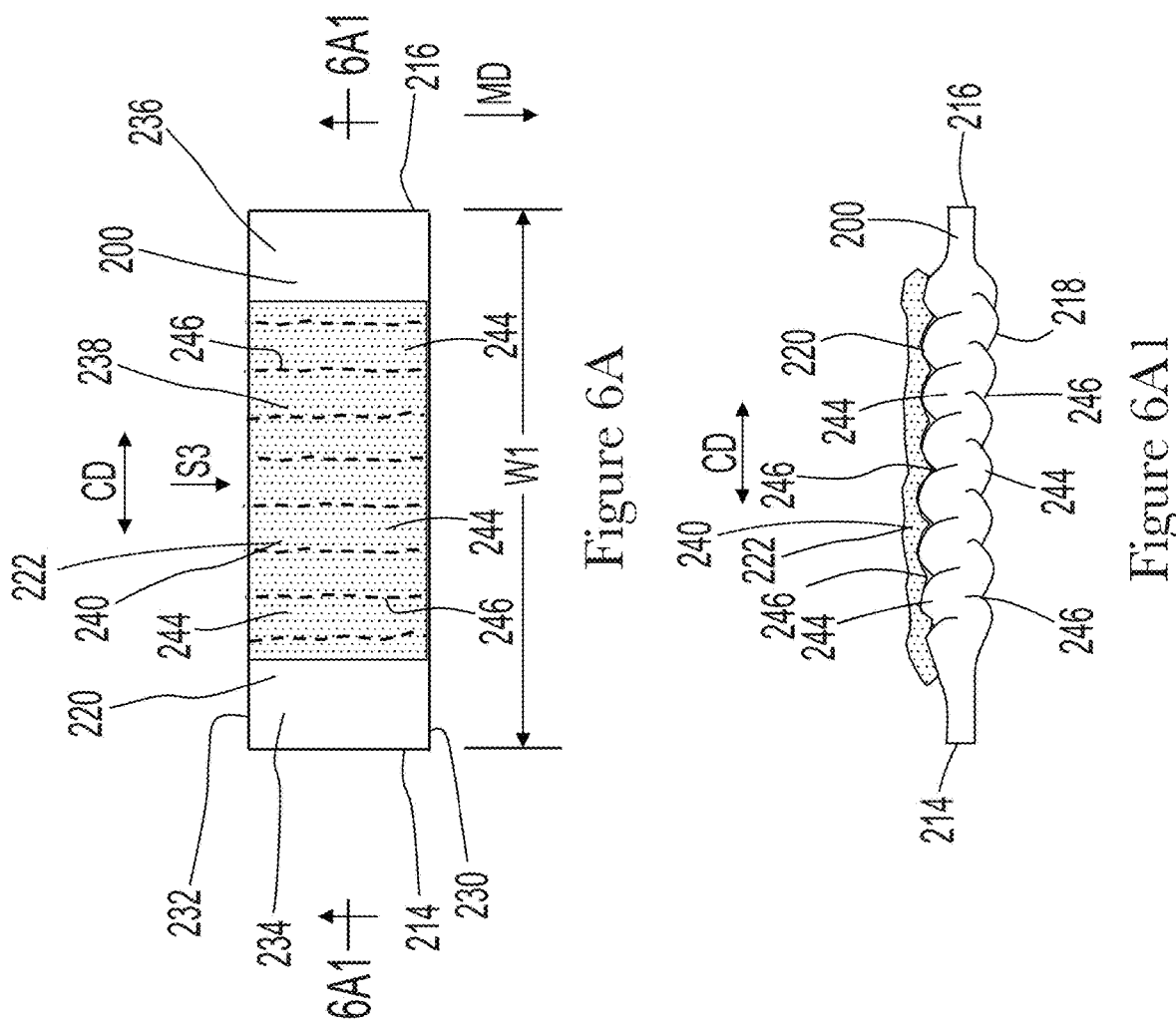
FIG. 6A is a view of a discrete elastic part laid out flat with corrugations, corrugation lines, and a zone of adhesive taken along section 6-6 in FIG. 2.
Figure 10A:
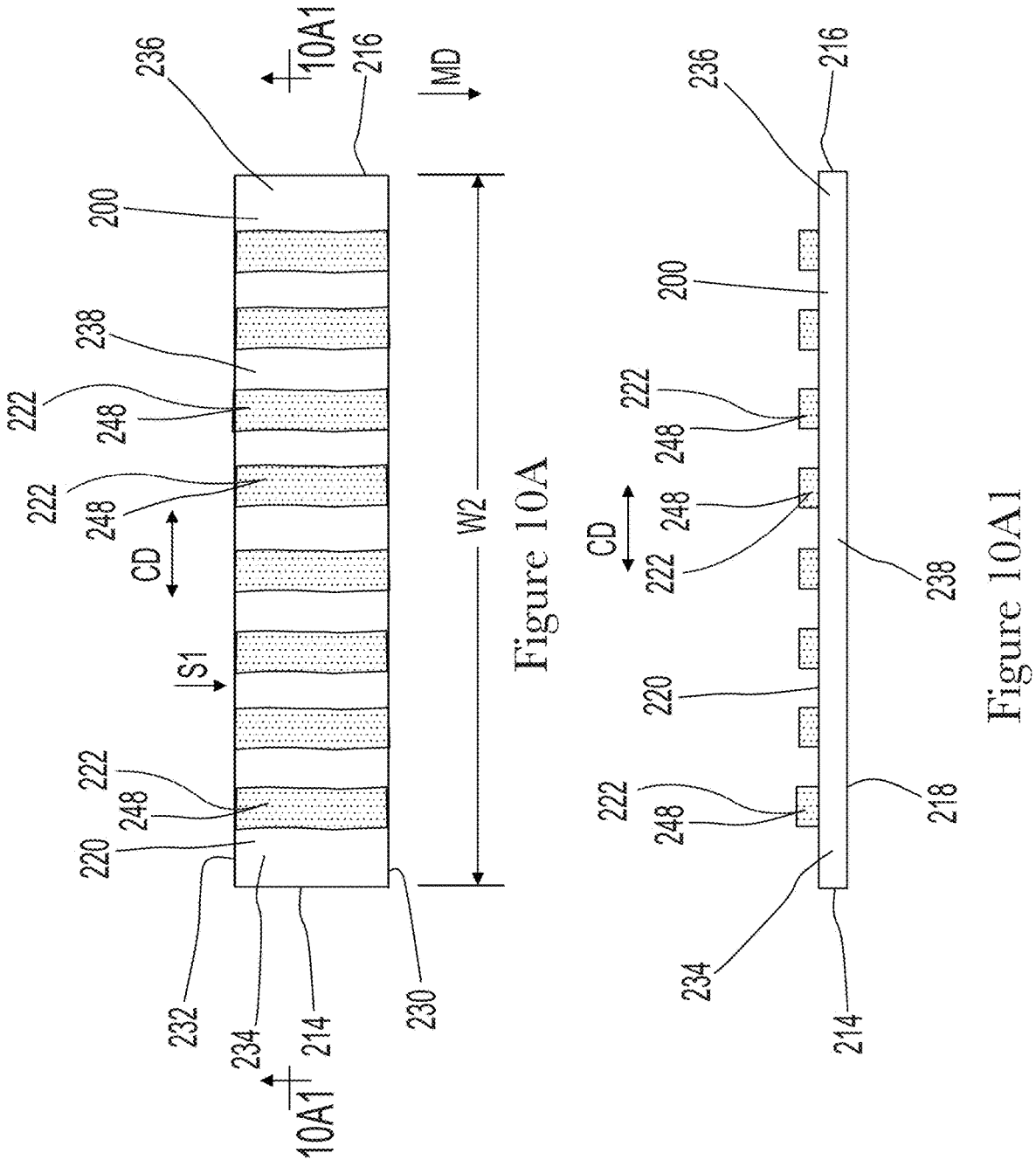
FIG. 10A is a view of a stretched discrete elastic part laid out flat with the zone of adhesive separated into stripes of adhesive taken along section 10-10 in FIG. 2.

As discussed above, the discrete elastic parts may be combined with the carrier substrate with adhesive and/or mechanical bonds. It is to be appreciated that the adhesive and mechanical bonds may be configured in various ways. For example, as discussed above with reference to FIGS. 2, 4, 5, and 6, the continuous elastic substrate 200a may define a width $W_{ES}$ in the cross direction CD, and the discrete elastic part 200 may also define a first width W1 in the cross direction CD upstream of the nip 328 between the cutting device 304 and the transfer device 322. And the respective widths $W_{ES}$, W1 of the continuous elastic substrate 200a and the elastic part 200 may be unstretched widths or partially stretched widths. Thus, as shown in for example FIGS. 4A and 4A1, the continuous elastic substrate 200a may comprise corrugations 244 oriented so as to define corrugation lines 246 extending in the machine direction MD. As discussed above with reference to FIG. 2 and as shown in FIG. 5A, adhesive 222 may be applied to the second surface 220 of the continuous elastic substrate 200a. The cutting device 304 separates the discrete elastic part 200 from the continuous elastic substrate 200a. Thus, as shown in FIGS. 6A and 6A1, the discrete elastic part 200 may also comprise corrugations 244 oriented to define corrugation lines 246 extending in the machine direction MD. In addition, the elastic part 200 includes a zone 240 of adhesive 222 that may cover corrugations 244 on the second surface 220 of the discrete elastic part 200, such as shown in FIGS. 6A and 6A1. Thus, the zone 240 of adhesive 222 may be separated into individual stripes 248 of adhesive 222 when the central region 238 of the discrete elastic part 200 is stretched in the cross direction CD, as shown in FIGS. 10A and 10A1. The individual stripes 248 of adhesive 222 may extend in the machine direction MD and may be separated from each other in the cross direction CD by areas of the second surface 220 of the elastic part 200 the do not include adhesive 222. In turn, the stretched central region 238 of the discrete elastic part 200 may then be bonded with the carrier substrate 202 with the stripes 248 of adhesive 222.

Figure 12A:
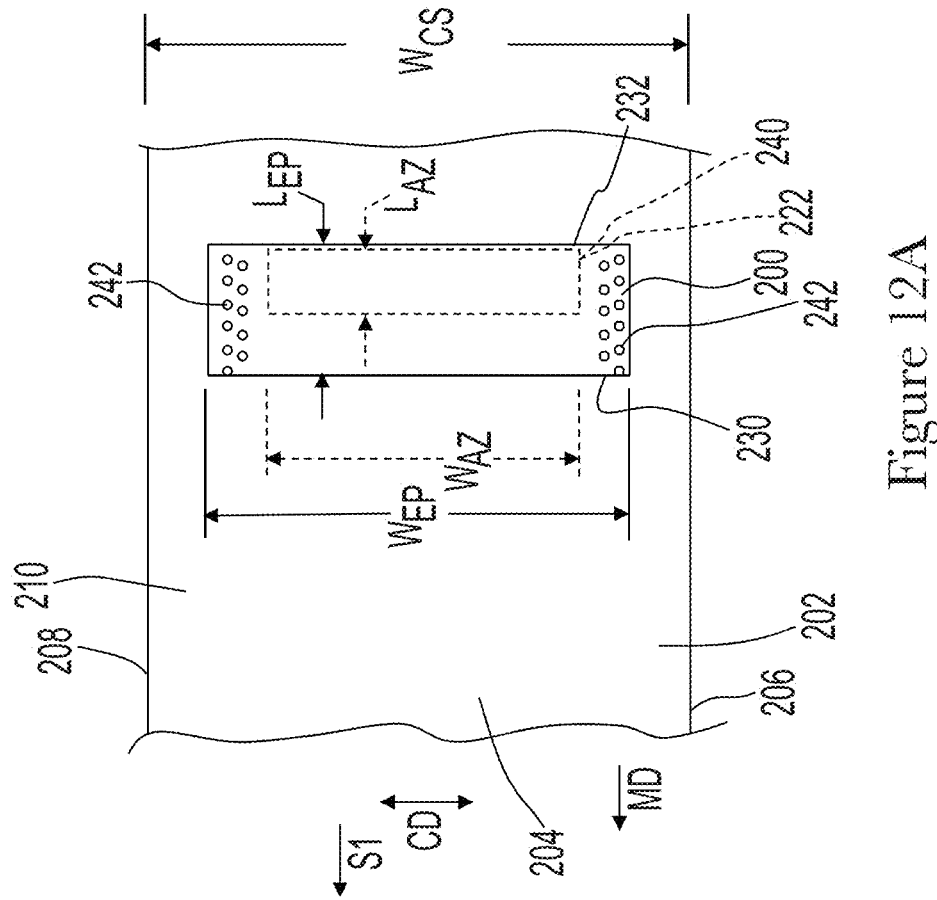
FIG. 12A is a view of the laminate including the elastic part and the carrier substrate with a zone of adhesive that extends for a length less than a length of the elastic part.

It is also to be appreciated that the zone 240 of adhesive 222 may be applied to define various different shapes and sizes with respect to the discrete elastic part 200 and/or the carrier substrate 202. For example, as shown in FIG. 12, the zone 240 of adhesive 222 may extend in the cross direction CD to be coterminous with both the leading edge 230 and the trailing edge 232 of the elastic part 200, and the zone 240 of adhesive 222 may define a length $L_{AZ}$ in the machine direction MD and a width $W_{AZ}$ in the cross direction CD. As such, the length $L_{AZ}$ of the zone 240 of adhesive 222 may extend the entire length $L_{EP}$ of the discrete elastic part 200 extending from the leading edge 230 to the trailing edge 232. In some configurations such as shown in FIG. 12A, the length $L_{AZ}$ of the zone 240 of adhesive 222 may extend for less than the entire length $L_{EP}$ of the discrete elastic part 200. As such, the zone 240 of adhesive 222 may extend in the cross direction CD to be coterminous with the leading edge 230 and/or the trailing edge 232 of the elastic part 200 and may extend for length $L_{AZ}$ extending from either the leading edge 230 or the trailing edge 232 of the elastic part 200.

Figure 12B:
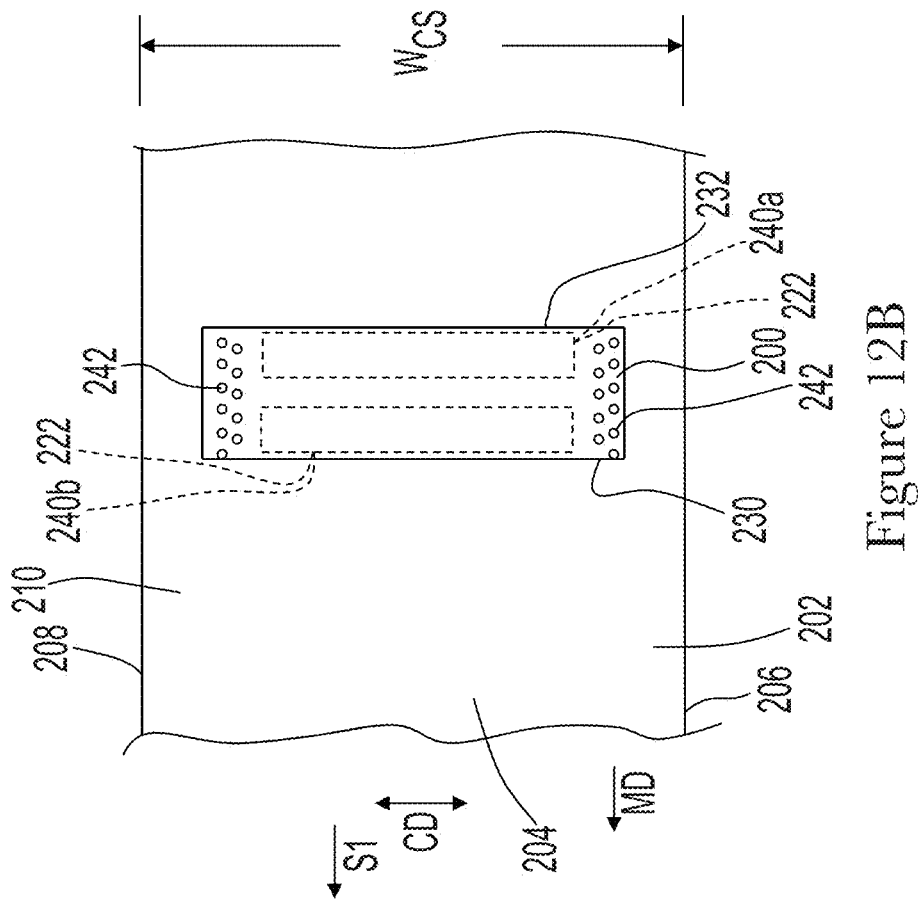
FIG. 12B is a view of the laminate including the elastic part and the carrier substrate with a plurality of zones of adhesive.

In some examples, the zone 240 of adhesive 222 may not extend to either the leading edge 230 or the trailing edge 232 of the elastic part 200. In some configurations, more than one zone 240 of adhesive 222 may bond the elastic part 200 with the carrier substrate 202. For example, as shown in FIG. 12B, the laminate 204 may include a first zone 240a of adhesive and a second zone 240b of adhesive 240b that bond the elastic part 200 with the carrier substrate 202. Such zones 240a, 240b of adhesive 222 may be separated from each other in the cross direction CD and/or the machine direction MD.

It is to be appreciated that the elastic part 200, carrier substrate 202, the zone 240 of adhesive 222, and the mechanical bonds and/or bond regions 242 may define various features with various sizes relative to each other. For example, as shown in FIG. 12, the elastic part 200 bonded with the carrier substrate 202 may define a width $W_{EP}$ extending in the cross direction CD from the first longitudinal edge 214 to the second longitudinal edge 216. As such, the width $W_{EP}$ of the elastic part 200 may equal to or less than the $W_{CS}$ of the carrier substrate. The width $W_{AZ}$ of the zone 240 of adhesive 222 may be equal to or less than the width $W_{EP}$ of the elastic part 200.

As previously mentioned, the bonding device 340 may operate to mechanically bond the first and second end regions 234, 236 of the elastic part 200 with the carrier substrate 202. As such, the mechanical bonds 242 may define bond zones wherein the laminate 204 of the elastic part 200 and carrier substrate 202 may or may not be elastic. For example, as shown in FIG. 12, a first bond zone $B_{Z1}$ may extend from the mechanical bonds 242 located in the first end region 234 of the elastic part 200 to first longitudinal edge 214 of the elastic part 200, and a second bond zone $B_{Z2}$ may extend from the mechanical bonds 242 located in the second end region 236 of the elastic part 200 to second longitudinal edge 216 of the elastic part 200. The first bond zone $B_{Z1}$ may define a width $W_{BZ1}$ in the cross direction CD, and the second bond zone $B_{Z2}$ may define a width $W_{BZ2}$ in the cross direction CD, wherein the widths $W_{BZ1}$ and $W_{BZ2}$ may be equal or different. As shown in FIG. 12, a corrugation zone $C_Z$ may be defined in the cross direction CD between the first bond zone $B_{Z1}$ and the second bond zone $B_{Z2}$ wherein the laminate 204 of the elastic part 200 and carrier substrate 202 is elastic. The corrugation zone $C_Z$ may define a width $W_{CZ}$ in the cross direction CD when in a fully stretched state, such as shown in FIG. 12.

In some configurations, the first bond zone $B_{Z1}$ and/or the second bond zone $B_{Z2}$ may be separated in the cross direction CD from the zone 240 of adhesive 222. For example, as shown in FIG. 12, the first bond zone $B_{Z1}$ may be separated in the cross direction CD from the zone 240 of adhesive 222 to define a first gap zone $G_{Z1}$, and the second bond zone $B_{Z2}$ may be separated in the cross direction CD from the zone 240 of adhesive 222 to define a second gap zone $G_{Z2}$. The first gap zone $G_{Z1}$ may define a width $W_{GZ1}$ in the cross direction CD, and the second gap zone $G_{Z2}$ may define a width $W_{GZ2}$ in the cross direction CD, wherein the widths $W_{GZ1}$ and $W_{GZ2}$ may be equal or different. In some configurations, the first width $W_{GZ1}$ and/or the second width $W_{GZ2}$ may be from about 2 mm to about 4 mm. In some configurations, the first bond zone $B_{Z1}$ and/or the second bond zone $B_{Z2}$ may be coterminous with the zone 240 of adhesive 222, wherein the first width $W_{GZ1}$ and/or the second width $W_{GZ2}$ may be 0 mm. In some configurations, portions of the first bond zone $B_{Z1}$ and/or the second bond zone $B_{Z2}$ may be located inside the zone 240 of adhesive 222. In some configurations, portions of the first bond zone $B_{Z1}$ and/or the second bond zone $B_{Z2}$ may be located laterally outward from the first longitudinal edge 214 and/or the second longitudinal edge 216.

As discussed above with reference to FIG. 2, the system 300 may include an adhesive applicator device 302 that may be configured to apply adhesive 222 to the continuous elastic substrate 200a upstream of the nip 310 between the knife roll 306 and anvil roll 308. In turn, the discrete elastic parts 200 separated from the continuous elastic substrate 200a may include a zone 240 of adhesive 222 that is adapted to adhesively bond the elastic part 200 with the carrier substrate 202. It is to be appreciated that the zone 240 of adhesive 222 may comprise adhesive 222 applied to the continuous elastic substrate 200a, the elastic part 200, and/or the carrier substrate 202 in various configurations and/or positions in the assembly process. For example, as shown in FIG. 2, the system 300 may include an adhesive applicator device 302a that may be configured to apply adhesive 222 to the discrete elastic part 200 at a position downstream of the nip 310 between the knife roll 306 and anvil roll 308. In another example, shown in FIG. 2, the apparatus 300 may include an adhesive applicator device 302b that deposits adhesive 222 onto the first surface 210 of the carrier substrate 202 to define the zone 240 of adhesive 222 that bonds the elastic part 200 with the carrier substrate 202. It is to be appreciated that the adhesive applicator device 302a may be configured to operate in addition to or in place of the adhesive applicators 302, 302b, and adhesive applicator device 302b may be configured to operate in addition to or in place of the adhesive applicators 302, 302a. It is also to be appreciated that the adhesive applicator devices 302a, 302b may be configured in various ways, such as the adhesive applicator 302 described above, such as for example, as a spray nozzle and/or a slot coating device. It is also to be appreciated that in some configurations, the discrete elastic parts 200 may be combined with the carrier substrate 202 with only mechanical bonds and without the use of adhesive.

In accordance with the above discussion with regard to the various shapes and sizes of the zones 240 of adhesive 222, it is to be appreciated that adhesive 222 may be applied to the continuous elastic substrate 200a and/or the carrier substrate 202 in various ways to define the zones 240 of adhesive 222. For example, as discussed above with reference to FIGS. 2 and 5, adhesive 222 may be applied to the continuous elastic substrate 200a to define a region 224 of adhesive 222 extending continuously in the machine direction MD and/or the cross direction CD.

Figures 5B, 5C:
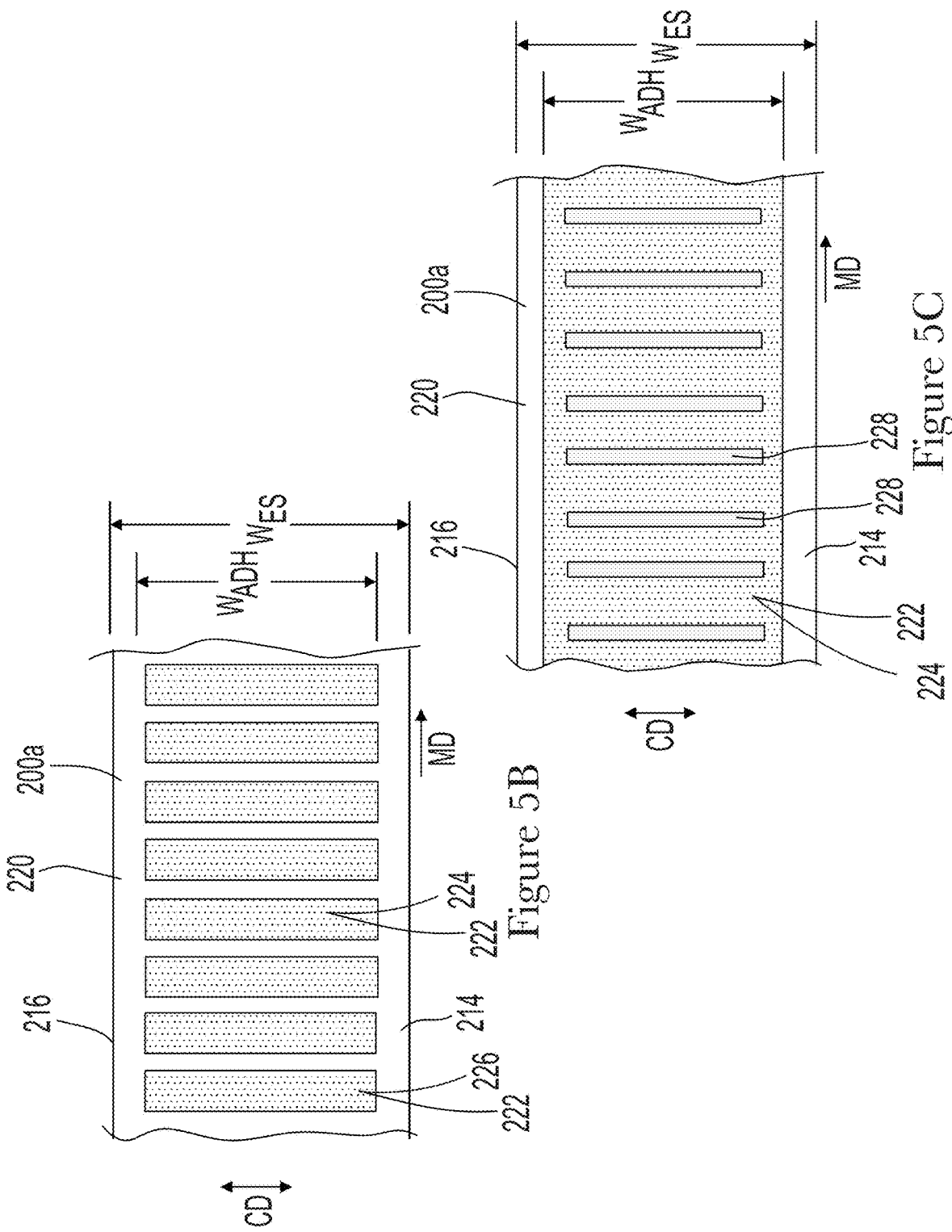
FIG. 5B is a view of a continuous elastic substrate with discrete patches of adhesive taken along section 5-5 in FIG. 2.
FIG. 5C is a view of a continuous elastic substrate with a continuous region of adhesive surrounding discrete areas without adhesive taken along section 5-5 in FIG. 2.

In another example, shown in FIG. 5B, the adhesive 222 may be applied to the second surface 220 of the continuous elastic substrate 200a in discrete patches 226 separated from each other in on the continuous elastic substrate 200a in the machine direction MD. In yet another example, shown in FIG. 5C, the adhesive 222 may be applied to the second surface 220 of the continuous elastic substrate 200a to define a region 224 of adhesive 222 that surround discrete areas 228 on the continuous elastic substrate 200a where no adhesive is applied. In still another example, shown in FIG. 14, the adhesive 222 may be applied to the first surface 210 of the carrier substrate 202 in discrete patches 226 separated from each other on the carrier substrate 202 in the machine direction MD. It is to be appreciated that adhesive 222 may be applied to the continuous elastic substrate 200a, the elastic part 200, and/or the carrier substrate 202 in shapes and sizes that define the zones 240 of adhesive 222 that bond the elastic parts 200 and the carrier substrate 202 together. The discrete patches 226 of adhesive 222 may be separated from each other on the carrier substrate 202 in the machine direction MD by the pitch distance PD.

It is to be appreciated that the continuous elastic substrate 200a and the discrete elastic parts 200 herein may be configured in various ways and may include one or more elastic materials, such as for example, elastic film and/or strands. For example, the continuous elastic substrate 200a and the discrete elastic parts 200 may be configured as a single layer of elastic film. In some configurations, the continuous elastic substrate 200a and the discrete elastic parts 200 may be configured as a laminate of two more substrates. For example, the continuous elastic substrate 200a and the discrete elastic parts 200 may be configured as an elastic film bonded in between two or more nonwoven substrates and/or may be bonded with one or more nonwoven substrates. For example, the continuous elastic substrate 200a and the discrete elastic parts 200 may be configured as a bi-laminate with an elastic film bonded with a single nonwoven substrate. In another example, the continuous elastic substrate 200a and the discrete elastic parts 200 may be configured as an elastic film bonded between two or more substrates, wherein the substrates may comprise nonwovens. It is also to be appreciated that nonwoven substrates of the elastic substrate 200a and discrete elastic parts 200 may be of the same or different material and/or basis weights. In some configurations, one more nonwoven substrates of the elastic substrate 200a and discrete elastic parts 200 may be of the same or different material and/or basis weights as one more nonwoven substrates of the carrier substrate 202.

It is also to be appreciated that the continuous elastic substrate 200a and the discrete elastic parts 200 may be assembled in various ways, such as for example, as disclosed in U.S. Pat. Nos. 6,572,595; 6,830,800; 7,087,287; and 7,803,244; and U.S. Patent Publication Nos. 2018/0042778 A1; 2018/0042787 A1; 2018/0042779 A1; and 2018/0042780 A1, which are all incorporated by reference herein. For example, FIGS. 15A-15D show various schematic views of an apparatus 500 operating to assemble a continuous elastic substrate 200a from which the discrete elastic parts 200 may be cut from, such as discussed above.

Figure 15A:
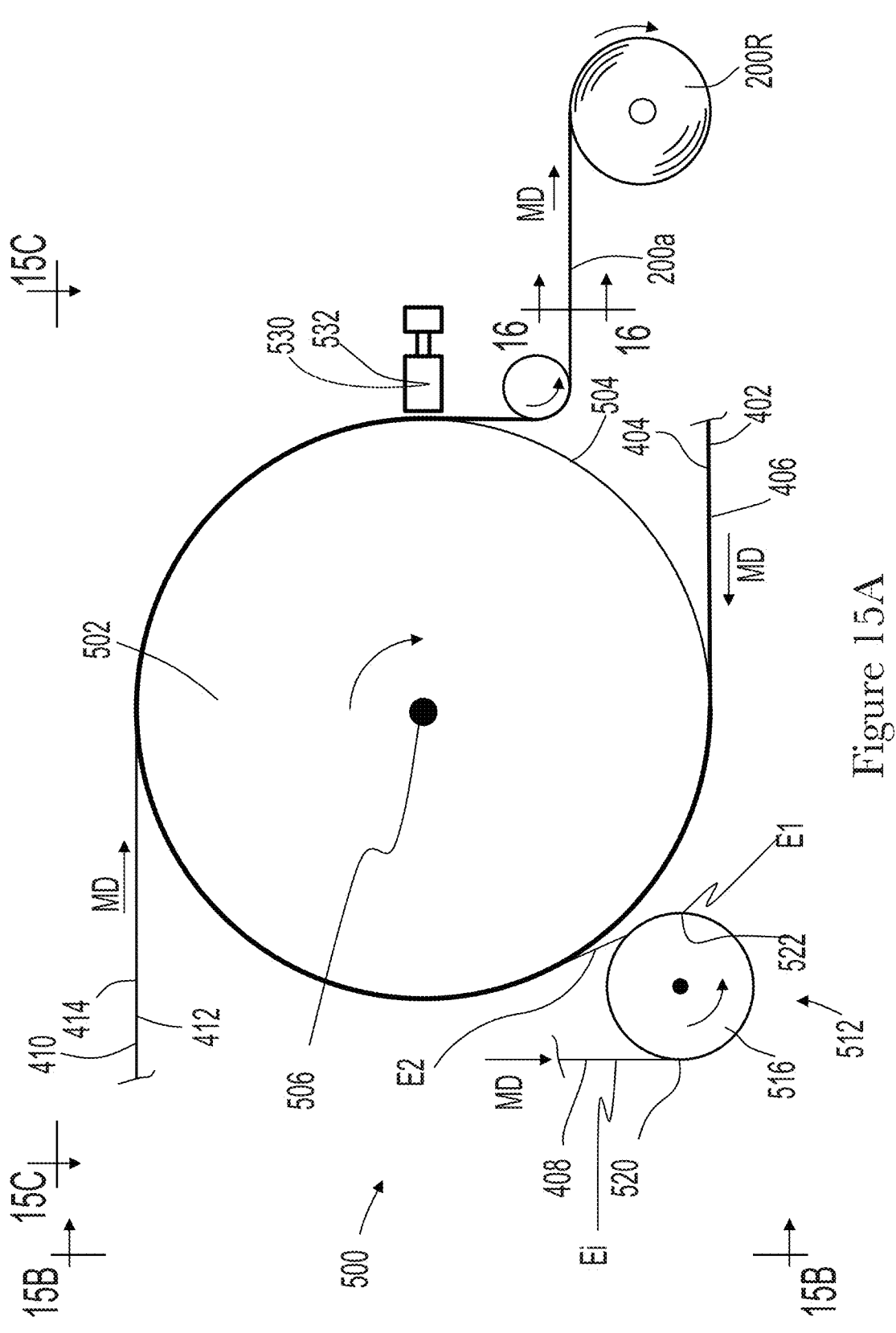
FIG. 15A is a schematic side view of an apparatus operating to assemble an elastic substrate.
Figure 15B:
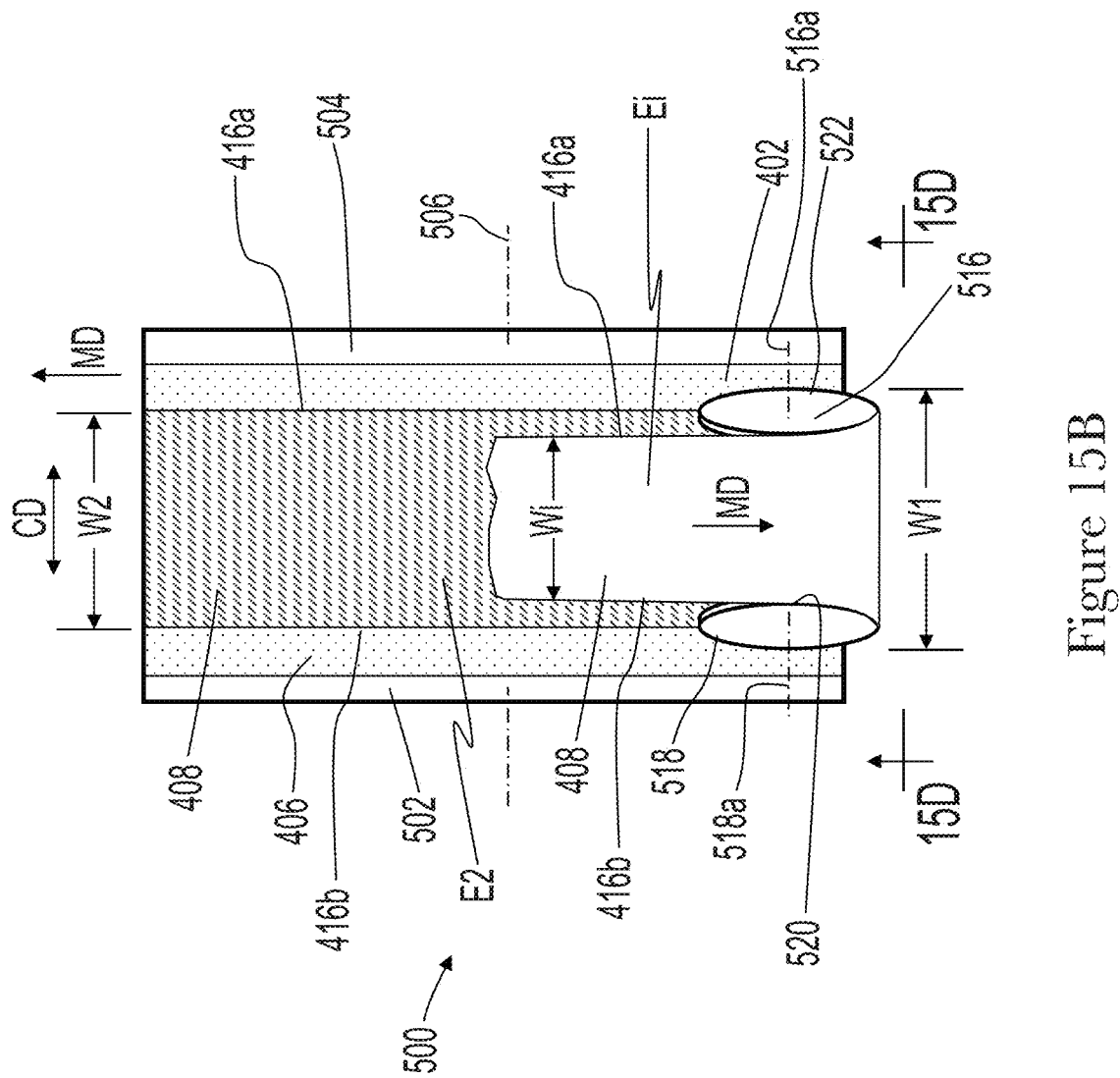
FIG. 15B is a left side view of the apparatus from FIG. 15A taken along line 15B-15B.
Figure 15C:
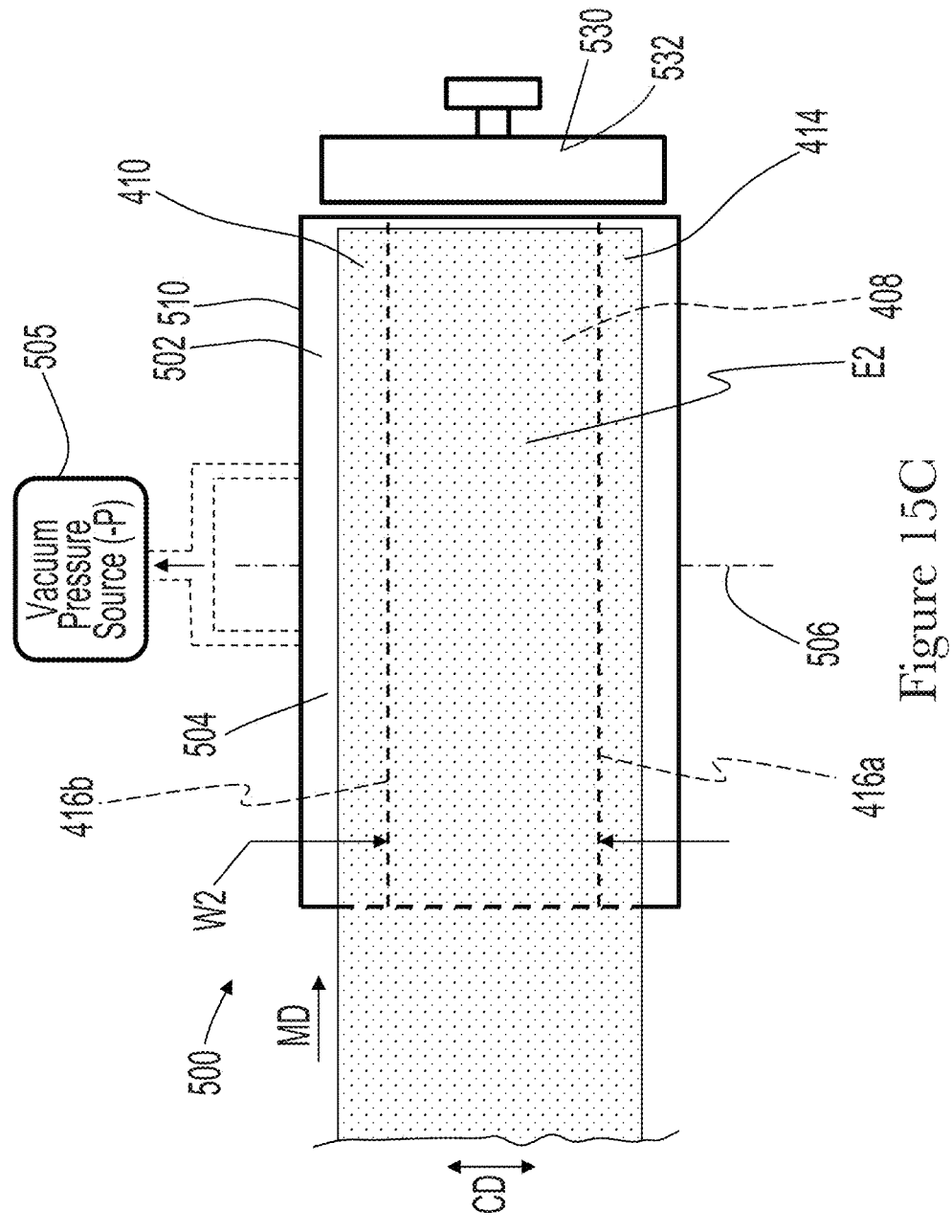
FIG. 15C is a top side view of the apparatus from FIG. 15A taken along line 15C-15C.

As shown in FIGS. 15A-15C, a first substrate 402 advances in a machine direction MD onto a rotating anvil 502. More particularly, the first substrate 402 includes a first surface 404 and an opposing second surface 406, and the first substrate 402 advances to wrap the first surface 404 onto an outer circumferential surface 504 of the rotating anvil 502. During the assembly process, a spreader mechanism 512 stretches an elastic film 408 by stretching the elastic film 408 to a first elongation in the cross direction CD. And the stretched elastic film 408 is positioned into contact with the second surface 406 of the first substrate 402. In turn, the elastic substrate 200a may be formed by ultrasonically bonding the first substrate 402 and the elastic film 408 together with a second substrate 410 on the anvil 502. More particularly, the second substrate 410 includes a first surface 412 and an opposing second surface 414, and the second substrate 410 advances to position the first surface 412 in contact with the elastic film 408 and the second surface 406 of the first substrate 402.

With continued reference to FIGS. 15A-15C, as the anvil 502 rotates, the first substrate 402, the elastic film 408, and the second substrate 410 are advanced between the outer circumferential surface 504 of the anvil 502 and one or more ultrasonic devices 530 adjacent the anvil 502. It is to be appreciated that the ultrasonic device 530 may include a horn 532 and may be configured to impart ultrasonic energy to the combined substrates and elastic films on the anvil 502. It is to be appreciated that aspects of the ultrasonic bonding device 530 may be configured in various ways, such as for example linear or rotary type configurations, and such as disclosed for example in U.S. Pat. Nos. 3,113,225; 3,562,041; 3,733,238; 5,110,403; 6,036,796; 6,508,641; and 6,645,330. In some configurations, the ultrasonic bonding device 530 may be configured as a linear oscillating type sonotrode, such as for example, available from Herrmann Ultrasonic, Inc. In some configurations, the sonotrode may include a plurality of sonotrodes nested together in the cross direction CD. In turn, the ultrasonic horn 532 bonds the first substrate 404, the elastic film 408, and the second substrate 410 together to form the elastic substrate 200a.

Figures 16, 17:
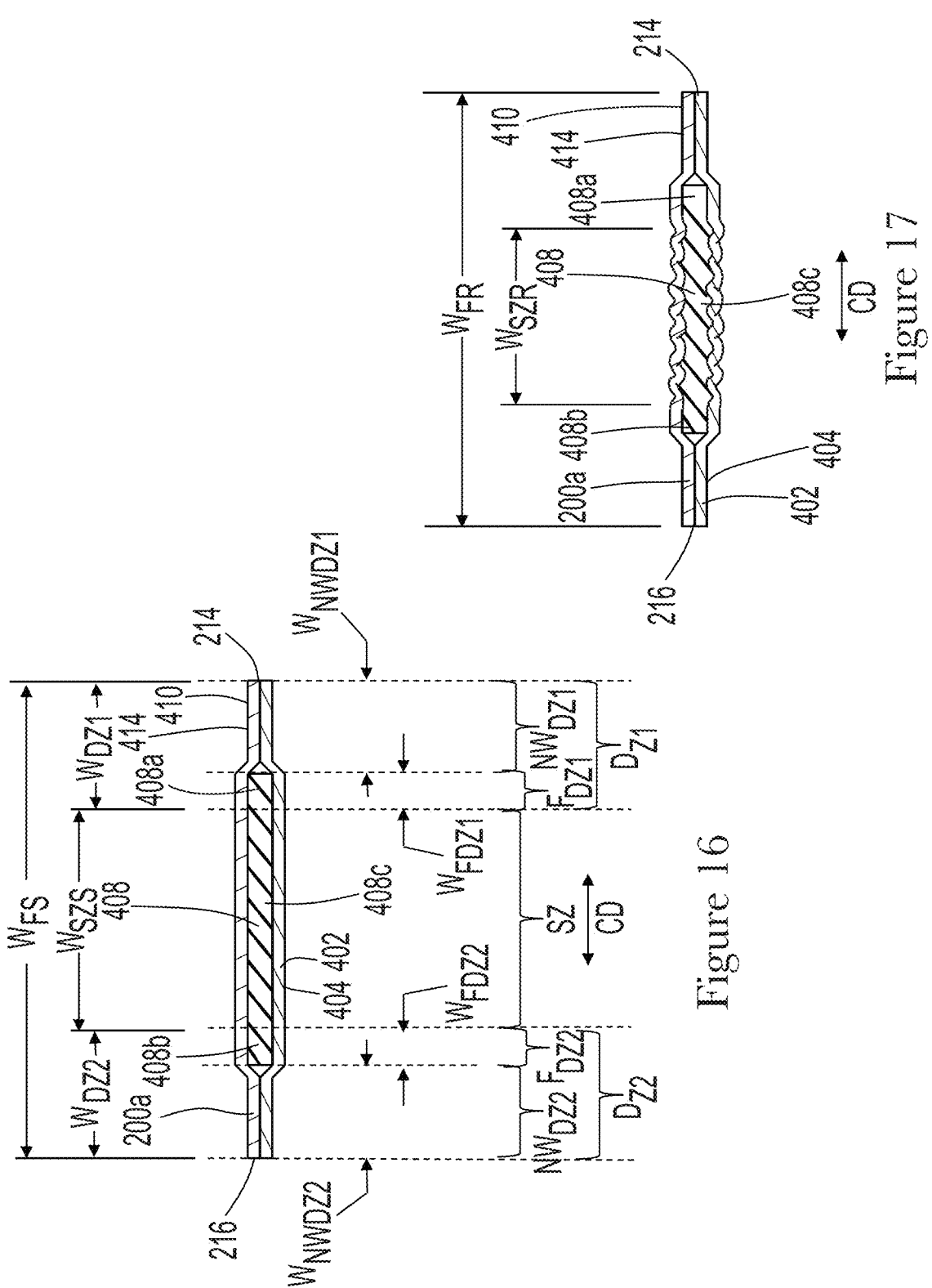
FIG. 16 is a cross sectional view of the elastic substrate from FIG. 15A taken along line 16-16.
FIG. 17 is a cross-sectional view of the elastic substrate from FIG. 16 in a relaxed, contracted condition.

As shown in FIGS. 15A and 16, the elastic substrate 200a may then advance from the anvil 502 and may be accumulated, such as for example, by being wound onto a roll 200R or being festooned in a container. It is to be appreciated that the elastic substrate 200a may be wound onto a roll 200R in a fully stretched, partially stretched, or fully relaxed state. The accumulated elastomeric substrate 200a may be stored and/or moved to a location for incorporation into an absorbent article assembly process wherein the elastomeric substrate 200a may be converted into an absorbent article component, such as discussed above. It is also to be appreciated that the elastic substrate 200a may advance from the anvil 502 and directly to absorbent article assembly processes. FIG. 17 also shows the elastic substrate 200a in a relaxed state wherein the central region 408c of the elastic film 408 is contracted in the cross direction CD. It is to be appreciated that the apparatus 500 may be configured to assemble elastic substrates 200a with a single lane of elastic film 408 and may also be configured to assemble elastic substrates 200a with multiple lanes of elastic film 408 separated from each other in the cross direction. In turn, the elastic substrate 200a may be cut along the machine direction MD between such lanes of elastic films 408 to create multiple individual elastic substrates 200a.

During the ultrasonic bonding process, it is to be appreciated that bonds imparted into the elastic substrate 200a from the ultrasonic horn 532 may correspond with patterns and/or shapes defined by a plurality of pattern elements extending radially outward from the outer circumferential surface 504 of the anvil 502. It is to be appreciated that the elastic substrate 200a may include various portions of components bonded together in various ways and with differing or identical bond patterns. For example, the elastic film 408 may be bonded together with the first and/or second substrates 402, 410, and the first substrate 402 may be bonded directly to the second substrate 410 in areas of the elastic substrate 200a. In some configurations, the first and second substrates 402, 410 may be bonded directly to each other through apertures in the elastic film, wherein such apertures may be formed during the bonding process. In some configurations, the elastic film 408 can be involved, or participate, in the bonding between the first and second substrates 402, 410, wherein "involved" can mean that the elastic film can, to some extent, be in intimate contact with, and possibly partially merged with, one or both the first and second substrates 402, 410. The involvement may be due to actual melt bonding about the perimeter of a bond site or may be due to mechanical interaction, such as by entanglement of a fibrous elastic layer between fibrous nonwoven layers also about the perimeter of bond site. It is to be appreciated that the apparatus 500 may be adapted to create various types of bond configurations, such as disclosed, for example, in U.S. Pat. Nos. 6,572,595; 6,830,800; 7,087,287; and 7,803,244; and U.S. Patent Publication Nos. 2018/0042778 A1; 2018/0042787 A1; 2018/0042779 A1; and 2018/0042780 A1, which are all incorporated by reference herein.

Figure 15D:
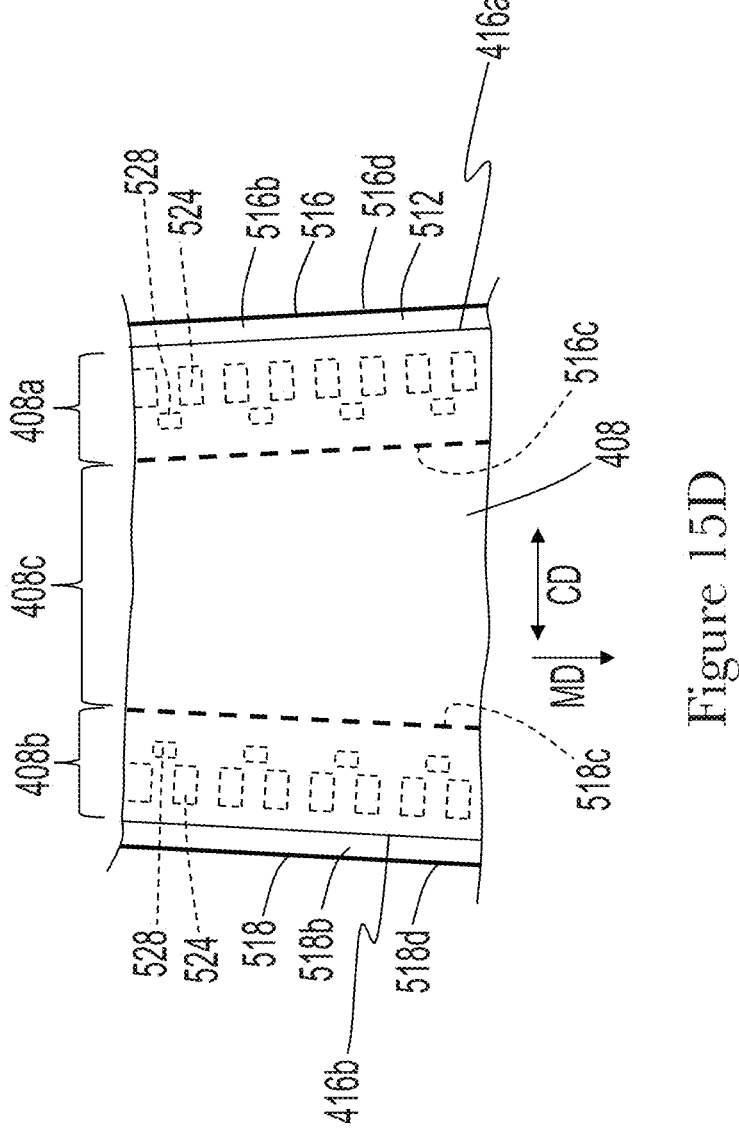
FIG. 15D is a detailed view of an elastic material advancing on a spreader mechanism from FIG. 15B taken along line 15D-15D.

As previously mentioned, the spreader mechanism 512 stretches the elastic film 408 to a first elongation E1 in the cross direction CD. With particular reference to FIGS. 15A and 15D, the elastic film 408 includes a first edge 416a and a second edge 416b separated from the first edge 416a in the cross direction CD. In addition, the elastic film 408 includes a first edge region 408a adjacent the first edge 416a and a second edge region 408b adjacent the second edge 416b. The first edge region 408a is separated from the second edge region 408b in the cross direction CD by a central region 408c. As shown in FIGS. 15A and 15B, the elastic film 408 may define an initial width W1 in the cross direction CD between the first edge 416a and the second edge 416b upstream of the spreader mechanism 512. The elastic film 512 advances in a machine direction MD onto the spreader mechanism 512 at a first location 520. It is to be appreciated that elastic film 408 may be at the initial width W1 in the cross direction CD while advancing onto the spreader mechanism 512. It is also to be appreciated that the elastic film 408 may be in a relaxed state upstream of the spreader mechanism 512.

As shown in FIGS. 15B and 15D, the first edge region 408a of the elastic film 408 advances onto an outer rim 516b of a first disk 516 of the spreader mechanism 512, and the second edge region 408b advances onto an outer rim 518b of a second disk 518. In addition, the outer rim 516b of the first disk 516 may extend axially between an inner edge 516c and an outer edge 516d, and the outer rim 518b of the second disk 518 may extend axially between an inner edge 518c and an outer edge 518d. The outer rims 516b, 518b of the first and second disks 516, 518 of the spreader mechanism 512 may include channels 524 fluidly connected to a vacuum pressure source and may include radially protruding nubs 528. Thus, as shown in FIG. 15D, the first edge region 408a of the elastic film 408 may be held in position on the outer rim 516b with vacuum air pressure in the channels 524 and with the radially protruding nubs 528. Similarly, the second edge region 408b of the elastic film 408 may be held in position on the outer rim 518b with vacuum air pressure in the channels 524 and with the radially protruding nubs 528.

With continued reference to FIGS. 15B and 15D, the first disk 516 and the second disk 518 are canted. Thus, as the first disk 516 and the second disk 518 of the spreader mechanism 512 rotate, the elastic film 408 is stretched in the cross direction CD while advancing from the first location 520 or downstream of the first location 520 toward a second location 522. Thus, as shown in the FIGS. 15A, 15B, and 15D, the spreader mechanism 512 may stretch the elastic film 408 in the cross direction CD from the initial width W1 (and an initial elongation Ei) to a first width W1 (and a first elongation E1) in the cross direction CD, wherein W1 is greater than W1 and wherein E1 is greater than Ei. In some configurations, the elastic film 408 may be consolidated to a second width W2 (and second elongation E2), wherein W2 is less than W1 and wherein E2 is less than E1. It is to be appreciated that the elastic film 408 remains stretched at the second width W2 (and second elongation E2). It is also to be appreciated that the elastic film 408 may be in a relaxed state at the initial width W1 (and initial elongation Ei), and as such, the second width W2 may be greater than the initial width W1 and the second elongation E2 may be greater than the initial elongation Ei. In configurations where the elastic film is not consolidated, W2 may be equal to W1 and E2 may be equal to E1.

It is to be appreciated that the apparatuses 500 herein may be configurated to operate with various extensions of elastic film. In some configurations, the difference between the first elongation E1 and the second elongation E2 may be about 25%. In some configurations, E1–E2=25%. In some configurations, when the spreader mechanism includes canted disks, the first and second edge regions 408a, 408b of the elastic film 408 may be held in position on the outer rims 516b, 518b of the disks 516, 518. And as such, some portions of the first and second edge regions 408a, 408b may remain unstretched in the cross direction CD as the first and second disks 516, 518 rotate. Thus, as the first disk 516 and the second disk 518 of the first spreader mechanism 512 rotate, the central region 408c of the elastic film 408 is stretched in the cross direction CD.

As shown in FIG. 15A-15D, the elastic film 408 advances from the spreader mechanism 512 downstream of the second location 522 to the anvil 502, and onto the second surface 406 of the first substrate 402 on the anvil 502. And as the anvil 502 rotates, the second substrate 410 advances onto anvil 502 to position the first surface 412 in contact with elastic film 408 and the second surface 406 of the first substrate 402 to form an elastic substrate 200a and the first substrate 402, elastic film 408, and second substrate 410 are bonded together.

With continued reference to FIGS. 15A and 15B, the outer circumferential surface 504 of the anvil 502 may be fluidly connected with a vacuum source 505, and as such, vacuum air pressure may be applied to the first substrate 402 on the anvil 502. For example, the outer circumferential surface 504 of the anvil roll 502 may include a plurality of apertures fluidly connected with the vacuum pressure source. When the first substrate 402 is configured as a porous substrate, such as a nonwoven, vacuum air pressure may also be applied to the elastic film 408 on the anvil 502, and as such, may help maintain the stretched condition of the of the elastic film 408 while on the anvil 502. In some configurations, adhesive on a nonwoven may also help decrease the porosity of the nonwoven, which in turn, may enhance the ability of the vacuum air pressure to help maintain components in a stretched state.

It is also to be appreciated that aspects of the spreader mechanisms 512 may be configured in various ways. For example, the cross direction CD positions of the disks 516, 518 of the spreader mechanism 512 may be adjustable relative to each other. In addition, canting angles of the disks 516, 518 of the spreader mechanism 512 may be adjustable. The canting angle of the first disk 516 may be defined as an angular offset between the axis of rotation 516a of the first disk 516 and the axis of rotation 506 of the anvil 502, and the canting angle of the second disk 518 may be defined as an angular offset between the axis of rotation 518a of the second disk 518 and the axis of rotation 506 of the anvil 502.

In some configurations, radial clearances between the outer circumferential surface 504 of the anvil 502 and the outer rims 516*b*, 518*b* of the first and second disks 516, 518 of the spreader mechanisms 512 may be adjustable, wherein the positions of the disks 516, 518 may be configured to be independently or collectively adjustable. In some configurations, the radial clearance between the outer circumferential surface 504 of the anvil 502 and the outer rims 516*b*, 518*b* may be zero or greater than zero.

It is to be appreciated that various drives may be used to control the rotation of the disks 516, 518 of the spreader mechanism 512. For example, the disks 516, 518 of the spreader mechanism 512 may be driven by one or more motors, such as a servo motor. In some configurations, motors may be directly connected with the disks 516, 518, and in some configurations, motors may be indirectly connected with the disks 516, 518, such as through belts, pulleys, and/or gears. The disks 516, 518 may be driven as a pair through the use of a common driveshaft with a coupling between the disks. In some configurations, a common jackshaft may be used to drive both disks 516, 518 together with a single motor. In some configurations, drives of the anvil 502 and spreader mechanism 512 may be operatively connected, and may be configured with a single motor. In some configurations, the disks 516, 518 of the spreader mechanism 512 may be driven only by the advancement of the elastic film 408. In some configurations, the disks 516, 518 of the spreader mechanism 512 may be driven by rotation of the anvil 502 or an infeed idler. Other drives may include surface driving through a jackshaft with a friction material in operative contact with disks 516, 518.

It is to be appreciated that elastic substrates may be characterized by the force for a given extension when used in a disposable absorbent article. The magnitude of the force required to extend the elastic substrate may vary between the first extension and subsequent extensions. In some configurations, the elastic substrate may include an elastic film that may comprise a base elastic film, such as a styrenic-block copolymer, and surface layers also known as skins. Such skins may help prevent interlayer adhesion when the elastic film is wound into a roll format for shipping and handling. In some configurations, the skins may be a polyolefin, which may be 0.5-5 microns thick. However, the polyolefin skins on the surface of the elastic film may cause the higher initial extension forces for an elastic substrate. As such, some manufacturers of films may apply processes to help reduce the initial extension force for a given displacement relative to subsequent extensions. For example, some manufactures of elastic films may apply a process, sometimes referred to as "activation," wherein the films are extended or stretched to create a plurality of cracks and tears in the skins at a microscopic scale. In turn, these cracks and tears may help reduce the skin contribution to the extension forces. In some configurations, activation operations are performed separate to the assembly process, such as for example, activating the films offline wherein the films may be stored until needed for production. For example, activation operations may be accomplished during the manufacture of the films, separately from converting lines that are dedicated to manufacturing elastic substrates that may be used in disposable absorbent articles. After manufacturing and activating the films, the films are delivered to the converting lines, such as in a form of continuous films wound onto a roll. As such, it is to be appreciated that the elastic film 408 may be supplied to a laminating process, such as discussed above with reference to FIGS. 15A-15D, having already been activated. In some configurations, the elastic film 408 may be activated during the laminating process that forms the elastic substrate 200*a*, such as disclosed for example, in U.S. Patent Publication No. 2018/0042780 A1, which is incorporated herein by reference. It is also to be appreciated that the elastic substrate 200*a* may be subjected to activation processes. In some configurations, the elastic film 408 and/or the elastic substrate 200*a* may be subjected to various types of activation processes, such as disclosed for example, in U.S. Pat. Nos. 4,116,892; 4,834,741; 5,143,679; 5,156,793; 5,167, 897; 5,422,172; 5,518,801; 7,824,594; 7,896,641; 8,062, 572; 8,118,801; and 9,687,580, and U.S. Patent Publication No. 20120143165 A1, which are all incorporated by reference herein.

As mentioned above, some portions of the first and second edge regions 408*a*, 408*b* of the elastic film 408 may remain unstretched in the cross direction CD when assembling the elastic substrate 200*a*. Thus, as shown in FIG. 16, the elastic substrate 200*a* may include a first film dead zone $F_{DZ1}$ and a second film dead zone $F_{DZ2}$ that may correspond with the unstretched regions of the elastic film 408. In addition, elastic substrate 200*a* may also include a first nonwoven dead zone $N_{WDZ1}$ and a second nonwoven dead zone $N_{WDZ2}$ that correspond with regions where the elastic film 408 is not positioned between the first substrate 402 and the second substrate 410. The first nonwoven dead zone $N_{WDZ1}$ may extend from the first longitudinal edge 214 of the elastic substrate 200*a* to the first film dead zone $F_{DZ1}$, and the second nonwoven dead zone $N_{WDZ2}$ may extend from the second longitudinal edge 216 of the elastic substrate 200*a* to the second film dead zone $F_{DZ2}$. With continued reference to FIG. 16, the elastic substrate 200*a* may include a stretch zone $S_Z$ located between the nonwoven dead zones $N_{WDZ1}$, $N_{WDZ2}$ and the film dead zones $F_{DZ1}$, $F_{DZ2}$. The elastic substrate 200*a* may be elastomeric in the cross direction CD in the stretch zone $S_Z$. As shown in FIGS. 16 and 17, the elastic substrate 200*a* may define a width $W_{FS}$ when fully stretched in the cross direction CD, and the elastic substrate 200*a* may define a width $W_{FR}$ when fully relaxed in the cross direction CD, wherein $W_{FR}$ is less than $W_{FS}$. Similarly, the stretch zone $S_Z$ may define a width $W_{SZS}$ when fully stretched in the cross direction CD, and the stretch zone $S_Z$ may define a width $W_{SZR}$ when fully relaxed in the cross direction CD, wherein $W_{SZR}$ is less than $W_{SZS}$.

As shown in FIG. 16, the first nonwoven dead zone $N_{WDZ1}$ may define a width $W_{NWDZ1}$ in the cross direction CD, and the second nonwoven dead zone $N_{WDZ2}$ may define a width $W_{NWDZ2}$ in the cross direction CD, wherein $W_{NWDZ1}$ may be equal to or different than $W_{NWDZ2}$. The first film dead zone $F_{DZ1}$ may define a width $W_{FDZ1}$ in the cross direction CD, and second film dead zone $F_{DZ2}$ may define a width $W_{FDZ2}$ in the cross direction CD, wherein $W_{FDZ1}$ may be equal to or different than $W_{FDZ2}$. In addition, the widths of the nonwoven dead zones $W_{NWDZ1}$, $W_{NWDZ2}$ may be equal to or different from the widths of the film dead zones $W_{FDZ1}$, $W_{FDZ2}$. In some configurations, the combination of the first nonwoven dead zone $N_{WDZ1}$ and the first film dead zone $F_{DZ1}$ may define a first dead zone $D_{Z1}$ of the elastic substrate 200*a*, and the combination of the second nonwoven dead zone $N_{WDZ2}$ and the second film dead zone $F_{DZ2}$ may define a second dead zone $D_{Z2}$ of the elastic substrate 200*a*. Thus, the first dead zone $D_{Z1}$ may define a width $W_{DZ1}$ in the cross direction CD that is equal to the sum of the width $W_{NWDZ1}$ and the width $W_{FDZ1}$, and/or the second dead zone $D_{Z2}$ may define a width $W_{DZ2}$ in the cross direction CD that is equal to the sum of the width $W_{NWDZ2}$ and the width $W_{FDZ2}$. In some configurations, the elastic substrate 200*a* may not include the first nonwoven dead zone $N_{WDZ1}$ and/or the second nonwoven dead zone $N_{WDZ2}$. As such, the first film dead zone $F_{DZ1}$ may define the first dead zone $D_{Z1}$ of the elastic substrate 200a, and the second film dead zone $F_{DZ2}$ may define a second dead zone $D_{Z2}$ of the elastic substrate 200a. Thus, the width $W_{DZ1}$ may be equal to the width $W_{FDZ1}$, and/or the width $W_{DZ2}$ may be equal to the width $W_{FDZ2}$.

It is to be appreciated the elastic substrate 200a, and elastic parts 200 cut therefrom, may be configured such that the width $W_{DZ1}$ of the first dead zone $D_{Z1}$ may be equal to or different from the width $W_{DZ2}$ of the second zone $D_{Z2}$. In some configurations, the width $W_{DZ1}$ of the first dead zone $D_{Z1}$ may be equal to, less than, or greater than width $W_{BZ1}$ of the first bond zone $B_{Z1}$ discussed above with reference to FIG. 12. In addition, the width $W_{DZ2}$ of the second dead zone $D_{Z2}$ may be equal to, less than, or greater than width $W_{BZ2}$ of the second bond zone $B_{Z2}$ discussed above with reference to FIG. 12.

As mentioned above, the elastic substrate 200a and elastic parts 200 may include nonwoven substrates that may be of the same or different material and/or basis weights. For example, the first substrate 402 and the second substrate 410 referred to above with reference to FIGS. 15A-17 may be configured as nonwoven substrates. As such, the first substrate 402 and the second substrate 410 of the elastic substrate 200a and elastic parts 200 may be the same or different types of nonwovens and/or may have the same or different basis weights. In addition, the carrier substrate 202 may include one or more nonwoven substrates. As such, the first substrate 402 and/or the second substrate 410 of the elastic substrate 200a and elastic parts 200 may be the same or different types of nonwovens and/or may have the same or different basis weights as a nonwoven substrate of the carrier substrate 202. In addition, the nonwoven substrates of elastic substrate 200a and elastic parts 200, such as the first substrate 402 and/or the second substrate 410 for example, may include nonwoven substrates having the same or different fiber orientations as a nonwoven substrate of the carrier substrate 202. In turn, the elastic part 200 configured as a waistband 158 and a carrier substrate 202 configured as a topsheet or backsheet in an absorbent article may each include nonwoven substrates that are the same or different types of nonwovens and/or may have the same or different basis weights and/or may have the same or different fiber orientations. Fiber orientations of a nonwoven substrate may affect stretch properties of the nonwoven substrate in different directions. For example, a nonwoven substrate may have a fiber orientation that causes the nonwoven to be relatively more extensible in the cross direction CD than in the machine direction MD. In some configurations, a nonwoven having a relatively low extensibility in the machine direction MD may be relatively easier to manipulate and/or guide when advancing in a machine direction MD though converting operations and/or assembly transformations.

It is also to be appreciated that the processes and/or apparatuses herein may be configured with additional features, such as splicing operations, to help avoid having to stop assembly process operations in order to replenish material supplies. In some configurations, the apparatuses 300 discussed herein may be configured to operate with apparatuses that are configured to provide an uninterrupted supply of continuous elastic substrate 200a. For example, during operation, a replacement supply of a continuous elastic substrate 200a may be spliced to a current supply of continuous elastic substrate 200a being used in assembly operations before the current supply is completely depleted.

It is to be appreciated that various types of splicing operations may be used to replenish the supply of a continuous elastic substrate 200a. For example, some splicing operations may be configured to apply a strip of splicing tape to connect a replacement continuous elastic substrate 200a to a nearly depleted elastic substrate 200a to help avoid supply interruptions. As discussed above, the continuous elastic substrate 200a may advance through a cutting device 304 that separates the continuous elastic substrate 200a into discrete elastic parts 200. In addition, a transfer device 322 and/or bonding device 324 may further subject the discrete elastic parts 200 to cross directional stretching and/or bonding operations. However, some splicing tape material may not be stretchable and/or may not be conducive to bonding operations. In turn, discrete elastic parts 200 connected with splicing tape may undesirably disrupt operations of stretching and/or bonding processes. As such, some apparatuses 300 may be configured to remove discrete elastic parts 200 with splicing tape attached thereto from assembly operations before such undesired process disruptions may occur. In some examples, splicing operations may be configured to utilize stretchable splicing tape and/or other materials more conducive to various assembly operations to help prevent unintended assembly process disruptions and/or eliminate the need to remove elastic parts 200 with splicing tape attached thereto.

Some splicing operations may be configured to weld or otherwise bond a replacement supply of a continuous elastic substrate 200a to a current supply of continuous elastic substrate 200a being used in assembly operations without the need to use splicing tape. Such welding operations may utilize hot-wire or ultrasonic apparatuses to create a thermal splice. The thermal splice process may both cut and weld the materials together. In some configurations, thermal splices may be applied so as to maintain some stretch properties, which may allow discrete elastic parts 200 with such thermal splices to advance through cross directional stretching and/or bonding operations without disrupting such operations.

As discussed above, it is to be appreciated that the continuous elastic substrate 200a and the discrete elastic parts 200 herein may be configured in various ways and may include one or more elastic materials, such as for example, elastic film and/or strands. In some configurations, the continuous elastic substrate 200a and the discrete elastic parts 200 may comprise a single layer of elastic film. In some configurations, the continuous elastic substrate 200a and the discrete elastic parts 200 may comprise a laminate of two more substrates, such as an elastic film bonded with one or more nonwoven substrates. When the continuous elastic substrate 200a is configured to comprise an elastic film bonded with one or more consolidated nonwovens, a thermal splice may be configured to melt the layers of both film and nonwoven to create a weld that traps consolidations of the nonwoven materials. In turn, the cross directional stretching process may stretch the elastic part 200 such that the weld may also extend in the cross direction by partially failing a part of the weld that has trapped the consolidated nonwoven, sometimes referred to as "popping the weld." Depending on various splicing process parameters, such as for example weld time, dwell time, and quench time and various material properties, such as for example basis weight, fiber type, and plastic characteristics, the cross directional forces necessary to pop and stretch the weld may vary. In some examples, an ultrasonic splicing apparatus including a relatively sharp cutting anvil may be configured to produce a weld that has a relatively low cross directional force required to pop and stretch. In particular, a relatively smaller overall weld may be produced when a sharp angle of the anvil may penetrate through and burst fibers in the materials without causing a relatively large melt zone, while at the same time allowing the film to weld together, resulting in a splice that may be relatively easier to stretch in the cross direction CD with reduced and/or no popping required.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of assembling absorbent articles, the method comprising steps of:
    advancing a carrier substrate at a first speed in a machine direction, the carrier substrate comprising a first longitudinal edge and a second longitudinal edge separated from the first longitudinal edge in a cross direction;
    advancing a continuous elastic substrate at a second speed in the machine direction, the continuous elastic substrate comprising a first longitudinal edge and a second longitudinal edge separated from the first longitudinal edge in the cross direction, wherein the continuous elastic substrate is stretchable in the cross direction;
    cutting an elastic part from the continuous elastic substrate, the elastic part comprising a first end region and a second end region separated from the first end region in the cross direction by a central region;
    changing a speed of the elastic part from the second speed to the first speed by rotating a first canted disk and a second canted disk at a variable angular velocity;
    stretching the central region of the elastic part in the cross direction;
    positioning the elastic part on the carrier substrate such that the stretched central region extends in the cross direction between the first and second longitudinal edges of the carrier substrate; and
    bonding the stretched central region of the elastic part with the carrier substrate.

2. The method of claim 1, further comprising a step of dividing the elastic part into a first waistband and a second waistband by cutting the carrier substrate along the cross direction through the elastic part.

3. The method of claim 1, wherein the step of bonding further comprises applying adhesive to the central region of the elastic part.

4. The method of claim 3, wherein the elastic part comprises a leading edge and a trailing edge, and wherein the elastic part defines a first length in the machine direction extending from the leading edge to the trailing edge, and wherein the step of applying adhesive to the central region of the elastic part further comprises applying adhesive along a second length of the elastic part, wherein the second length is less than the first length.

5. The method of claim 1, wherein the carrier substrate comprises a topsheet substrate comprising a first surface and an opposing second surface, and wherein the elastic part comprises a first surface and an opposing second surface.

6. The method of claim 5, wherein the step of positioning the elastic part on the carrier substrate further comprises positioning the second surface of the elastic part in a facing relationship with the first surface of the topsheet substrate.

7. The method of claim 6, further comprising steps of: positioning an absorbent core on the second surface of the topsheet substrate; and bonding a backsheet substrate with the topsheet substrate with the absorbent core sandwiched between the topsheet substrate and the backsheet substrate.

8. The method of claim 6, further comprising a step of bonding leg cuffs with the topsheet substrate.

9. The method of claim 8, wherein the step of positioning the second surface of the elastic part in a facing relationship with the first surface of the topsheet substrate is performed after the step of bonding leg cuffs with the topsheet substrate.

10. The method of claim 9, wherein a portion of the leg cuffs are positioned between the elastic part and the topsheet substrate.

11. The method of claim 1, wherein the step of cutting the elastic part from the continuous elastic substrate further comprises advancing the continuous elastic substrate between a rotating knife roll and anvil roll.

12. The method of claim 11, wherein the step of changing the speed of the elastic part further comprises accelerating the elastic part on the knife roll or the anvil roll.

13. The method of claim 1, wherein the step of stretching the central region of the elastic part in the cross direction further comprises advancing the first end region of the elastic part onto the first canted disk and advancing the second end region of the elastic part onto the second canted disk.

14. The method of claim 1, wherein the continuous elastic substrate comprises an elastic film.

15. The method of claim 14, wherein the continuous elastic substrate comprises a nonwoven bonded with the elastic film.

16. The method of claim 1, further comprising steps of:
    cutting a second elastic part from the continuous elastic substrate; and
    separating the elastic part and the second elastic part from each other in machine direction by a pitch distance.

17. The method of claim 1, further comprising steps of applying adhesive to the elastic part; and rotating the elastic part around an axis of rotation wherein the adhesive is facing radially inward.

18. A method of assembling absorbent articles, the method comprising steps of:
    advancing a continuous elastic substrate in a machine direction, the continuous elastic substrate comprising a first surface and an opposing second surface, the continuous elastic substrate comprising a first longitudinal edge and a second longitudinal edge separated from the first longitudinal edge in a cross direction to define a first width, wherein the continuous elastic substrate is stretchable in the cross direction and comprises corrugations oriented to define corrugation lines extending in the machine direction;

applying adhesive to corrugations on the first surface of the continuous elastic substrate, wherein the adhesive extends in the cross direction for a second width, wherein the second width is less than the first width;

cutting an elastic part from the continuous elastic substrate, the elastic part comprising a first end region and a second end region separated from the first end region in the cross direction by a central region, wherein a zone of adhesive is positioned on the central region and not the first and second end regions;

separating the zone of adhesive into individual stripes of adhesive by stretching the central region of the elastic part in the cross direction; and adhesively bonding the stretched central region of the elastic part to a carrier substrate with the stripes of adhesive.

19. The method of claim 18, further comprising steps of:

advancing the carrier substrate at a first speed;

advancing the continuous elastic substrate at a second speed; and changing a speed of the elastic part from the second speed to the first speed.

20. The method of claim 18, wherein the carrier substrate comprises a topsheet substrate comprising a first surface and an opposing second surface, and wherein the elastic part comprises a first surface and an opposing second surface; and further comprising steps of:

positioning the second surface of the elastic part in a facing relationship with the first surface of the topsheet substrate; and positioning an absorbent core on the second surface of the topsheet substrate; and bonding a backsheet substrate with the topsheet substrate with the absorbent core sandwiched between the topsheet substrate and the backsheet substrate.

* * * * *